United States Patent
Reddy et al.

(10) Patent No.: US 10,207,989 B2
(45) Date of Patent: Feb. 19, 2019

(54) SUBSTITUTED ALKYL DIARYL DERIVATIVES, METHODS OF PREPARATION AND USES

(71) Applicant: TEMPLE UNIVERSITY—OF THE COMMONWEALTH SYSTEM OF HIGHER EDUCATION, Philadelphia, PA (US)

(72) Inventors: M. V. Ramana Reddy, Upper Darby, PA (US); E. Premkumar Reddy, Villanova, PA (US)

(73) Assignee: TEMPLE UNIVERSITY—Of The Commonwealth System of Higher Education, Philadelphia, PA (US)

(*) Notice: Subject to any disclaimer, the term of this patent is extended or adjusted under 35 U.S.C. 154(b) by 0 days.

(21) Appl. No.: 14/429,223

(22) PCT Filed: Sep. 18, 2013

(86) PCT No.: PCT/US2013/060294
§ 371 (c)(1),
(2) Date: Mar. 18, 2015

(87) PCT Pub. No.: WO2014/047110
PCT Pub. Date: Mar. 27, 2014

(65) Prior Publication Data
US 2015/0266819 A1    Sep. 24, 2015

Related U.S. Application Data

(60) Provisional application No. 61/703,368, filed on Sep. 20, 2012.

(51) Int. Cl.
| | | |
|---|---|---|
| *C07C 231/12* | (2006.01) | |
| *C07C 235/38* | (2006.01) | |
| *C07C 311/27* | (2006.01) | |
| *C07C 315/04* | (2006.01) | |
| *C07C 317/10* | (2006.01) | |
| *C07C 317/18* | (2006.01) | |
| *C07C 317/24* | (2006.01) | |
| *C07C 317/28* | (2006.01) | |
| *C07C 319/20* | (2006.01) | |
| *C07C 323/07* | (2006.01) | |
| *C07D 207/337* | (2006.01) | |
| *A61K 31/10* | (2006.01) | |

(52) U.S. Cl.
CPC ........ *C07D 207/337* (2013.01); *C07C 231/12* (2013.01); *C07C 235/38* (2013.01); *C07C 311/27* (2013.01); *C07C 315/04* (2013.01); *C07C 317/10* (2013.01); *C07C 317/18* (2013.01); *C07C 317/24* (2013.01); *C07C 317/28* (2013.01); *C07C 319/20* (2013.01); *C07C 323/07* (2013.01); *C07C 2601/02* (2017.05)

(58) Field of Classification Search
CPC ... C07C 235/38; C07C 317/18; C07C 317/24; C07C 317/28; C07C 323/07
USPC ........... 560/12; 562/429, 430; 564/182, 440; 568/33, 34, 56
See application file for complete search history.

(56) References Cited

U.S. PATENT DOCUMENTS

| | | | |
|---|---|---|---|
| 4,443,477 A | | 4/1984 | Witte et al. |
| 5,021,414 A | * | 6/1991 | Pilgrim ................. C07C 43/225 514/237.5 |
| 5,070,099 A | | 12/1991 | Hall et al. |
| 5,545,750 A | | 8/1996 | Kempf et al. |
| 6,201,154 B1 | | 3/2001 | Reddy et al. |
| 6,359,013 B1 | | 3/2002 | Reddy et al. |
| 6,414,034 B1 | | 7/2002 | Reddy et al. |
| 6,486,210 B2 | | 11/2002 | Reddy et al. |
| 6,541,475 B2 | | 4/2003 | Reddy et al. |
| 6,548,553 B2 | | 4/2003 | Reddy et al. |
| 6,576,675 B1 | | 6/2003 | Reddy et al. |
| 6,599,932 B1 | | 7/2003 | Reddy et al. |
| 6,642,410 B2 | | 11/2003 | Reddy et al. |
| 6,646,009 B2 | | 11/2003 | Reddy et al. |
| 6,656,968 B1 | | 12/2003 | Reddy et al. |
| 6,656,973 B2 | | 12/2003 | Cosenza et al. |
| 6,667,346 B2 | | 12/2003 | Reddy et al. |
| 6,762,207 B1 | | 7/2004 | Reddy et al. |
| 6,767,926 B1 | | 7/2004 | Cosenza et al. |
| 6,787,667 B2 | | 9/2004 | Reddy et al. |
| 6,833,480 B2 | | 12/2004 | Reddy et al. |

(Continued)

FOREIGN PATENT DOCUMENTS

| | | |
|---|---|---|
| EP | 2226329 A1 | 9/2010 |
| JP | 9-003037 A | 1/1997 |

(Continued)

OTHER PUBLICATIONS

Chemical Abstract Service (CAS) STN Registry Database No. 1027391-94-1 [entered STN: Jun. 11, 2008].*
Chemical Abstract Service (CAS) STN Registry Database No. 1027535-07-4 [entered STN: Jun. 12, 2008].*
Treu et al. "12H-[2]-Benzothiepino[6,5a,5-bc]benzofuran: Synthesis of a Sulfur-Analog of Galanthamine" Heterocycles (2001), 55(9), 1727-1735.*
Farrar, W. V. "Arylamides of Halogenated Methane- and Ethane-sulphonic Acids." J. Chem. Soc. 1960, 3058-3062.*
Chemical Abstract Service (CAS) STN Registry Database No. 1215385-18-4 [entered STN: Apr. 1, 2010].*
Chemical Abstracts Service Registry No. 1329286-45-4 [Entered STN: Sep. 7, 2011].*

(Continued)

*Primary Examiner* — Amanda L Aguirre
(74) *Attorney, Agent, or Firm* — Drinker Biddle & Reath LLP

(57) ABSTRACT

Compounds according to Formula I are provided: and salts thereof, wherein $Q_1$, $Q_2$, $R_3$, $R_4$, X, and Y are as defined herein. Methods for preparing compounds of Formula I are also provided, as well as methods of treating cellular proliferative disorders, such as cancer, using compounds of Formula (I).

$$Q_2\text{-}X\text{—}Y\text{—}CHR_3\text{—}CHR_4\text{-}Q_1 \qquad (I)$$

23 Claims, No Drawings

(56) References Cited

U.S. PATENT DOCUMENTS

| | | | |
|---|---|---|---|
| 7,053,123 B2 | 5/2006 | Reddy et al. | |
| 7,161,031 B2 | 1/2007 | Reddy et al. | |
| 7,482,488 B2 | 1/2009 | Reddy et al. | |
| 7,595,347 B2 | 9/2009 | Cosenza et al. | |
| 7,598,232 B2 | 10/2009 | Reddy et al. | |
| 7,744,889 B2 | 6/2010 | Reddy et al. | |
| 7,932,242 B2 | 4/2011 | Reddy et al. | |
| 8,058,313 B2 | 11/2011 | Reddy et al. | |
| 8,106,033 B2 | 1/2012 | Reddy et al. | |
| 8,124,605 B2 * | 2/2012 | Hangauer, Jr. | C07C 49/245 514/235.5 |
| 8,143,428 B2 | 3/2012 | Reddy et al. | |
| 8,143,453 B2 | 3/2012 | Reddy et al. | |
| 8,324,190 B2 | 12/2012 | Reddy et al. | |
| 8,664,272 B2 | 3/2014 | Reddy et al. | |
| 2009/0124828 A1 | 5/2009 | Reddy et al. | |
| 2009/0163545 A1 | 6/2009 | Goldfarb | |
| 2009/0306207 A1 | 12/2009 | Reddy et al. | |
| 2011/0054037 A1 | 3/2011 | Safavy | |

FOREIGN PATENT DOCUMENTS

| | | | |
|---|---|---|---|
| WO | WO-9817648 A1 | 4/1998 | |
| WO | WO-2004/030635 A2 | 4/2004 | |
| WO | WO-2007/127366 A2 | 11/2007 | |
| WO | WO-2008/073956 A2 | 6/2008 | |
| WO | WO-2008/086047 A1 | 7/2008 | |
| WO | 2009/009041 A2 | 1/2009 | |
| WO | 2010/003127 A2 | 1/2010 | |
| WO | WO-2010003127 A2 * | 1/2010 | A61K 31/235 |
| WO | 2010/130970 A1 | 11/2010 | |

OTHER PUBLICATIONS

Wydysh et al. "Design and Synthesis of Small Molecule Glycerol 3-Phosphate Acyltransferase Inhibitors" J. Med. Chem. 2009, 52, 3317-3327.*

Chemical Abstract Service (CAS) STN Registry No. (RN) 115494-25-6 [entered STN: Jun. 10, 2009].*

Chemical Abstract Service (CAS) STN RN 1203074-22-9 [entered STN: Jan. 24, 2010], RN 1335331-65-1 [entered STN: Oct. 14, 2011], RN 1310279-58-3 [entered STN Jun. 24, 2011], RN 1258847-14-1 [entered STN: Jan. 10, 2011], RN 1391493-57-4 [entered STN Aug. 15, 2012] and RN 93949-35-0 [entered STN: Dec. 30, 1984].*

Buck, J. S. J. Am. Chem. Soc. 1931, 53, 2192-2200.*

Chemical Abstract Service STN Database [online] Registry No. 1230954-26-3 [Entered STN: Jul. 12, 2010]. (Year: 2010).*

International Search Report and Written Opinion dated May 6, 2014 for PCT/US2013/60294.

Mitin et al., "Palladium-Catalyzed Arylation of Sulfones", Russian Journal of Organic Chemistry, vol. 40, No. 6, pp. 802-812 (2004).

Higuchi et al., "Flash Pyrolysis of Selenides. Syntheses of Bibenzyls, Olefins, and Related Compounds", Bull. Chem. Soc. Jpn., vol. 55, No. 1, pp. 182-187 (1982).

Dodson et al., "Reactions of Sulphones with Grignard Reagents", Chem. Commun. (London), pp. 352-353 (1965).

Padama et al., "Synthesis of a new class of 2-oxazolines and 2-thiazolines", Indian J. Chem., vol. 47B, pp. 1713-1725 (Nov. 2008).

Padmavathi et al., "Michael adducts of vinyl sulfones; source for thiadiazoles, oxadiazoles and triazoles", J Heterocyclic Chem., vol. 45(6), pp. 1633-1639 (2008).

Biellmann et al., "Allylic and Benzylic Carbanions Substituted by Heteroatoms", Organic Reactions, pp. 1-300 (1982).

Padmavathi et al., "Michael Adducts—Synthons for a New Class of 1,4-dispirocyclohexane Derivatives", Indian J. of Chem., vol. 45B, pp. 808-812 (Mar. 2006).

Padmavathi et al., "Synthesis and Bioassay of Amino-pyrazolone, Amino-isoxazolone and Amino-pyrimidinone Derivatives", Chem. Pharm. Bull., vol. 55(12), pp. 1704-1709 (2007).

Tishchenko et al., "Synthesis of propoxy- and butoxyphenacyl arcylthio ethers by thiolysis of alkoxyl-substituted acyloxiranes", Caplus, Accession No. 1978:22294, CAN 88:22294, Abstract (1977).

Reddy et al., "Stereospecific synthesis of some new Z- and E-cyclopropyl benzyl sulfones and E,Z- and E,Ebis (cyclopropyl)sulfones by PTC method", Caplus, Accession No. 1995:259329, CAN 122:132682, Abstract (1994).

Evans et al., "The Epoxy-Ramberg-Backlund Reaction:A New Route to Allylic Alcohols", Tetrahedron .Letters, vol. 38, No. 17, pp. 3055-3058 (1997).

Bin et al., "Potassium Hydroxide-Mediated Novel Rearrangement of 2-Alkyl-sulfonyl-2-arylsulfonyl-1-phenylethanones to 1-Aryl-2-(arylsulfonylmethanesulfonyl)ethanones", Organic Letters vol. 6, No. 23, pp. 4297-4300 (2004).

Padmavathi et al., Michael Addition of Active Methylene Compounds to ?,b-unsaturated Sulfones, Indian J. Chem., vol. 44B, pp. 2569-2574 (Dec. 2005).

Evans et al., "The Epoxy-Ramberg-Backlund Reaction (ERBR): A Sulfone-Based Method for the Synthesis of Allylic Alcohols", Eur. J. Org. Chem., pp. 1740-1754 (2006).

Castang et al., "N-Sulfonyl homoserine lactones as antagonists of bacterial quorum sensing", Bioorganic & Medicinal Chemistry Letters, 14, pp. 5145-5149 (2004).

Sohmiya et al., "Solid-State Organic Reactions Proceeding by Pulverization: Oxidation and Halogenation with Iodosobenzene and Inorganic Solid Supports", Tetrahedron, vol. 54, pp. 13737-13750 (1998).

Lv et al., "Screening candidate anticancer drugs for brain tumor chemotherapy: Pharmacokinetic-driven approach for a series of (E)-N-(substituted aryl)-3-(substituted phenyl) propenamide analogues", (Invest New Drugs: DOI 10.1007/ s10637-012-9806-x) Springer Science+Business Media, LLC (Published online Mar. 1, 2012).

Treu et al., "12H-[2]-benzothiepino[6,5a,5-bc]benzofuran: synthesis of a sulfur-analog of galanthamine", Heterocycles, vol. 55, Issue 9, pp. 1727-1735 (2001).

Reddy et al., "Synthesis and Cyclopropanation of (E)- and (Z)-Styryl Benzyl Sulfones", Sulfur Letters, vol. 13, No. 2, pp. 83-87 (1991).

Barbosa et al., "Synthesis of Several New Phenylethylamides of Substituted Benzoic Acids", Quimica Nova, 13(4), pp. 332-334 (1990).

Doi et al., "Abnormal Products in the Bischler-Napieralski Isoquinoline Synthesis", Journal of the Chemical Society, Perkin Transactions 1: Organic and Bio-Organic Chemistry, (15), pp. 2217-2221 (1997).

Reddy, et al. "Discovery of a Clinical Stage Multi-Kinase Inhibitor Sodium (E)-2-{2-Methoxy-5-[(2',4'6'trimethoxystyrylsulfonyl)methyl]phenylamino}-acetate (ON 01910.Na): Synthesis, Structure-Activity Relationship, and Biological Activity," Journal of Medicinal Chemistry, 2011, 54, 6254-6276.

Fang, et al. "Biological evaluation of sulfone derivatives as anti-inflammatory and tumor cells growth inhibitory agents," International Immunopharmacology 6 (2006) 1699-1705.

Pingaew, et al., "Synthesis and cytotoxicity of novel N-sulfonyl-1,2,3,4-tetrahydriosoquinoline thiosemicarbazone derivatives", Med Chem Res, (2013) vol. 22, pp. 267-277.

Raja et al., "Friedel-Crafts acylation with amides", J. Org. Chem. (2012) vol. 77,(2012), pp. 5788-5793.

File Registry on STN, RN 141666-92-4, Entered STN: Jun. 5, 1992.

File Registry on STN, RN 349139-48-6, Entered STN: Jul. 27, 2001.

Cuny, G. D., Synthesis of (±)-aporphine utilizing Pictet-Spengler and intramolecular phenol ortho-Arylation reactions, Tetrahedron Letters, 2004, vol. 45, pp. 5167-5170.

CAS Registry No. 1061871-80-4; STN Entry Date: Oct. 15, 2008; 4-methoxy-N-[2-(4-methoxyphenyl)ethyl]-3-nitrobenzenesulfonamide.

CAS Registry No. 87085-06-5; STN Entry Date: Jun. 7, 2006; 1-chloro-4[[[2-(4-luorophenyl)ethyl]thio]methyl]benzene.

Examination Report No. 1 dated Jul. 7, 2017 in Australian Patent Application No. 2013318206.

Notice for Reasons for Refusal dated Jul. 4, 2017 in Japanese Patent Application No. 2015-533142 with an English translation.

(56) References Cited

OTHER PUBLICATIONS

Li, J. et al. "Selective reduction of a,β-unsaturated amides with NaBh4-CuCL/EtOH," Journal of Henan Normal University (Natural Science Edition), vol. 40, No. 2, pp. 101-103, 2012.Li, J. et al. "Selective reduction of a,β-Unsaturated amides with NaBh4-CuCL/EtOH," Journal of Henan Normal University (Natural Science Edition), vol. 40, No. 2, pp. 101-103, 2012.
Examination Report No. 2 dated May 21, 2018 in Australian Patent Application No. 2013318206.
Office Action dated Jan. 18, 2018 in European Patent Application No. 13839254.3.
Chemical Abstracts Service Database accession No. 2012:1630172: Wang et al. "Synthesis and B structure-activity relationship of N-(2-arylethyl) isoquinoline derivatives as anti-cancer agents" (2012) [retrieved from STN Database online].

\* cited by examiner

SUBSTITUTED ALKYL DIARYL DERIVATIVES, METHODS OF PREPARATION AND USES

CROSS-REFERENCE TO RELATED APPLICATION

The benefit of the filing date of U.S. Provisional Patent Applications No. 61/703,368, filed Sep. 20, 2012 is hereby claimed. The entire disclosure of the aforesaid application is incorporated herein by reference.

FIELD OF THE INVENTION

The invention relates to compounds, methods for their preparation, and compositions including them. The invention further provides methods for the treatment of cellular proliferative disorders, including, but not limited to, cancer.

BACKGROUND OF THE INVENTION

Cellular proliferative disorders such as cancer are among the most common causes of death in developed countries. That said, many cellular proliferative disorders have no available cures or few, if any, treatment options to slow the progression of the disease. For cellular proliferative diseases for which treatments exist, undesirable side effects and limited efficacy often call into question the utility of a given treatment. This is particularly true when the available treatment option(s) may not appreciably prolong life, but have a definitive adverse effect on the quality of time remaining. Thus, identifying new effective drugs for cellular proliferative disorders, and in particular cancer, is a continuing focus of medical research.

SUMMARY OF THE INVENTION

It has been found that certain compounds and compositions are useful for the treatment of cancer and other cellular proliferative disorders. The biologically active compounds of the invention are substituted alkyl diaryl derivatives and related derivatives thereof.

Provided is a compound of Formula I or a salt thereof:

$$Q_2\text{-}X\text{—}Y\text{—}CHR_3\text{—}CHR_4\text{-}Q_1 \qquad (I)$$

wherein:

$Q_1$ is selected from the group consisting of substituted or unsubstituted aryl and substituted or unsubstituted heteroaryl, with up to 5 substituents selected from the group consisting of:
fluoro; chloro; bromo; nitro; —$NR_{10}R_{11}$; aroylamino; cyano; carboxy; carboxamido; trifluoromethyl; —O—$R_{10}$; [—N(—$R_1$)—$(CH_2)_m$—C(—$R_5$)(—$R_6$)—$(CH_2)_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$Q_2$ is selected from the group consisting of substituted or unsubstituted aryl and substituted or unsubstituted heteroaryl, with up to 5 substituents selected from the group consisting of:
fluoro; chloro; bromo; nitro; —$NR_{10}R_{11}$; aroylamino; cyano; carboxy; carboxamido; trifluoromethyl; —O—$SO_2$—OH; —O—P(=O)($OR_8$)$_2$; —O—$R_{10}$; [—N(—$R_9$)—$(CH_2)_m$—C(—$R_5$)(—$R_6$)—$(CH_2)_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

wherein at least one of $Q_1$ and $Q_2$ is substituted with a substituent other than unsubstituted phenyl;

X is selected from the group consisting of —S—, —S(=O)—, —S(=O)$_2$—, —CH($R_2$)—, —C(=O)—, and —N(—$R_1$)—;

Y is selected from the group consisting of —N(—$R_1$)—, —C(=O)—, —S—, —S(=O)— and —S(=O)$_2$—;

$R_1$ and $R_2$ are each independently selected from the group consisting of H; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$R_3$ and $R_4$ are each independently selected from the group consisting of H; a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—; and $C_1$-$C_{10}$ saturated or unsaturated, straight or branched, cyclic, chiral or achiral hydrocarbyl group;

or $R_3$ and $R_4$ may combine to form a saturated or unsaturated carbocyclic ring with from 3 to 4 carbon atoms, wherein one or more carbon atoms is optionally replaced with —N(—$R_1$)— or —S— to form a heterocycle, or $R_3$ and $R_4$ may combine to form a saturated or unsaturated carbocyclic ring with from 5 to 6 carbon atoms, wherein one or more carbon atoms is optionally replaced with —N(—$R_1$)—, —O—, or —S—;

or $R_4$ and $Q_2$ may combine to form a carbocyclic ring;

$R_5$ and $R_6$ are each independently selected from the group consisting of H; halo; and a $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_6$) alkyl, ($C_1$-$C_6$) dialkyl amino, or acylamino;

or $R_5$ and $R_6$ may combine to form a saturated or unsaturated carbocyclic ring with from 3 to 6 carbon atoms, wherein one or more carbon atoms is optionally replaced with —N(—$R_1$)—, —O—, or —S—;

$R_7$ is selected from the group consisting of H; a $C_1$-$C_{10}$ saturated or unsaturated, straight or branched, cyclic or acyclic, chiral or achiral hydrocarbyl group; and an inorganic cation or an organic cation, to form a salt;

$R_8$ is each independently selected from the group consisting of H and ($C_1$-$C_7$) hydrocarbyl;

$R_9$ is selected from the group consisting of H and —$(CH_2)_m$—C(—$R_5$)(—$R_6$)—$(CH_2)_n$—$COOR_7$;

$R_{10}$ is selected from the group consisting of H, branched or unbranched ($C_1$-$C_6$)alkyl, and ($C_2$-$C_8$)acyl;

$R_{11}$ is selected from the group consisting of H, branched or unbranched ($C_1$-$C_6$)alkyl, and ($C_2$-$C_8$)acyl;

m and n are each independently 0-2;

z is 1-2;

provided that if $Q_1$ is substituted with hydroxy or a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—, then $Q_2$ cannot be substituted by bromo in the 2-position; and provided that if X is —S—, —S(=O)—, or —S(=O)$_2$—, then Y is —N(—R$_1$)—.

The present disclosure further provides a pharmaceutical composition comprising a pharmaceutically acceptable carrier and a compound of Formula I, or a pharmaceutically acceptable salt thereof.

The present disclosure further provides a method of treating an individual suffering from a cellular proliferative disorder, comprising administering to the individual an effective amount of at least one compound of Formula I, or a pharmaceutically acceptable salt thereof.

In particular embodiments, the cellular proliferative disorder is selected from the group consisting of cancer, malignant and benign tumors, blood vessel proliferative disorders, autoimmune disorders, and fibrotic disorders.

In particular embodiments, the cellular proliferative disorder is selected from the group consisting of hemangiomatosis in newborn, secondary progressive multiple sclerosis, atherosclerosis, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy, noncancerous lymphocellular proliferative disorders, and cancer.

In particular embodiments, the cellular proliferative disorder is cancer. In certain embodiments, the cancer is selected from the group consisting of ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

The present disclosure further provides a method of inducing apoptosis of cancer cells in an individual afflicted with cancer, comprising administering to the individual an effective amount of at least one compound of Formula I, or a pharmaceutically acceptable salt thereof.

In certain embodiments, the cancer cells are tumor cells. In particular embodiments, the tumor cells are selected from the group consisting of ovarian, cervical, breast, prostate, testicular, lung, renal, colorectal, skin and brain tumor cells.

In certain embodiments, the invention is a compound of Formula I, or salt thereof, for use in medicine. In other embodiments, the invention is a compound of Formula I or a salt thereof, for treatment of a cellular proliferative disorder. In other embodiments, the invention provides a use of a compound according to Formula I, or a salt thereof, for preparation of a medicament for treatment of a cellular proliferative disorder. The present invention further provides a medicament for treatment of a cellular proliferative disorder, containing a compound of Formula I, or a pharmaceutically acceptable salt thereof.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

The compounds and compositions of the invention believed to selectively inhibit proliferation of cancer cells, and kill various tumor cell types without killing (or with reduced killing of) normal cells. Cancer cells are killed at concentrations where normal cells may be temporarily growth-arrested but not killed.

The compounds of the invention are believed to inhibit the proliferation of tumor cells, and for some compounds, induce cell death. Cell death results from the induction of apoptosis. The compounds are believed effective against a broad range of tumor types, including but not limited to the following: ovarian cancer, breast cancer, prostate cancer, lung cancer, renal cancer, colorectal cancer, brain cancer and leukemia.

The compounds are also believed useful in the treatment of non-cancer cellular proliferative disorders, including but not limited to the following: hemangiomatosis in newborn, secondary progressive multiple sclerosis, atherosclerosis, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy, noncancerous lymphocellular proliferative disorders, and cancer.

I. DEFINITIONS

1. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The expression "effective amount", when used to describe therapy to an individual suffering from a cancer or other cellular proliferative disorder, refers to the amount of a compound according to Formula I that inhibits the abnormal growth or proliferation, or alternatively induces apoptosis of cancer cells, preferably tumor cells, resulting in a therapeutically useful and selective cytotoxic effect on proliferative cells.

The term "cellular proliferative disorder" means a disorder wherein unwanted cell proliferation of one or more subsets of cells in a multicellular organism occurs. In some such disorders, cells are made by the organism at an atypically accelerated rate.

2. Chemical

In the following paragraphs some of the definitions include examples. The examples are intended to be illustrative, and not limiting.

The term "alkyl", by itself or as part of another substituent means, unless otherwise stated, a straight, or branched chain hydrocarbon having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, and hexyl. Most preferred is ($C_1$-$C_6$) alkyl, particularly ethyl, methyl and isopropyl.

The term "alkoxy" employed alone or in combination with other terms means, unless otherwise stated, an alkyl group, as defined above, connected to the rest of the molecule via an oxygen atom, such as, for example, methoxy, ethoxy, 1-propoxy, 2-propoxy (isopropoxy) and the higher homologs and isomers. The alkyl portion of the alkoxy group can have a designated number of carbon atoms as defined for alkyl groups above. Preferred are ($C_1$-$C_3$)alkoxy, particularly ethoxy and methoxy.

The term "carboxy" means —C(=O)—O-J, wherein J can be H, an inorganic or an organic counter ion, including an alkaline metal and a quaternary ammonium ion formed with an organic base, for example, trimethamine. For example, a carboxy includes a carboxylic acid —(C=O)—OH and metal carboxylate, such as —(C=O)—O⁻Na⁺.

The term "alkylamino" means —NH-alkyl, preferably —NH—($C_1$-$C_6$)alkyl.

The term "acylamino" means —NH—(C=O)-alkyl, preferably —NH—(C=O)—($C_1$-$C_6$)alkyl.

The term "dialkyl amino" means —N[alkyl]$_2$, preferably —N[($C_1$-$C_6$)alkyl]$_2$.

The term "aroylamino" means —NH—(C=O)-aryl.

The term "carboxamido" means —(C=O)—NH$_2$.

The term "carbocyclic ring" refers to an cycloalkane ring formed by combining substituents attached to different carbon atoms. Preferably, $R_4$ and $Q_2$ can combine to form a cyclohexyl ring.

The terms "halo" or "halogen" by themselves or as part of another substituent mean, unless otherwise stated, a fluorine, chlorine, bromine, or iodine atom. Preferably, a halogen includes fluorine, chlorine, or bromine, more preferably, fluorine or chlorine.

The term "aromatic" refers to a carbocycle or heterocycle having one or more polyunsaturated rings having aromatic character (i.e. having (4n+2) delocalized π (pi) electrons where n is an integer).

The term "aryl", employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl. Preferred are phenyl and naphthyl, most preferred is phenyl.

"Substituted aryl" means an aryl, as defined above, substituted by one, two, three, four, or five substituents. In some embodiments, the substituents are selected from among the group consisting of halogen, fluoro; chloro; bromo; nitro; —NR$_{10}$R$_{11}$; aroylamino; cyano; carboxy; carboxamido; trifluoromethyl; —O—R$_{10}$; [—N(—R$_1$)—(CH$_2$)$_m$—C(—R$_5$)(—R$_6$)—(CH$_2$)$_n$—COOR$_7$]$_z$; [—N(—R$_9$)—(CH$_2$)$_m$—C(—R$_5$)(—R$_6$)—(CH$_2$)$_n$—COOR$_7$]$_z$; and $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—. Preferably, a substituted aryl contains one to three substituents selected from methoxy, hydroxy, amino, and chloro, and fluoro, more preferably selected from amino, hydroxy, and methoxy.

In some embodiments, when a substituent is referred to as located at a 2, 3, 4, or 5 position, and/or otho, meta, or para substituted or an aryl group, then the aryl group is a phenyl group numbered as shown below:

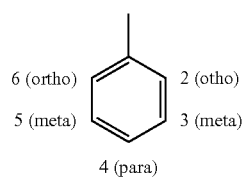

The term "unsubstituted aryl" refers to an aryl, as defined above, which has no substituents.

The term "heteroaryl" or "heteroaromatic" refers to a heterocycle having aromatic character. A polycyclic heteroaryl may include one or more rings which are partially saturated. Examples of heteroaryl groups include: pyridyl, pyrazinyl, pyrimidinyl, particularly 2- and 4-pyrimidinyl, pyridazinyl, indolyl (2-, 3-, 4-, 5-, 6- and 7-), thienyl, furyl, and pyrrolyl, preferably 2-, 3- and 4-pyridyl.

The term "substituted heteroaryl" refers to a heteroaryl, as defined above, substituted by one, two, three, four, or five substituents. In some embodiments, the substituents are selected from among the group consisting of fluoro; chloro; bromo; nitro; amino; acylamino; aroylamino; cyano; carboxy; carboxamido; trifluoromethyl; [—N(—R$_1$)—(CH$_2$)$_m$—C(—R$_5$)(—R$_6$)—(CH$_2$)$_n$—COOR$_7$]$_z$; —OR$_{10}$; [—N(—R$_9$)—(CH$_2$)$_m$—C(R$_5$)(—R$_6$)—(CH$_2$)$_n$—COOR$_7$]$_z$; and $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—. Preferably, a substituted heteroaryl contains one to three substituents selected from methoxy, hydroxy, amino, chloro, and fluoro, more preferably selected from amino, and methoxy.

The term "unsubstituted heteroaryl" refers to a heteroaryl, as defined above, which has no substituents.

The term "heterocycle" or "heterocyclyl" or "heterocyclic" by itself or as part of another substituent means, unless otherwise stated, an unsubstituted or substituted, stable, mono- or multi-cyclic heterocyclic ring system which consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Examples of heterocyclyl (non-aromatic) include monocyclic groups such as: aziridinyl, oxiranyl, thiiranyl, azetidinyl, oxetanyl, thietanyl, pyrrolidinyl, pyrrolinyl, imidazolinyl, pyrazolidinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, 1,4-dihydropyridinyl, piperazinyl, morpholinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepanyl, 4,7-dihydro-1,3-dioxepinyl and hexamethyleneoxidyl, preferably piperidinyl, piperazinyl and morpholinyl.

Examples of polycyclic heterocycles include: indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl and quinolizidinyl.

The aforementioned listing of heterocyclyl and heteroaryl moieties is intended to be representative and not limiting.

The term "hydrocarbyl" refers to any moiety comprising only hydrogen and carbon atoms, unless otherwise explicitly stated. A hydrocarbyl can also form a non-aromatic, such as cyclohexane, or an aromatic ring, such as a substituted or unsubstituted ($C_6$-$C_{10}$)aryl group. Preferred hydrocarbyl groups are ($C_1$-$C_{12}$)hydrocarbyl, more preferred are ($C_1$-$C_7$) hydrocarbyl, and most preferred are benzyl and ($C_1$-$C_6$) alkyl. For example, a hydrocarbyl group that is substituted by an oxygen includes ethers, such as —$CH_2$—O—$CH_3$.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

Where a substituent is an alkyl or alkoxy group, the carbon chain may be branched, straight or cyclic, with straight being preferred.

II. COMPOUNDS OF THE INVENTION

In one aspect, the invention is directed to a compound of Formula I, or a salt thereof:

$$Q_2\text{-}X\text{—}Y\text{—}CHR_3\text{—}CHR_4\text{-}Q_1 \quad (I)$$

wherein:

$Q_1$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$R_{10}$; [—N(—$R_1$)—($CH_2$)$_m$—C(—$R_5$)(—$R_6$)—($CH_2$)$_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$Q_2$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$SO_2$—OH; —O—P(=O)(O$R_8$)$_2$; —O—$R_{10}$; [—N(—$R_9$)—($CH_2$)$_m$—C(—$R_5$)(—$R_6$)—($CH_2$)$_n$—$COOR_7$]$_z$; and $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

wherein at least one of $Q_1$ and $Q_2$ is substituted with a substituent other than unsubstituted phenyl;

X is selected from the group consisting of —S—, —S(=O)—, —S(=O)$_2$—, —CH($R_2$)—, —C(=O)—, and —N(—$R_1$)—;

Y is selected from the group consisting of —N(—$R_1$)—, —C(=O)—, —S—, —S(=O)— and —S(=O)$_2$—;

$R_1$ and $R_2$ are each independently selected from the group consisting of H; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$R_3$ and $R_4$ are each independently selected from the group consisting of H; $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—; and $C_1$-$C_{10}$ saturated or unsaturated, straight or branched, cyclic, chiral or achiral hydrocarbyl group;

or $R_3$ and $R_4$ may combine to form a saturated or unsaturated carbocyclic ring with from 3 to 4 carbon atoms, wherein one or more carbon atoms is optionally replaced with —N(—$R_1$)— or —S— to form a heterocycle, or $R_3$ and $R_4$ may combine to form a saturated or unsaturated carbocyclic ring with from 5 to 6 carbon atoms, wherein one or more carbon atoms is optionally replaced —N(—$R_1$)—, —O—, or —S—;

or $R_4$ and $Q_2$ may combine to form a carbocyclic ring;

$R_5$ and $R_6$ are each independently selected from the group consisting of H; halo; and $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_6$) alkyl, ($C_1$-$C_6$) dialkyl amino or acylamino;

or $R_5$ and $R_6$ may combine to form a saturated or unsaturated carbocyclic ring with from 3 to 6 carbon atoms, wherein one or more carbon atoms is optionally replaced with —N(—$R_1$)—, —O— or —S—;

$R_7$ is selected from the group consisting of H; and a $C_1$-$C_{10}$ saturated or unsaturated, straight or branched, cyclic or acyclic, chiral or achiral hydrocarbyl group; and an inorganic cation or an organic cation, to form a salt;

$R_8$ is each independently selected from the group consisting of H and ($C_1$-$C_7$) hydrocarbyl;

$R_9$ is selected from the group consisting of H and —($CH_2$)$_m$—C(—$R_5$)(—$R_6$)—($CH_2$)$_n$—$COOR_7$;

$R_{10}$ is selected from the group consisting of H, branched or unbranched ($C_1$-$C_6$)alkyl, and ($C_2$-$C_8$)acyl;

$R_{11}$ is selected from the group consisting of H, branched or unbranched ($C_1$-$C_6$)alkyl, and ($C_2$-$C_8$)acyl;

m and n are each independently 0-2;

z is 1-2;

provided that if $Q_1$ is substituted with hydroxy or a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—, then $Q_2$ cannot be substituted by bromo in the 2-position; and provided that if X is —S—, —S(=O)—, or —S(=O)$_2$—, then Y is —N(—$R_1$)—.

In certain embodiments, the salt of a compound of Formula I is a pharmaceutically acceptable salt.

In some embodiments, $Q_1$ is substituted phenyl, and is substituted in at least the 4-position. In some embodiments, $Q_1$ is di-substituted phenyl, and is substituted at the 2- and 4-positions. In some embodiments, $Q_1$ is tri-substituted phenyl, and is substituted at the 2-, 4- and 6-positions.

In some embodiments, $Q_2$ is substituted phenyl, and is substituted in at least the 4-position. In some embodiments, $Q_2$ is di-substituted phenyl, and is substituted at the 3- and 4-positions.

Another particular embodiment of the invention comprises a compound of Formula I, or a salt thereof, wherein $R_3$ is H and $R_4$ is H.

Another particular embodiment of the invention comprises a compound of Formula I, or a salt thereof, wherein $Q_1$ is substituted or unsubstituted aryl, with up to 5 substituents selected from the group consisting of fluoro; chloro; bromo; nitro; —$NR_{10}R_{11}$; aroylamino; cyano; carboxy; carboxamido; trifluoromethyl; [—N(—$R_1$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_1$ is substituted or unsubstituted heteroaryl, with up to 5 substituents selected from the group consisting of fluoro; chloro; bromo; nitro; —$NR_{10}R_{11}$; aroylamino; cyano; carboxy; carboxamido; trifluoromethyl; [—N(—$R_1$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_1$ is selected from the group consisting of substituted or unsubstituted aryl and substituted or unsubstituted heteroaryl, with up to 5 substituents selected from the group consisting of nitro; —$NR_{10}R_{11}$; aroylamino; cyano; carboxy; carboxamido; trifluoromethyl; [—N(—$R_1$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_1$ is selected from the group consisting of substituted or unsubstituted aryl, with up to 5 substituents selected from the group consisting of fluoro; chloro; bromo; ($C_1$-$C_3$)alkoxy; nitro; —$NR_{10}R_{11}$; and [—N(—$R_1$)—$(CH_2)_m$—C(—$R_5$)(—$R_6$)—$(CH_2)_n$—$COOR_7$]$_z$.

Another particular embodiment of the invention comprises a compound of Formula I, or a salt thereof, wherein $Q_1$ is substituted aryl, with up to 5 fluoro substituents.

Another particular embodiment of the invention comprises a compound of Formula I, or a salt thereof, wherein $Q_1$ is substituted aryl, with up to 5 ($C_1$-$C_3$)alkoxy substituents. In certain embodiments of ($C_1$-$C_3$)alkoxy substitution, the aryl is phenyl, and the phenyl is substituted with ($C_1$-$C_3$)alkoxy in at least the 4-position. In some embodiments, the phenyl is trisubstituted with ($C_1$-$C_3$)alkoxy, at the 2-, 4- and 6-positions.

Another particular embodiment of the invention comprises a compound of Formula I, or a salt thereof, wherein $Q_1$ is selected from the group consisting of substituted or unsubstituted aryl, with up to 5 substituents selected from the group consisting of ($C_1$-$C_3$)alkoxy; and carboxy.

Another particular embodiment of the invention comprises a compound of Formula I, or a salt thereof, wherein $Q_1$ is selected from the group consisting of substituted or unsubstituted aryl, with up to 5 substituents selected from the group consisting of ($C_1$-$C_3$)alkoxy; and [—N(—$R_1$)—$(CH_2)_m$—C(—$R_5$)(—$R_6$)—$(CH_2)_n$—$COOR_7$]$_z$.

Another particular embodiment of the invention comprises a compound of Formula I, or a salt thereof, wherein $Q_1$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$R_{10}$; [—N(—$R_1$)—$(CH_2)_m$—C(—$R_5$)(—$R_6$)—$(CH_2)_n$—$COOR_7$]$_z$; and a $C_1$-$C_{10}$ saturated or unsaturated, straight or branched, cyclic or acyclic, chiral or achiral hydrocarbyl group, wherein optionally one or two carbon atoms of the hydrocarbyl group is replaced by —N(—$R_1$)—, —O— or —S—.

In some embodiments, $Q_1$ is substituted aryl with 1, 2, 3, 4 or 5 substituents thereon being aryl and/or heteroaryl.

Another particular embodiment of the invention comprises a compound of Formula I, or a salt thereof, wherein $Q_2$ is substituted or unsubstituted aryl, with up to 5 substituents selected from the group consisting of fluoro; chloro; bromo; nitro; —$NR_{10}R_{11}$; aroylamino; cyano; carboxy; carboxamido; trifluoromethyl; —O—$SO_2$—OH; —O—P(=O)(O$R_8$)$_2$; [—N(—$R_9$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_2$ is substituted or unsubstituted heteroaryl, with up to 5 substituents selected from the group consisting of fluoro; chloro; bromo; nitro; —$NR_{10}R_{11}$; aroylamino; cyano; carboxy; carboxamido; trifluoromethyl; —O—$SO_2$—OH; —O—P(=O)(O$R_8$)$_2$; [—N(—$R_9$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_2$ is substituted or unsubstituted heteroaryl, with up to 5 substituents selected from the group consisting of fluoro; chloro; nitro; —$NR_{10}R_{11}$; aroylamino; cyano; carboxy; carboxamido; trifluoromethyl; —O—$SO_2$—OH; —O—P(=O)(O$R_8$)$_2$; [—N(—$R_9$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_2$ is selected from the group consisting of substituted or unsubstituted aryl and substituted or unsubstituted heteroaryl, with up to 5 substituents selected from the group consisting of nitro; —$NR_{10}R_{11}$; aroylamino; cyano; carboxy; carboxamido; trifluoromethyl; —O—$SO_2$—OH; —O—P(=O)(O$R_8$)$_2$; [—N(—$R_9$)—$(CH_2)_m$—C(—$R_5$)(—$R_6$)—$(CH_2)_n$—$COOR_7$]$_z$; and —O—$R_{10}$.

Another particular embodiment of the invention comprises a compound of Formula I, or a salt thereof, wherein $Q_2$ is selected from the group consisting of substituted or unsubstituted aryl, with up to 5 substituents selected from the group consisting of chloro; ($C_1$-$C_3$)alkoxy; nitro; —$NR_{10}R_{11}$; hydroxy; —O—$SO_2$—OH; —O—P(=O)(O$R_8$)$_2$; and [—N(—$R_9$)—$(CH_2)_m$—C(—$R_5$)(—$R_6$)—$(CH_2)_n$—$COOR_7$]$_z$.

Another particular embodiment of the invention comprises a compound of Formula I, or a salt thereof, wherein $Q_2$ is selected from the group consisting of substituted or unsubstituted aryl, with up to 5 substituents selected from the group consisting of fluoro; ($C_1$-$C_3$)alkoxy; cyano; carboxy; carboxamido; and hydroxy.

Another particular embodiment of the invention comprises a compound of Formula I, or a salt thereof, wherein $Q_2$ is selected from the group consisting of substituted or unsubstituted aryl, with up to 5 substituents selected from the group consisting of ($C_1$-$C_3$)alkoxy and chloro.

Another particular embodiment of the invention comprises a compound of Formula I, or a salt thereof, wherein $Q_2$ is selected from the group consisting of substituted or unsubstituted aryl, with up to 5 substituents selected from the group consisting of —$NR_{10}R_{11}$; and hydroxy.

Another particular embodiment of the invention comprises a compound of Formula I, or a salt thereof, wherein $Q_2$ is selected from the group consisting of: substituted or unsubstituted aryl, with up to 5 substituents selected from the group consisting of $(C_1-C_3)$alkoxy; and $-NR_{10}R_{11}$.

Another particular embodiment of the invention comprises a compound of Formula I, or a salt thereof, wherein $Q_2$ is selected from the group consisting of: substituted or unsubstituted aryl, with up to 5 substituents selected from the group consisting of $(C_1-C_3)$alkoxy; and $[-N(R_9)-(CH_2)_m-C(-R_5)(-R_6)-(CH_2)_n-COOR_7]_z$.

Another particular embodiment of the invention comprises a compound of Formula I, or a salt thereof, wherein $Q_2$ is selected from the group consisting of substituted or unsubstituted aryl, with up to 5 substituents selected from the group consisting of $(C_1-C_3)$alkoxy; and hydroxy.

In any of the preceding embodiments defining $Q_2$, in one preferred sub-embodiment $Q_2$ is substituted phenyl with a substituent on at least the 4-position. In some embodiments, $Q_2$ is di-substituted phenyl, and is substituted at the 3- and 4-positions.

In some embodiments, $Q_2$ is substituted aryl with 1, 2, 3, 4 or 5 substituents thereon being aryl and/or heteroaryl.

Another particular embodiment of the invention comprises a compound of Formula I, or a salt thereof, wherein X is selected from the group consisting of $-S-$, $-S(=O)-$, $-S(=O)_2-$, $-CH(R_2)-$, $-C(=O)-$, and $-N(-R_1-)-$.

Another particular embodiment of the invention comprises a compound of Formula I, or a salt thereof, wherein X is $-CH(R_2)-$.

Another particular embodiment of the invention comprises a compound of Formula I, or a salt thereof, wherein X is $-C(=O)-$.

Another particular embodiment of the invention comprises a compound of Formula I, or a salt thereof, wherein X is $-N(-R_1-)-$.

Another particular embodiment of the invention comprises a compound of Formula I, or a salt thereof, wherein X is $-S-$.

Another particular embodiment of the invention comprises a compound of Formula I, or a salt thereof, wherein X is $-S(=O)-$.

Another particular embodiment of the invention comprises a compound of Formula I, or a salt thereof, wherein X is $-S(=O)_2-$.

Another particular embodiment of the invention comprises a compound of Formula I, or a salt thereof, wherein Y is $-N(-R_1)-$.

Another particular embodiment of the invention comprises a compound of Formula I, or a salt thereof, wherein Y is $-C(=O)-$.

Another particular embodiment of the invention comprises a compound of Formula I, or a salt thereof, wherein Y is $-S-$.

Another particular embodiment of the invention comprises a compound of Formula I, or a salt thereof, wherein Y is $-S(=O)-$.

Another particular embodiment of the invention comprises a compound of Formula I, or a salt thereof, wherein Y is $-S(=O)_2-$.

Another particular embodiment of the invention comprises a compound of Formula I, or a salt thereof, wherein X is $-CH(R_2)-$ or $-N(-R_1-)-$; and Y is $-S(=O)_2-$.

Another particular embodiment of the invention comprises a compound of Formula I, or a salt thereof, wherein X is $-N(-R_1)-$; and Y is $-C(=O)-$.

Another particular embodiment of the invention comprises a compound of Formula I, or a salt thereof, wherein X is $-N(-R_1)-$; and Y is $-S(=O)_2-$.

Another particular embodiment of the invention comprises a compound of Formula I, or a salt thereof, wherein $R_1$ is selected from the group consisting of H and a $C_1-C_{10}$ saturated or unsaturated, straight or branched, cyclic or acyclic, chiral or achiral hydrocarbyl group, wherein optionally at least one carbon atom of the hydrocarbyl group is replaced by $-N(-R_1)-$, $-O-$ or $-S-$.

Another particular embodiment of the invention comprises a compound of Formula I, or a salt thereof, wherein $R_1$ is selected from the group consisting of H and a $C_1-C_{10}$ saturated or unsaturated, straight or branched, acyclic, chiral or achiral hydrocarbyl group, wherein optionally at least one carbon atom of the hydrocarbyl group is replaced by $-N(-R_1)-$, $-O-$ or $-S-$.

Another particular embodiment of the invention comprises a compound of Formula I, or a salt thereof, wherein $R_1$ is selected from the group consisting of H and a $C_1-C_{10}$ saturated, straight or branched, acyclic, chiral or achiral hydrocarbyl group, wherein optionally at least one carbon atom of the hydrocarbyl group is replaced by $-N(-R_1)-$, $-O-$ or $-S-$.

Another particular embodiment of the invention comprises a compound of Formula I, or a salt thereof, wherein $R_1$ is H.

Another particular embodiment of the invention comprises a compound of Formula I, or a salt thereof, wherein $R_1$ is selected from the group consisting of H and a $C_1-C_{10}$ saturated or unsaturated, straight or branched, cyclic or acyclic, chiral or achiral hydrocarbyl group, wherein optionally one or two carbon atoms of the hydrocarbyl group is replaced by $-N(-R_1)-$, $-O-$ or $-S-$.

Another particular embodiment of the invention comprises a compound of Formula I, or a salt thereof, wherein $R_2$ is selected from the group consisting of H and a $C_1-C_{10}$ saturated or unsaturated, straight or branched, cyclic or acyclic, chiral or achiral hydrocarbyl group, wherein optionally at least one carbon atom of the hydrocarbyl group is replaced by $-N(-R_1)-$, $-O-$ or $-S-$.

Another particular embodiment of the invention comprises a compound of Formula I, or a salt thereof, wherein $R_2$ is selected from the group consisting of H and a $C_1-C_{10}$ saturated or unsaturated, straight or branched, acyclic, chiral or achiral hydrocarbyl group, wherein optionally at least one carbon atom of the hydrocarbyl group is replaced by $-N(-R_1)-$, $-O-$ or $-S-$.

Another particular embodiment of the invention comprises a compound of Formula I, or a salt thereof, wherein $R_2$ is selected from the group consisting of H and a $C_1-C_{10}$ saturated, straight or branched, acyclic, chiral or achiral hydrocarbyl group, wherein optionally at least one carbon atom of the hydrocarbyl group is replaced by $-N(-R_1)-$, $-O-$ or $-S-$.

Another particular embodiment of the invention comprises a compound of Formula I, or a salt thereof, wherein $R_2$ is H.

Another particular embodiment of the invention comprises a compound of Formula I, or a salt thereof, wherein $R_2$ is selected from the group consisting of H and a $C_1-C_{10}$ saturated or unsaturated, straight or branched, cyclic or acyclic, chiral or achiral hydrocarbyl group, wherein optionally one or two carbon atoms of the hydrocarbyl group is replaced by $-N(-R_1)-$, $-O-$ or $-S-$.

Another particular embodiment of the invention comprises a compound of Formula I, or a salt thereof, wherein $R_3$ is selected from the group consisting of H; a $C_1-C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—; and a $C_1$-$C_{10}$ saturated or unsaturated, straight or branched, cyclic, chiral or achiral hydrocarbyl group.

Another particular embodiment of the invention comprises a compound of Formula I, or a salt thereof, wherein $R_3$ is selected from the group consisting of H; and a $C_1$-$C_{10}$ saturated or unsaturated, straight or branched, cyclic, chiral or achiral hydrocarbyl group.

Another particular embodiment of the invention comprises a compound of Formula I, or a salt thereof, wherein $R_3$ is selected from the group consisting of H; and a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—.

Another particular embodiment of the invention comprises a compound of Formula I, or a salt thereof, wherein $R_3$ is H.

Another particular embodiment of the invention comprises a compound of Formula I, or a salt thereof, wherein $R_3$ is selected from the group consisting of H; a $C_1$-$C_{10}$ saturated or unsaturated, straight or branched, acyclic, chiral or achiral hydrocarbyl group, wherein optionally one or two carbon atoms of the hydrocarbyl group is replaced by —N(—$R_1$)—, —O— or —S—; and a $C_1$-$C_{10}$ saturated or unsaturated, straight or branched, cyclic, chiral or achiral hydrocarbyl group.

Another particular embodiment of the invention comprises a compound of Formula I, or a salt thereof, wherein $R_4$ is selected from the group consisting of H; a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—; and a $C_1$-$C_{10}$ saturated or unsaturated, straight or branched, cyclic, chiral or achiral hydrocarbyl group.

Another particular embodiment of the invention comprises a compound of Formula I, or a salt thereof, wherein $R_4$ is selected from the group consisting of H; and a $C_1$-$C_{10}$ saturated or unsaturated, straight or branched, cyclic, chiral or achiral hydrocarbyl group.

Another particular embodiment of the invention comprises a compound of Formula I, or a salt thereof, wherein $R_4$ is selected from the group consisting of H; and a $C_1$-$C_{10}$ saturated or unsaturated, straight or branched, cyclic, chiral or achiral hydrocarbyl group, wherein optionally at least one carbon atom of the hydrocarbyl group is replaced by —N(—$R_1$)—, —O— or —S—.

Another particular embodiment of the invention comprises a compound of Formula I, or a salt thereof, wherein $R_4$ is H.

Another particular embodiment of the invention comprises a compound of Formula I, or a salt thereof, wherein $R_4$ is selected from the group consisting of H; a $C_1$-$C_{10}$ saturated or unsaturated, straight or branched, acyclic, chiral or achiral hydrocarbyl group, wherein optionally one or two carbon atoms of the hydrocarbyl group is replaced by —N(—$R_1$)—, —O— or —S—; and a $C_1$-$C_{10}$ saturated or unsaturated, straight or branched, cyclic, chiral or achiral hydrocarbyl group.

Another particular embodiment of the invention comprises a compound of Formula I, or a salt thereof, wherein $R_3$ and $R_4$ may combine to form a saturated or unsaturated carbocyclic ring with from 3 to 4 carbon atoms, wherein one or more carbon atoms is optionally replaced with —N(—$R_1$)— or —S— to form a heterocycle, or $R_3$ and $R_4$ may combine to form a saturated or unsaturated carbocyclic ring with from 5 to 6 carbon atoms, wherein one or more carbon atoms is optionally replaced with —N(—$R_1$)—, —O—, or —S—.

Another particular embodiment of the invention comprises a compound of Formula I, or a salt thereof, wherein $R_3$ and $R_4$ may combine to form a saturated or unsaturated carbocyclic ring with from 3 to 4 carbon atoms, wherein one or more carbon atoms is optionally replaced with —N(—$R_1$)— or —S— to form a heterocycle. In a sub-embodiment, one or two carbon atoms is optionally replaced with —N(—$R_1$)— or —S— to form a heterocycle.

Another particular embodiment of the invention comprises a compound of Formula I, or a salt thereof, wherein $R_3$ and $R_4$ may combine to form a saturated or unsaturated carbocyclic ring with from 5 to 6 carbon atoms, wherein one or more carbon atoms is optionally replaced with —N(—$R_1$)—, —O—, or —S—.

Another particular embodiment of the invention comprises a compound of Formula I, or a salt thereof, wherein $R_4$ and $Q_2$ combine to form a carbocyclic ring.

Another particular embodiment of the invention comprises a compound of Formula I, or a salt thereof, wherein $R_5$ is selected from the group consisting of H; halo; and a $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_3$) dialkyl amino, or acylamino.

Another particular embodiment of the invention comprises a compound of Formula I, or a salt thereof, wherein $R_5$ is H.

Another particular embodiment of the invention comprises a compound of Formula I, or a salt thereof, wherein $R_5$ is halo.

Another particular embodiment of the invention comprises a compound of Formula I, or a salt thereof, wherein $R_5$ is a $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_3$)dialkyl amino, or acylamino.

Another particular embodiment of the invention comprises a compound of Formula I, or a salt thereof, wherein $R_5$ is a $C_1$-$C_{10}$ saturated or unsaturated, straight or branched, cyclic or acyclic, chiral or achiral hydrocarbyl group.

Another particular embodiment of the invention comprises a compound of Formula I, or a salt thereof, wherein $R_5$ is a $C_1$-$C_{10}$ saturated or unsaturated, straight or branched, cyclic or acyclic, chiral or achiral hydrocarbyl group substituted with halogen.

Another particular embodiment of the invention comprises a compound of Formula I, or a salt thereof, wherein $R_5$ is a ($C_1$-$C_5$)heterocyclyl ring containing a nitrogen atom.

Another particular embodiment of the invention comprises a compound of Formula I, or a salt thereof, wherein $R_6$ is selected from the group consisting of H; halo; and $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_3$) dialkyl amino, or acylamino.

Another particular embodiment of the invention comprises a compound of Formula I, or a salt thereof, wherein $R_6$ is H.

Another particular embodiment of the invention comprises a compound of Formula I, or a salt thereof, wherein $R_6$ is halo.

Another particular embodiment of the invention comprises a compound of Formula I, or a salt thereof, wherein $R_6$ is a $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_3$)dialkyl amino, or acylamino.

Another particular embodiment of the invention comprises a compound of Formula I, or a salt thereof, wherein $R_6$ is a $C_1$-$C_{10}$ saturated or unsaturated, straight or branched, cyclic or acyclic, chiral or achiral hydrocarbyl group.

Another particular embodiment of the invention comprises a compound of Formula I, or a salt thereof, wherein $R_6$ is a $C_1$-$C_{10}$ saturated or unsaturated, straight or branched, cyclic or acyclic, chiral or achiral hydrocarbyl group substituted with halogen.

Another particular embodiment of the invention comprises a compound of Formula I, or a salt thereof, wherein $R_6$ is a ($C_1$-$C_5$)heterocyclyl ring containing on nitrogen atom.

Another particular embodiment of the invention comprises a compound of Formula I, or a salt thereof, wherein $R_5$ and $R_6$ may combine to form a saturated or unsaturated carbocyclic ring with from 3 to 6 carbon atoms, wherein one or more carbon atoms is optionally replaced with —N(—$R_1$)—, —O—, or —S—. In a sub-embodiment, one or two carbon atoms is optionally replaced with —N(—$R_1$)— or —S— to form a heterocycle Another particular embodiment of the invention comprises a compound of Formula I, or a salt thereof, wherein $R_5$ and $R_6$ may combine to form a saturated or unsaturated carbocyclic ring with from 3 to 6 carbon atoms.

Another particular embodiment of the invention comprises a compound of Formula I, or a salt thereof, wherein $R_7$ is selected from the group consisting of H; and a $C_1$-$C_{10}$ saturated or unsaturated, straight or branched, cyclic or acyclic, chiral or achiral hydrocarbyl group; and an inorganic cation or an organic cation, to form a salt.

Another particular embodiment of the invention comprises a compound of Formula I, or a salt thereof, wherein $R_7$ is H.

Another particular embodiment of the invention comprises a compound of Formula I, or a salt thereof, wherein $R_7$ is a $C_1$-$C_{10}$ saturated or unsaturated, straight or branched, cyclic or acyclic, chiral or achiral hydrocarbyl group.

Another particular embodiment of the invention comprises a compound of Formula I, or a salt thereof, wherein $R_7$ is an inorganic cation, to form a salt.

Another particular embodiment of the invention comprises a compound of Formula I, or a salt thereof, wherein $R_7$ is $Na^+$, to form a salt.

Another particular embodiment of the invention comprises a compound of Formula I, or a salt thereof, wherein $R_7$ is an organic cation, to form a salt.

Another particular embodiment of the invention comprises a compound of Formula I, or a salt thereof, wherein $R_8$ is H.

Another particular embodiment of the invention comprises a compound of Formula I, or a salt thereof, wherein $R_8$ is ($C_1$-$C_7$) hydrocarbyl.

Another particular embodiment of the invention comprises a compound of Formula I, or a salt thereof, wherein $R_9$ is —$(CH_2)_m$—C(—$R_5$)(—$R_6$)—$(CH_2)_n$—$COOR_7$.

Another particular embodiment of the invention comprises a compound of Formula I, or a salt thereof, wherein $R_9$ is —$(CH_2)_m$—C(—$R_5$)(—$R_6$)—$(CH_2)_n$—$COOR_7$ and z is 1.

Another particular embodiment of the invention comprises a compound of Formula I, or a salt thereof, wherein m is 0, 1, or 2.

Another particular embodiment of the invention comprises a compound of Formula I, or a salt thereof, wherein n is 0, 1, or 2.

Another particular embodiment of the invention comprises a compound of Formula I, or a salt thereof, wherein z is 1 or 2.

Another particular embodiment of the invention comprises a compound of Formula I, or a salt thereof, if $Q_1$ is substituted with hydroxy or alkoxy, then $Q_2$ cannot be substituted by bromo in the 2-position.

Another particular embodiment of the invention comprises a compound of Formula I, or a salt thereof, if X is —S—, —S(=O)—, or —S(=O)$_2$—, then Y is —N(—$R_1$)—.

In one aspect, the invention is a compound of Formula I, or a salt thereof:

$$Q_2\text{-}X\text{—}Y\text{—}CHR_3\text{—}CHR_4\text{-}Q_1 \qquad (I)$$

wherein:

$Q_1$ is selected from the group consisting of substituted or unsubstituted aryl and substituted or unsubstituted heteroaryl, with up to 5 substituents selected from the group consisting of:

chloro; bromo; nitro; —$NR_{10}R_{11}$; aroylamino; cyano; carboxy; carboxamido; trifluoromethyl; —O—$R_{10}$; [—N($R_1$)—$(CH_2)_m$—C(—$R_5$)(—$R_6$)—$(CH_2)_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$Q_2$ is selected from the group consisting of substituted or unsubstituted aryl and substituted or unsubstituted heteroaryl, with up to 5 substituents selected from the group consisting of:

chloro; nitro; —$NR_{10}R_{11}$; aroylamino; cyano; carboxy; carboxamido; trifluoromethyl; —O—$SO_2$—OH; —O—P(=O)(O$R_8$)$_2$; [—N(—$R_9$)—$(CH_2)_m$—C(—$R_5$)(—$R_6$)—$(CH_2)_n$—$COOR_7$]$_z$; and a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—;

wherein at least one of $Q_1$ and $Q_2$ is substituted;

X is selected from the group consisting of —S—, —S(=O)—, —S(=O)$_2$—, —CH($R_2$)—, —C(=O)—, and —N(—$R_1$)—;

Y is selected from the group consisting of —N(—$R_1$)—, —C(=O)—, —S—, —S(=O)— and —S(=O)$_2$—;

$R_1$ and $R_2$ are each independently selected from the group consisting of H and $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$R_3$ and $R_4$ are each independently selected from the group consisting of H; a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—;

and a $C_1$-$C_{10}$ saturated or unsaturated, straight or branched, cyclic, chiral or achiral hydrocarbyl group;

or $R_3$ and $R_4$ may combine to form a saturated or unsaturated carbocyclic ring with from 3 to 4 carbon atoms, wherein one or more carbon atoms is optionally replaced with —N(—$R_1$)— or —S— to form a heterocycle, or $R_3$ and $R_4$ may combine to form a saturated or unsaturated carbocyclic ring with from 5 to 6 carbon atoms, wherein one or more carbon atoms is optionally replaced with —N(—$R_1$)—, —O—, or —S—;

or $R_4$ and $Q_2$ may combine to form a carbocyclic ring;

$R_5$ and $R_6$ are each independently selected from the group consisting of H; halo; and a $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_6$) alkyl, ($C_1$-$C_6$) dialkyl amino, or acylamino;

or $R_5$ and $R_6$ may combine to form a saturated or unsaturated carbocyclic ring with from 3 to 6 carbon atoms, wherein one or more carbon atoms is optionally replaced with —N(—$R_1$)—, —O—, or —S—;

$R_7$ is selected from the group consisting of H; and a $C_1$-$C_{10}$ saturated or unsaturated, straight or branched, cyclic or acyclic, chiral or achiral hydrocarbyl group; and an inorganic cation or an organic cation, to form a salt;

$R_8$ is each independently selected from the group consisting of H and ($C_1$-$C_7$) hydrocarbyl;

$R_9$ is selected from the group consisting of H and —(CH$_2$)$_m$—C(—$R_5$)(—$R_6$)—(CH$_2$)$_n$—COOR$_7$;

$R_{10}$ is selected from the group consisting of H, branched or unbranched ($C_1$-$C_6$)alkyl, and ($C_2$-$C_8$)acyl;

$R_{11}$ is selected from the group consisting of H, branched or unbranched ($C_1$-$C_6$)alkyl, and ($C_2$-$C_8$)acyl;

m and n are each independently 0-2;

z is 1-2; and provided that if X is —S—, —S(=O)—, or —S(=O)$_2$—, then Y is —N(—$R_1$)—.

In one aspect, the invention is a compound of Formula I, or a salt thereof:

$$Q_2\text{-X—Y—CHR}_3\text{—CHR}_4\text{-Q}_1 \qquad (I)$$

wherein:

$Q_1$ is selected from the group consisting of substituted or unsubstituted aryl and substituted or unsubstituted heteroaryl, with up to 5 substituents selected from the group consisting of:

nitro; —NR$_{10}$R$_{11}$; aroylamino; cyano; carboxy; carboxamido; trifluoromethyl; —O—R$_{10}$; [—N(R$_1$)—(CH$_2$)$_m$—C(—R$_5$)(—R$_6$)—(CH$_2$)$_n$—COOR$_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$Q_2$ is selected from the group consisting of substituted or unsubstituted aryl and substituted or unsubstituted heteroaryl, with up to 5 substituents selected from the group consisting of:

nitro; —NR$_{10}$R$_{11}$; aroylamino; cyano; carboxy; carboxamido; trifluoromethyl; —O—SO$_2$—OH; —O—P(=O)(OR$_8$)$_2$; —O—R$_{10}$; [—N(—R$_9$)—(CH$_2$)$_m$—C(—R$_5$)(—R$_6$)—(CH$_2$)$_n$—COOR$_7$]$_z$; and a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—;

wherein at least one of $Q_1$ and $Q_2$ is substituted;

X is selected from the group consisting of: —S—, —S(=O)—, —S(=O)$_2$—, —CH(R$_2$)—, —C(=O)—, and —N(—R$_1$)—;

Y is selected from the group consisting of: —N(—R$_1$)—, and —C(=O)—;

$R_1$ and $R_2$ are each independently selected from the group consisting of H and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;

$R_3$ and $R_4$ are each independently selected from the group consisting of H; a $C_1$-$C_{10}$ saturated or unsaturated, straight or branched, acyclic, chiral or achiral hydrocarbyl group, wherein optionally at least one carbon atom of the hydrocarbyl group is replaced by —N(—$R_1$)—, —O— or —S—; and a $C_1$-$C_{10}$ saturated or unsaturated, straight or branched, cyclic, chiral or achiral hydrocarbyl group;

or $R_3$ and $R_4$ may combine to form a saturated or unsaturated carbocyclic ring with from 3 to 4 carbon atoms, wherein one or more carbon atoms is optionally replaced with —N(—$R_1$)— or —S— to form a heterocycle, or $R_3$ and $R_4$ may combine to form a saturated or unsaturated carbocyclic ring with from 5 to 6 carbon atoms, wherein one or more carbon atoms is optionally replaced with —N(—$R_1$)—, —O—, or —S—;

or $R_4$ and $Q_2$ may combine to form a carbocyclic ring;

$R_5$ and $R_6$ are each independently selected from the group consisting of H; halo; and a $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_6$) alkyl, ($C_1$-$C_6$) dialkyl amino, or acylamino;

or $R_5$ and $R_6$ may combine to form a saturated or unsaturated carbocyclic ring with from 3 to 6 carbon atoms, wherein one or more carbon atoms is optionally replaced with —N(—$R_1$)—, —O—, or —S—;

$R_7$ is selected from the group consisting of H; and $C_1$-$C_{10}$ saturated or unsaturated, straight or branched, cyclic or acyclic, chiral or achiral hydrocarbyl group; and an inorganic cation or an organic cation, to form a salt;

$R_8$ are each independently selected from the group consisting of H and ($C_1$-$C_7$) hydrocarbyl;

$R_9$ is selected from the group consisting of H and —(CH$_2$)$_m$—C(—R$_5$)(—R$_6$)—(CH$_2$)$_n$—COOR$_7$;

$R_{10}$ is selected from the group consisting of H, branched or unbranched ($C_1$-$C_6$)alkyl, and ($C_2$-$C_8$)acyl;

$R_{11}$ is selected from the group consisting of H, branched or unbranched ($C_1$-$C_6$)alkyl, and ($C_2$-$C_8$)acyl;

m and n are each independently 0-2; and z is 1-2.

In one aspect, the invention is a compound of Formula I, or a salt thereof, wherein:

$Q_1$ is a substituted phenyl with up to 5 substituents selected from the group consisting of fluoro; ($C_1$-$C_3$)alkoxy; and carboxy;

Q₂ is a substituted phenyl with up to 5 substituents selected from the group consisting of chloro; —NR$_{10}$R$_{11}$; carboxy; —O—R$_{10}$; and [—N(—R$_9$)—(CH$_2$)$_m$—C(—R$_5$)(—R$_6$)—(CH$_2$)$_n$—COOR$_7$]$_z$;

wherein at least one of Q$_1$ and Q$_2$ is substituted;

X is selected from the group consisting of —CH(R$_2$)— and —N(—R$_1$—)—;

Y is selected from the group consisting of —C(=O)— and —S(=O)$_2$—;

R$_1$ is H;

R$_2$ is H;

R$_3$ and R$_4$ are each H;

R$_5$ and R$_6$ are each independently selected from the group consisting of H; a C$_1$-C$_{10}$ saturated or unsaturated, straight or branched, cyclic or acyclic, chiral or achiral hydrocarbyl group, optionally substituted with bromo, chloro, or a nitrogen atom;

R$_7$ is selected from the group consisting of: H; and a C$_1$-C$_{10}$ saturated or unsaturated, straight or branched, cyclic or acyclic, chiral or achiral hydrocarbyl group; and an inorganic cation or an organic cation, to form a salt;

R$_8$ is selected from the group consisting of H and (C$_1$-C$_7$) hydrocarbyl;

R$_9$ is selected from the group consisting of H and —(CH$_2$)$_m$—C(—R$_5$)(—R$_6$)—(CH$_2$)$_n$—COOR$_7$;

m and n are each independently 0-2;

z is 1-2.

In preferred embodiments of the preceding aspect of the invention, Q$_1$ and Q$_2$ are defined as follows. Q$_1$ is phenyl substituted in at least the 4-position with fluoro, (C$_1$-C$_3$) alkoxy or carboxy. In some embodiments, the 4-position substituent is (C$_1$-C$_3$)alkoxy. In some embodiments, the phenyl is substituted at the 2-, 4- and 6-positions with (C$_1$-C$_3$)alkoxy, most preferably, methoxy. Q$_2$ is phenyl substituted in at least the 4-position with chloro; —NR$_{10}$R$_{11}$; carboxy; —O—R$_{10}$; and [—N(—R$_9$)—(CH$_2$)$_m$—C(—R$_5$)(—R$_6$)—(CH$_2$)$_n$—COOR$_7$]$_z$. In some embodiments, the 4-position substituent is selected from NR$_{10}$R$_{11}$, [—N(—R$_9$)—(CH$_2$)$_m$—C(—R$_5$)(—R$_6$)—(CH$_2$)$_n$—COOR$_7$]$_z$ and —O—R$_{10}$, with preferred [—N(—R$_9$)—(CH$_2$)$_m$—C(—R$_5$)(—R$_6$)—(CH$_2$)$_n$—COOR$_7$]$_z$ groups comprising —NHCH$_2$COOH and —NHCH$_2$COOCH$_3$ and preferred —O—R$_{10}$ groups comprising —OH and (C$_1$-C$_3$)alkoxy, most preferably, methoxy. In some embodiments, Q$_2$ is a di-substituted phenyl substituted at the 4-position with NR$_{10}$R$_{11}$, —O—R$_{10}$ or [—N(—R$_9$)—(CH$_2$)$_m$—C(—R$_5$)(—R$_6$)—(CH$_2$)$_n$—COOR$_7$]$_z$ and at the 3-position with NR$_{10}$R$_{11}$, carboxy, —O—R$_{10}$ or [—N(—R$_9$)—(CH$_2$)$_m$—C(—R$_5$)(—R$_6$)—(CH$_2$)$_n$—COOR$_7$]$_z$. In particular embodiments of said 3-,4-disubstituted phenyl, the 4-position substituent is —O—R$_{10}$ and the 3-position substituent is NR$_{10}$R$_{11}$, —O—R$_{10}$ or [—N(—R$_9$)—(CH$_2$)$_m$—C(—R$_5$)(—R$_6$)—(CH$_2$)$_n$—COOR$_7$]$_z$.

In one aspect, the compound of Formula I is:
4-chlorobenzyl-4-fluorophenethylsulfane;
1-chloro-4-(((4-fluorophenethyl) sulfonyl)methyl)benzene;
2-methoxy-5-(((2,4,6-trimethoxyphenethyl)sulfonyl) methyl)aniline;
2-methoxy-5-(((2,4,6-trimethoxyphenethyl)sulfonyl) methyl)phenol;
4-(2-((4-chlorobenzyl) sulfonyl)ethyl)benzoic acid;
N-(3-amino-4-methoxyphenyl)-3-(2,4,6-trimethoxyphenyl) propanamide;
methyl 2-((2-methoxy-5-(((2,4,6-trimethoxyphenethyl)sulfonyl)methyl)phenyl)amino)acetate;
dimethyl 2,2'-((2-methoxy-5-(((2,4,6-trimethoxyphenethyl) sulfonyl)methyl)phenyl)azanediyl)diacetate;
2-((2-methoxy-5-(((2,4,6-trimethoxyphenethyl)sulfonyl) methyl)phenyl)amino)acetic acid;
2-((2-methoxy-5-(((2,4,6-trimethoxyphenethyl)sulfonyl) methyl)phenyl)amino)propanoic acid;
2-((2-methoxy-5-(((2,4,6-trimethoxyphenethyl)sulfonyl) methyl)phenyl)amino)-2-methylpropanoic acid;
2-((2-methoxy-5-(((2,4,6-trimethoxyphenethyl)sulfonyl) methyl)phenyl)amino)-2-phenylacetic acid;
2-(4-fluorophenyl)-2-((2-methoxy-5-(((2,4,6-trimethoxyphenethyl)sulfonyl)methyl)phenyl)amino)acetic acid;
2-(4-chlorophenyl)-2-((2-methoxy-5-(((2,4,6-trimethoxyphenethyl)sulfonyl)methyl)phenyl)amino)acetic acid;
2-((2-methoxy-5-(((2,4,6-trimethoxyphenethyl)sulfonyl) methyl)phenyl)amino)-3-phenylpropanoic acid;
2-cyclopropyl-2-((2-methoxy-5-(((2,4,6-trimethoxyphenethyl)sulfonyl)methyl)phenyl)amino)acetic acid;
2-((2-methoxy-5-(((2,4,6-trimethoxyphenethyl)sulfonyl) methyl)phenyl)amino)-2-(1H-pyrrol-3-yl)acetic acid;
N-(3-amino-4-methoxyphenyl)-2-(2,4,6-trimethoxyphenyl) ethanesulfonamide;
1,3,5-trimethoxy-2-(2-((4-methoxybenzyl)sulfonyl)ethyl) benzene;
N-(4-methoxyphenethyl)-4-methylbenzenesulfonamide;
4-methoxy-N-(4-methoxyphenethyl)-3-nitrobenzenesulfonamide;
3-amino-4-methoxy-N-(4-methoxyphenethyl)benzenesulfonamide;
4-methoxy-3-nitro-N-(2,4,6-trimethoxyphenethyl)benzenesulfonamide;
3-amino-4-methoxy-N-(2,4,6-trimethoxyphenethyl)benzenesulfonamide;
4-methoxy-N-(4-methoxyphenethyl)benzenesulfonamide;
4-methoxy-N-(2,4,6-trimethoxyphenethyl)benzenesulfonamide;
4-methyl-N-(2,4,6-trimethoxyphenethyl)benzenesulfonamide;
4-methoxy-N-(2,4,6-trimethoxyphenethyl)benzamide;
4-methoxy-N-(4-methoxyphenethyl)benzamide;
4-methoxy-N-(4-methoxyphenethyl)-3-nitrobenzamide;
3-amino-4-methoxy-N-(4-methoxyphenethyl)benzamide;
4-methoxy-3-nitro-N-(2,4,6-trimethoxyphenethyl)benzamide;
3-amino-4-methoxy-N-(2,4,6-trimethoxyphenethyl)benzamide;
2-(4-methoxyphenyl)-N-(2,4,6-trimethoxyphenyl)ethanesulfonamide;
4-(((3,4-dimethoxyphenethyl)thio)methyl)-2-methoxyphenol;
4-(((3,4-dimethoxyphenethyl)sulfonyl)methyl)-2-methoxyphenol;
N-(4-methoxyphenethyl)-4-methylbenzenesulfonamide;
4-methoxy-N-(4-methoxyphenethyl)-3-nitrobenzenesulfonamide;
3-amino-4-methoxy-N-(4-methoxyphenethyl)benzenesulfonamide;
4-methoxy-3-nitro-N-(2,4,6-trimethoxyphenethyl)benzenesulfonamide;
3-amino-4-methoxy-N-(2,4,6-trimethoxyphenethyl)benzenesulfonamide;
4-methoxy-N-(4-methoxyphenethyl)benzenesulfonamide;
4-methoxy-N-(2,4,6-trimethoxyphenethyl)benzenesulfonamide;
4-methyl-N-(2,4,6-trimethoxyphenethyl)benzenesulfonamide;
4-methoxy-N-(2,4,6-trimethoxyphenethyl)benzamide;
4-methoxy-N-(4-methoxyphenethyl)benzamide;
4-methoxy-N-(4-methoxyphenethyl)-3-nitrobenzamide;

3-amino-4-methoxy-N-(4-methoxyphenethyl)benzamide;
4-methoxy-3-nitro-N-(2,4,6-trimethoxyphenethyl)benzamide;
3-amino-4-methoxy-N-(2,4,6-trimethoxyphenethyl)benzamide;
2-(4-methoxyphenyl)-N-(2,4,6-trimethoxyphenyl)ethanesulfonamide;
4-(((3,4-dimethoxyphenethyl)thio)methyl)-2-methoxyphenol;
4-(((3,4-dimethoxyphenethyl)sulfonyl)methyl)-2-methoxyphenol;
or a salt thereof.

Particularly preferred compounds include the following and their pharmaceutically acceptable salts:
2-((2-methoxy-5-(((2,4,6-trimethoxyphenethyl)sulfonyl)methyl)phenyl)amino) acetic acid;
4-(2-((4-chlorobenzyl)sulfonyl)ethyl)benzoic acid;
3-amino-4-methoxy-N-(2,4,6-trimethoxyphenethyl)benzenesulfonamide; and
3-amino-4-methoxy-N-(2,4,6-trimethoxyphenethyl)benzamide.

Preferred slats include, for example, sodium salts. A preferred sodium salt is sodium 2-((2-methoxy-5-(((2,4,6-trimethoxyphenethyl)sulfonyl)methyl)phenyl)amino)acetate.

III. METHODS FOR PREPARING COMPOUNDS OF THE INVENTION AND INTERMEDIATES USEFUL IN THE SYNTHESIS OF COMPOUNDS OF THE INVENTION

There are provided processes for preparing compounds according to Formula I, intermediates that are useful in the preparation of such compounds, and processes for preparing such intermediates.

Processes for producing embodiments of Formula I are disclosed, wherein the embodiments of Formula I are identified as Formula Ia, Formula Ib, Formula Ic, Formula Id, Formula Ie, Formula If, Formula Ig, Formula Ih, and Formula Ii. In the formulas and schemes that follow, unless otherwise indicated, $Q_1$, $Q_2$, X, Y, $R_1$, $R_2$, $R_3$, $R_4$, $R_5$, $R_6$, $R_7$, $R_8$, $R_9$, m, n, and z are as defined above for Formula I.

In an embodiment, a process for preparing a compound of Formula Ia or a salt thereof is provided, wherein Formula Ia is a sulfide compound of Formula I. The process comprises:
reacting a compound of Formula AA with a compound of Formula BB to produce a compound of Formula Ia:

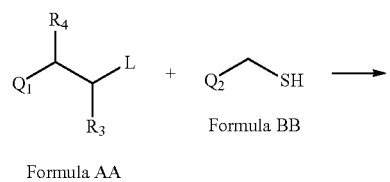

Formula AA    Formula BB in a reaction mixture, wherein $Q_1$, $Q_2$, $R_3$, and $R_4$ are as defined above; L is a leaving group selected from the group consisting of Cl, Br, and I; and optionally, isolating from the reaction mixture the compound of Formula Ia or a salt thereof.

In an embodiment, the aforesaid reaction takes place in the presence of a base.

In an embodiment, a process for providing a compound of Formula Ib or a salt thereof is provided, wherein Formula Ib is a sulfone compound of Formula I. The process comprises:
oxidizing a compound of Formula Ia to produce a compound of Formula Ib,

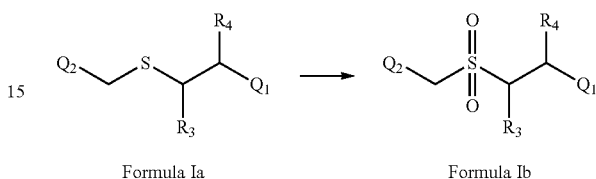

Formula Ia            Formula Ib in a reaction mixture, wherein $Q_1$, $Q_2$, $R_3$, and $R_4$ are as defined above; and optionally, isolating from the reaction mixture the compound of Formula Ib or a salt thereof.

In an embodiment, the aforesaid reaction takes place in the presence of an acid and a peroxide.

In an embodiment, a process for providing a compound of Formula Ic or a salt thereof is provided, wherein Formula Ic is a sulfonamide compound of Formula I. The process comprises a reaction step of:
reacting a compound of Formula CC with a compound of Formula DD to produce a compound of Formula Ic,

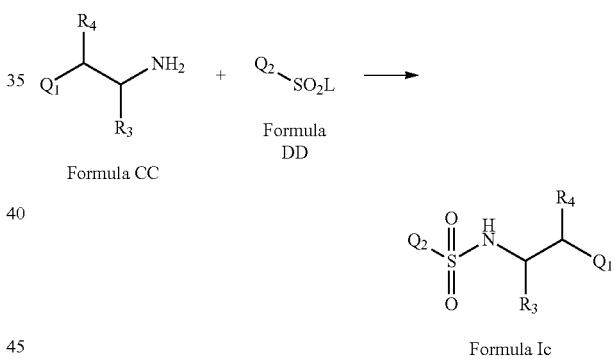

Formula CC    Formula DD

Formula Ic in a reaction mixture, wherein $Q_1$, $Q_2$, $R_3$, and $R_4$ are as defined above; and optionally, isolating from the reaction mixture the compound of Formula Ic or a salt thereof.

In an embodiment, the aforesaid reaction takes place in the presence of a base.

In an embodiment, a process for providing a compound of Formula Id or a salt thereof is provided, wherein Formula Id is a sulfonamide compound of Formula I. The process comprises a reaction step of:
reacting a compound of Formula EE with a compound of Formula FF to produce a compound of Formula Id,

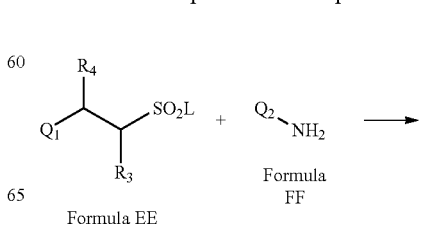

Formula EE    Formula FF

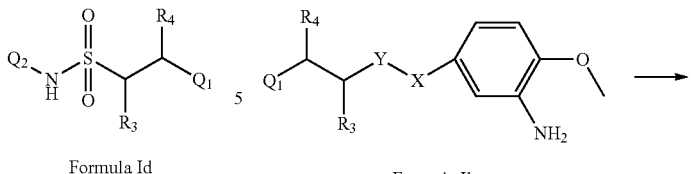

Formula Id in a reaction mixture, wherein $Q_1$, $Q_2$, $R_3$, and $R_4$ are as defined above; and optionally, isolating from the reaction mixture the compound of Formula Id or a salt thereof.

In an embodiment, a process for providing a compound of Formula If or a salt thereof is provided, wherein Formula If is a subset of Formula I. The process comprises a reaction step of:

reducing a compound of Formula Ie to produce a compound of Formula If,

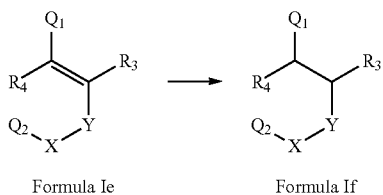

Formula Ie          Formula If in a reaction mixture, wherein X, Y, $Q_1$, $Q_2$, $R_3$, and $R_4$ are as defined above; and optionally, isolating from the reaction mixture the compound of Formula If or a salt thereof In an embodiment, the aforesaid reaction takes place in the presence of a platinum, rhodium, raney nickel, or palladium catalyst, preferably a palladium catalyst.

In an embodiment, a process for providing a compound of Formula Ig or a salt thereof is provided, wherein Formula Ig is an amide compound of Formula I. The process comprises a reaction step of:

reacting a compound of Formula GG with a compound of Formula HH to produce a compound of Formula Ig,

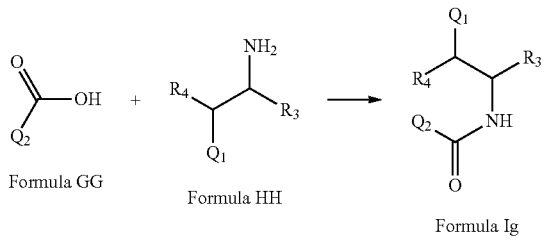

Formula GG     Formula HH     Formula Ig in a reaction mixture, wherein $Q_1$, $Q_2$, $R_3$, and $R_4$ are as defined above; and optionally, isolating from the reaction mixture the compound of Formula Ig or a salt thereof.

In an embodiment, the aforesaid reaction takes place in the presence of a carbodiimide.

In an embodiment, a process for providing Formula Ii or a salt thereof is provided, wherein Formula Ii is a subset of compound of Formula I. The process comprises a reaction step of:

reacting a compound of Formula Ih to produce a compound of Formula Ii,

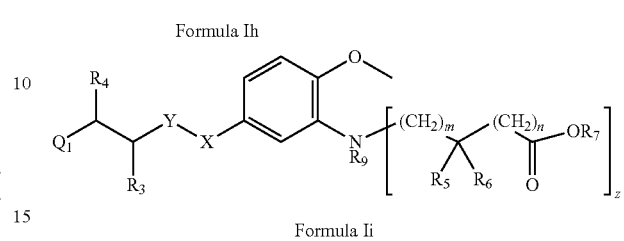

Formula Ih

Formula Ii in a reaction mixture, wherein X, Y, $Q_1$, $R_3$, $R_4$, $R_5$, $R_6$, $R_7$, and $R_9$, m, n, and z are as defined above, and optionally, wherein $R_7$ is not H, then a second reaction can be performed to covert the $R_7$ into H. From the forgoing reaction(s) the compound of Formula Ii or a salt thereof may be isolated from the reaction mixture.

In the following paragraphs, a more detailed discussion of the processes for producing embodiments of Formula I is provided, along with preferred embodiments and reaction details. The embodiments of Formula I are identified as Formula Ia, Formula Ib, Formula Ic, Formula Id, Formula Ie, Formula If, Formula Ig, Formula Ih, and Formula Ii.

In an embodiment, a detailed process for preparing Formula Ia or a salt thereof is further provided, wherein Formula Ia is a sulfide compound of Formula I.

Scheme Ia

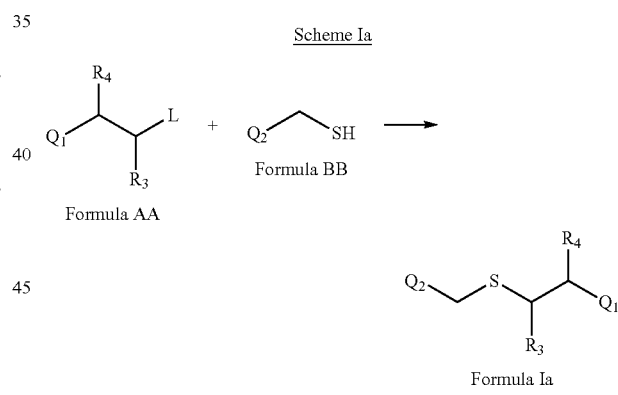

Formula AA     Formula BB

Formula Ia

In Scheme Ia, $Q_1$, $Q_2$, $R_3$, and $R_4$ are as defined above; and L is a leaving group selected from the group consisting of: Cl, Br, and I.

Particular embodiments of the process in Scheme Ia include those wherein:

$R_3$ is H;

$R_4$ is H;

$Q_1$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$R_{10}$; [—N(—$R_1$)—$(CH_2)_m$—C(—$R_5$)(—$R_6$)—$(CH_2)_n$—COOR$_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—; and Q$_2$ is selected from the group consisting of substituted or unsubstituted aryl and substituted or unsubstituted heteroaryl, with up to 5 substituents selected from the group consisting of fluoro; chloro; bromo; nitro; —NR$_{10}$R$_{11}$; aroylamino; cyano; carboxy; carboxamido; trifluoromethyl; —O—SO$_2$—OH; —O—P(=O)(OR$_8$)$_2$; —O—R$_{10}$; [—N(—R$_9$)—(CH$_2$)$_m$—C(—R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—.

In another embodiment of Scheme Ia, R$_3$ is H; R$_4$ is H; Q$_1$ is F; and Q$_2$ is Cl.

The reaction in Scheme Ia can be achieved in the presence of base catalysts or reagents. Preferably, the base is at least one of K$_2$CO$_3$ or NaOH. The reaction in Scheme Ia is preferably carried out in an appropriate solvent, preferably methanol. The reactions in Scheme Ia are typically carried out at a temperature between 20° C. and the reflux temperature of the solvent, which is typically about 50-100° C. The temperature during the reaction in Scheme Ia is preferably room temperature for 3 hours. The reaction preferably takes place under an inert atmosphere, such as nitrogen gas.

In an embodiment, a detailed process for preparing Formula Ib or a salt thereof is further provided, wherein Formula Ib is a sulfone compound of Formula I.

Scheme Ib

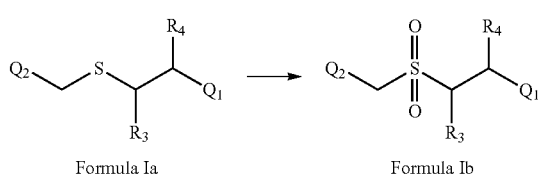

Formula Ia → Formula Ib

In Scheme Ib, Q$_1$, Q$_2$, R$_3$, and R$_4$ are as defined above.

Particular embodiments of the process in Scheme Ib include those wherein:

R$_3$ is H; R$_4$ is H; and Q$_1$ is selected from the group consisting of substituted or unsubstituted aryl and substituted or unsubstituted heteroaryl, with up to 5 substituents selected from the group consisting of:

fluoro; chloro; bromo; nitro; —NR$_{10}$R$_{11}$; aroylamino; cyano; carboxy; carboxamido; trifluoromethyl; [—N(—R$_1$)—(CH$_2$)$_m$—C(—R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—; and Q$_2$ is selected from the group consisting of substituted or unsubstituted aryl and substituted or unsubstituted heteroaryl, with up to 5 substituents selected from the group consisting of:

fluoro; chloro; bromo; nitro; —NR$_{10}$R$_{11}$; aroylamino; cyano; carboxy; carboxamido; trifluoromethyl; —O—SO$_2$—OH; —O—P(=O)(OR$_8$)$_2$; [—N(—R$_9$)—(CH$_2$)$_m$—C(—R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—.

In another embodiment of Scheme Ib, R$_3$ is H; R$_4$ is H; Q$_1$ is F; and Q$_2$ is Cl.

The reaction in Scheme Ib can proceed in the presence of an acid, such a glacial acetic acid, and a peroxide, such as hydrogen peroxide. The reaction in Scheme Ib is preferably carried out in an appropriate solvent, but can be carried out in a liquid acid without the addition of a solvent. The reactions in Scheme Ib are typically carried out at under ambient conditions. The reaction in Scheme Ib is preferably carried out at room temperature for 24 hours under an inert atmosphere.

In another embodiment, the peroxide is meta-chloroperoxybenzoic acid (mCPBA), which may selectively oxidize a sulfide to form sulfoxide as shown in Scheme Ib-2.

Scheme Ib-2

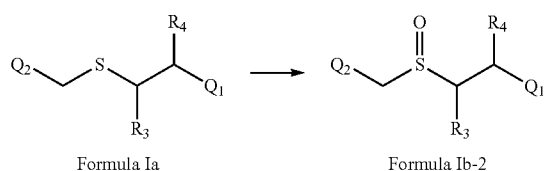

Formula Ia → Formula Ib-2

In Scheme Ib, Q$_1$, Q$_2$, R$_3$, and R$_4$ are as defined above.

In an embodiment, a detailed process for preparing Formula Ic or a salt thereof is further provided, wherein Formula Ic is a sulfonamide compound of Formula I.

Scheme Ic

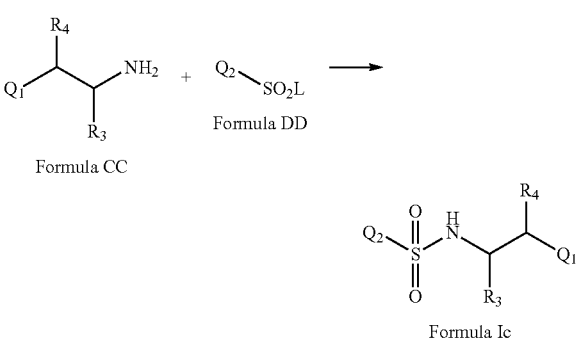

Formula CC + Formula DD →

Formula Ic

In Scheme Ic, Q$_1$, Q$_2$, R$_3$, and R$_4$ are as defined above, and L is a leaving group selected from the group consisting of Cl, Br, and I.

Particular embodiments of the process in Scheme Ic include those wherein:

R$_3$ is H; R$_4$ is H; and Q$_1$ is selected from the group consisting of substituted or unsubstituted aryl and substituted or unsubstituted heteroaryl, with up to 5 substituents selected from the group consisting of:

fluoro; chloro; bromo; nitro; —NR$_{10}$R$_{11}$; aroylamino; cyano; carboxy; carboxamido; trifluoromethyl; —O—R$_{10}$; [—N(—R$_1$)—(CH$_2$)$_m$—C(—R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—; and $Q_2$ is selected from the group consisting of substituted or unsubstituted aryl and substituted or unsubstituted heteroaryl, with up to 5 substituents selected from the group consisting of fluoro; chloro; bromo; nitro; —$NR_{10}R_{11}$; aroylamino; cyano; carboxy; carboxamido; trifluoromethyl; —O—$SO_2$—OH; —O—P(=O)($OR_8$)$_2$; —O—$R_{10}$; [—N(—$R_9$)—($CH_2$)$_m$—C(—$R_5$)(—$R_6$)—($CH_2$)$_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—.

The reaction in Scheme Ic can be achieved in the presence of base catalysts or reagents. Preferably, the base is at least one of pyridine or $Et_3N$. The reaction in Scheme Ic is preferably carried out in an appropriate solvent, preferably anhydrous acetone or methylene chloride. The reactions in Scheme Ic are typically carried out at a temperature between room temperature and the reflux temperature of the solvent, which is typically about 50-100° C. The temperature during the reaction in Scheme Ic is preferably room temperature for 3 hours. The reaction preferably takes place under an inert atmosphere, such as nitrogen gas.

In an embodiment, a detailed process for preparing Formula Id or a salt thereof is further provided, wherein Formula Id is a sulfonamide compound of Formula I.

Scheme Id

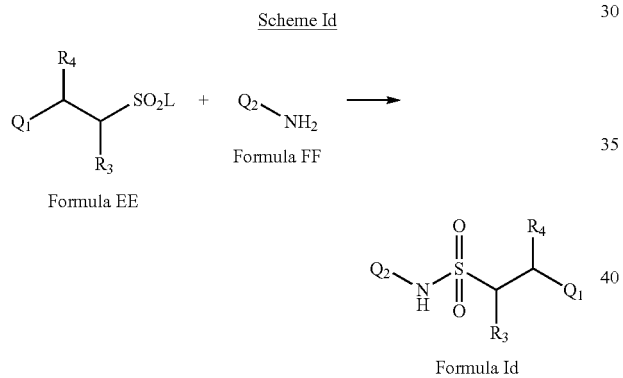

Formula EE

Formula FF

Formula Id

In Scheme Id, $Q_1$, $Q_2$, $R_3$, and $R_4$ are as defined above and L is a leaving group selected from the group consisting of: Cl, Br, and I.

Particular embodiments of the process in Scheme Id include those wherein:

$R_3$ is H; $R_4$ is H; and $Q_1$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$R_{10}$; [—N($R_1$)—($CH_2$)$_m$—C(—$R_5$)(—$R_6$)—($CH_2$)$_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—; and $Q_2$ is selected from the group consisting of substituted or unsubstituted aryl and substituted or unsubstituted heteroaryl, with up to 5 substituents selected from the group consisting of fluoro; chloro; bromo; nitro; —$NR_{10}R_{11}$; aroylamino; cyano; carboxy; carboxamido; trifluoromethyl; —O—$SO_2$—OH; —O—P(=O)($OR_8$)$_2$; —O—$R_{10}$; [—N(—$R_9$)—($CH_2$)$_m$—C(—$R_5$)(—$R_6$)—($CH_2$)$_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—.

The reaction in Scheme Id can be achieved in the presence of base catalysts or reagents. Preferably, the base is at least one of pyridine, $K_2CO_3$ or NaOH. The reaction in Scheme Id is preferably carried out in an appropriate solvent, preferably anhydrous acetone. The reactions in Scheme Id are typically carried out at a temperature between 20° C. and the reflux temperature of the solvent, which is typically about 50-100° C. The temperature during the reaction in Scheme Id is preferably room temperature for 3 hours. The reaction preferably takes place under an inert atmosphere, such as nitrogen gas.

In an embodiment, a detailed process for preparing Formula Ie or a salt thereof is further provided, wherein Formula Ie is a subset of a compound of Formula I.

Scheme Ie

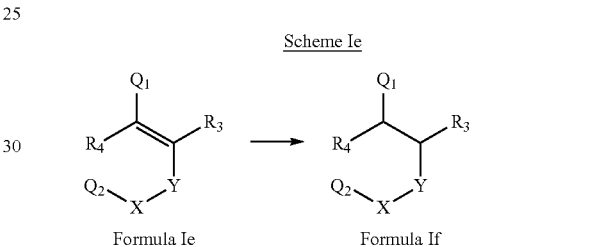

Formula Ie

Formula If

In Scheme Ie, X, Y, $Q_1$, $Q_2$, $R_3$, and $R_4$ are as defined above.

Particular embodiments of the process in Scheme Ie include those wherein:

X is selected from the group consisting of —CH($R_2$)— and —N(—$R_1$)—; Y is selected from the group consisting of —S(=O)$_2$— and —C(=O)—; $R_1$ is H; $R_2$ is H; $R_3$ is H; $R_4$ is H; and $Q_1$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$R_{10}$; [—N($R_1$)—($CH_2$)$_m$—C(—$R_5$)(—$R_6$)—($CH_2$)$_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—; and $Q_2$ is selected from the group consisting of substituted or unsubstituted aryl and substituted or unsubstituted heteroaryl, with up to 5 substituents selected from the group consisting of:

fluoro; chloro; bromo; nitro; —$NR_{10}R_{11}$; aroylamino; cyano; carboxy; carboxamido; trifluoromethyl; —O—$SO_2$—OH; —O—P(=O)($OR_8$)$_2$; —O—$R_{10}$; [—N(—$R_9$)—($CH_2$)$_m$—C(—$R_5$)(—$R_6$)—($CH_2$)$_n$—$COOR_7$]$_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—.

In another embodiment of Scheme Ie, X is —CH(R$_2$)—; Y is —S(=O)$_2$—; R$_2$ is H; R$_3$ is H; R$_4$ is H; Q$_1$ is substituted aryl, with up to 5 (C$_1$-C$_3$)alkoxy substituents; and Q$_2$ is aryl, with up to 5 substituents selected from the group consisting of: (C$_1$-C$_3$)alkoxy, and —NR$_{10}$R$_{11}$.

In another embodiment of Scheme Ie, X is —CH(R$_2$)—; Y is —S(=O)$_2$—; R$_2$ is H; R$_3$ is H; R$_4$ is H; Q$_1$ is substituted aryl, with up to 5 (C$_1$-C$_3$)alkoxy substituents; and Q$_2$ is aryl, with up to 5 substituents selected from the group consisting of: (C$_1$-C$_3$)alkoxy, [—N(—R$_9$)—(CH$_2$)$_m$—C(—R$_5$)(—R$_6$)—(CH$_2$)$_n$—COOR$_7$]$_z$; R$_9$ is H; and z is 1.

In another embodiment of Scheme Ie, X is —CH(R$_2$)—; Y is —S(=O)$_2$—; R$_2$ is H; R$_3$ is H; R$_4$ is H; Q$_1$ is substituted aryl, with up to 5 (C$_1$-C$_3$)alkoxy substituents; and Q$_2$ is aryl, with up to 5 substituents selected from the group consisting of: (C$_1$-C$_3$)alkoxy, and hydroxy.

In another embodiment of Scheme Ie, X is —CH(R$_2$)—; Y is —S(=O)$_2$—; R$_2$ is H; R$_3$ is H; R$_4$ is H; Q$_1$ is substituted aryl, with up to 5 and —(C=O)—OH substituents; and Q$_2$ is aryl, with up to 5 chloro substituents.

In another embodiment of Scheme Ie, X is —N(—R$_1$)—; Y is —C(=O)—; R$_1$ is H; R$_3$ is H; R$_4$ is H; Q$_1$ is substituted aryl, with up to 5 (C$_1$-C$_3$)alkoxy substituents; and Q$_2$ is aryl, with up to 5 substituents selected from the group consisting of: (C$_1$-C$_3$)alkoxy, and amino.

The reaction in Scheme Ie can take place in the presence of catalyst comprising a platinum, rhodium, raney nickel, or palladium. Preferably, the catalyst is a palladium catalyst, including 10% palladium on carbon (Pd—C) and a hydrogen atmosphere. Preferably, the reaction takes place in one or more suitable solvents, such as methanol and MeOH/EtOAc (1:1). The reaction can take place at 1 atmosphere over 5-10% Pd—C. Preferably, the aforementioned reaction can take place in ≤48 h.

In an embodiment, a detailed process for preparing Formula If or a salt thereof is further provided, wherein Formula If is an amide compound of Formula I.

Scheme If

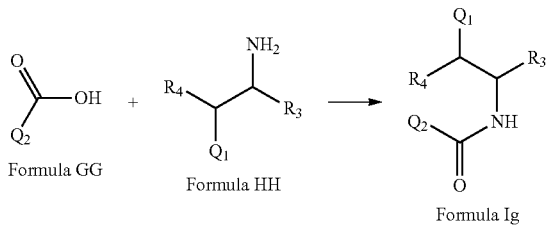

Formula GG    Formula HH    Formula Ig

In Scheme If, Q$_1$, Q$_2$, R$_3$, and R$_4$ are as defined above.

Particular embodiments of the process in Scheme If include those wherein:

R$_3$ is H; R$_4$ is H; X is —C(=O)—; Y is —N(—R$_1$)—; Q$_1$ is selected from the group consisting of substituted or unsubstituted aryl and substituted or unsubstituted heteroaryl, with up to 5 substituents selected from the group consisting of:

fluoro; chloro; bromo; nitro; —NR$_{10}$R$_{11}$; aroylamino; cyano; carboxy; carboxamido; trifluoromethyl; [—N(—R$_1$)—(CH$_2$)$_m$—C(R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—; and Q$_2$ is selected from the group consisting of substituted or unsubstituted aryl and substituted or unsubstituted heteroaryl, with up to 5 substituents selected from the group consisting of:

fluoro; chloro; bromo; nitro; —NR$_{10}$R$_{11}$; aroylamino; cyano; carboxy; carboxamido; trifluoromethyl; —O—SO$_2$—OH; —O—P(=O)(OR$_8$)$_2$; —O—R$_{10}$; [—N(—R$_9$)—(CH$_2$)$_m$—C(—R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—.

The reaction in Scheme If can be achieved in the presence of base, such as 4-Dimethylaminopyridine (DMAP), and a coupling agent, such as a carbodiimide. Preferably, the carbodiimide is 1-ethyl-3-(3-dimethylaminopropyl) carbodiimide. The reaction in Scheme If is preferably carried out in an appropriate solvent, preferably dimethylformamide (DMF). The reactions in Scheme If are typically carried out at room temperature for ≤24 hours.

In an embodiment, a detailed process for preparing Formula Ig or a salt thereof is further provided, wherein Formula Ig is a subset of a compound of Formula I.

Scheme Ig

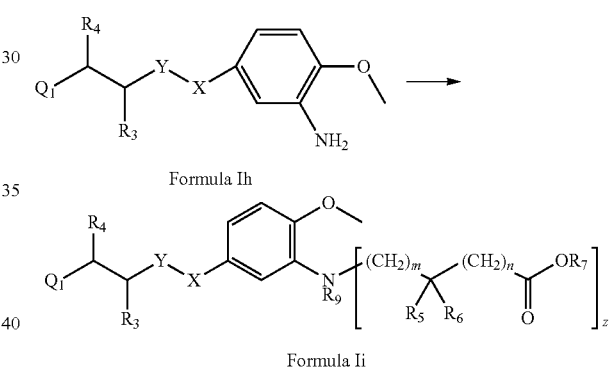

Formula Ih

Formula Ii

In Scheme Ig, X, Y, Q$_1$, R$_3$, R$_4$, R$_5$, R$_6$, R$_7$, R$_9$, m, n, and z are as defined above.

Particular embodiments of the process in Scheme Ig include those wherein:

X is selected from the group consisting of —S—, —S(=O)—, —S(=O)$_2$—, —CH(R$_2$)—, and —N(—R$_1$)—; Y is selected from the group consisting of: —N(—R$_1$)—, —C(=O)—, —S—, and —S(=O)$_2$—; R$_1$ is H, R$_3$ is H, R$_4$ is H; and Q$_1$ is selected from the group consisting of substituted or unsubstituted aryl and substituted or unsubstituted heteroaryl, with up to 5 substituents selected from the group consisting of:

fluoro; chloro; bromo; nitro; —NR$_{10}$R$_{11}$; aroylamino; cyano; carboxy; carboxamido; trifluoromethyl; —O—R$_{10}$; [—N(—R$_1$)—(CH$_2$)$_m$—C(—R$_5$)(—R$_6$)—(CH$_2$)$_n$—COOR$_7$]$_z$; and a C$_1$-C$_{10}$ saturated or unsaturated, straight or branched, cyclic or acyclic, chiral or achiral hydrocarbyl group, wherein optionally at least one carbon atom of the hydrocarbyl group is replaced by —N(—R$_1$)—, —O— or —S—;

R$_5$ and R$_6$ are each independently selected from the group consisting of: H; halo; and a C$_1$-C$_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_6$) alkyl, ($C_1$-$C_6$) dialkyl amino, or acylamino; and $R_7$ is selected from the group consisting of: H; a $C_1$-$C_{10}$ saturated or unsaturated, straight or branched, cyclic or acyclic, chiral or achiral hydrocarbyl group; and an inorganic cation to form a salt, provided that if X is —S—, —S(=O)—, or —S(=O)$_2$—, then Y is —N(—$R_1$)—.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is H, $R_6$ is H, $R_7$ is methyl; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is H, $R_6$ is H, $R_7$ is methyl; $R_9$ is [—(CH$_2$)$_m$—C(—$R_5$)(—$R_6$)—(CH$_2$)$_n$—COO$R_7$]; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is methyl; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is methyl; $R_6$ is methyl; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is phenyl; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is 4-F-phenyl-; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is 4-Cl-phenyl-; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is —CH$_2$-phenyl; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is —CH$_2$-phenyl; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is cyclopropyl; $R_6$ is H; $R_7$ H; $R_9$ is H; and m is 0, n is 0, and z is 1.

In another embodiment of Scheme Ig, X is —CH($R_2$)—; Y is —S(=O)$_2$—; $R_3$ is H; $R_4$ is H; $Q_1$ is substituted aryl, with up to 5 ($C_1$-$C_3$)alkoxy substituents; and $R_5$ is H; $R_6$ is H; $R_7$ is Na$^+$; $R_9$ is H; and m is 0, n is 0, and z is 1.

A process of making a compound of Formula Ia or salt thereof, which is a subset of Formula I, is provided

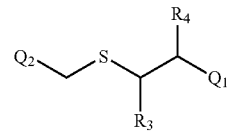

Formula Ia

The process comprises a reaction step of:
reacting a compound of Formula AA;

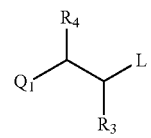

Formula AA with a compound of Formula BB;

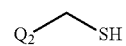

Formula BB to produce a compound of Formula Ia in a reaction mixture, and optionally isolating the compound of Formula Ia from the reaction mixture, wherein $Q_1$, $Q_2$, $R_3$, and $R_4$ are as defined above, and L is a leaving group selected from the group consisting of: Cl, Br, and I.

In an embodiment, the aforesaid reaction takes place in the presence of a base.

A process of making a compound of Formula Ib or salt thereof, which is a subset of Formula I, is provided.

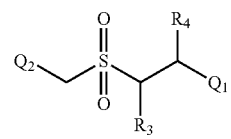

Formula Ib

The process comprises a reaction step of:
oxidizing a compound of Formula Ia:

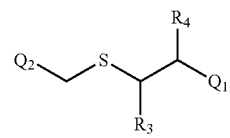

Formula Ia to produce a compound of Formula Ib in a reaction mixture, and optionally isolating compound Formula Ib from the reaction mixture, wherein $Q_1$, $Q_2$, $R_3$, and $R_4$ are as defined above.

In an embodiment, the aforesaid reaction takes place in the presence of an acid and a peroxide.

A process of making a compound of Formula Ic or salt thereof, which is a subset of Formula I, is provided.

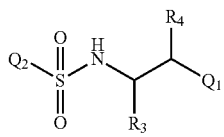

The process comprises a reaction step of:
reacting a compound of Formula CC;

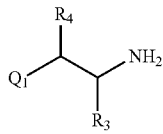

Formula CC with a compound of Formula DD;

Formula DD to produce a compound of Formula Ic in a reaction mixture, and optionally isolating the compound of Formula Ic from the reaction mixture, wherein $Q_1$, $Q_2$, $R_3$, and $R_4$ are as defined in above, and L is a leaving group selected from the group consisting of: Cl, Br, and I.

In an embodiment, the aforesaid reaction takes place in the presence of a base.

A process of making a compound of Formula Id or salt thereof, which is a subset of Formula I, is provided.

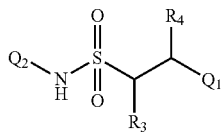

Formula Id

The process comprises a reaction step of:
reacting a compound of Formula EE:

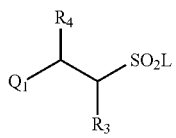

Formula EE with a compound of Formula FF;

Formula FF to produce a compound of Formula Id in a reaction mixture, and optionally isolating the compound of Formula Id from the reaction mixture, wherein $Q_1$, $Q_2$, $R_3$, and $R_4$ are as defined above, and L is a leaving group selected from the group consisting of: Cl, Br, and I.

In an embodiment, the aforesaid reaction takes place in the presence of a base.

A process of making a compound of Formula If or salt thereof, which is a subset of Formula I, is provided.

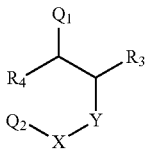

Formula If

The process comprises a reaction step of:
reducing a compound of Formula Ie;

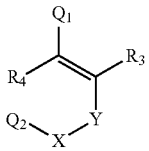

Formula Ie to produce a compound of Formula If in a reaction mixture, and optionally isolating the compound of Formula Ie from the reaction mixture, wherein X, Y, $Q_1$, $Q_2$, $R_3$, and $R_4$ are as defined above.

In an embodiment, the aforesaid reaction takes place in the presence of a palladium catalyst.

A process of making a compound of Formula Ig or salt thereof, which is a subset of Formula I, is provided.

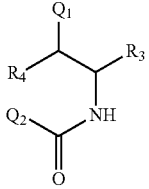

Formula Ig

The process comprises:
reacting a compound of Formula GG;

Formula GG with a compound of Formula HH;

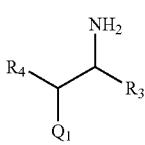

Formula HH to produce a compound of Formula Ig in a reaction mixture, and optionally isolating the compound of Formula Ig from the reaction mixture, wherein $Q_1$, $Q_2$, $R_3$, and $R_4$ are as defined above.

In an embodiment, the aforesaid reaction takes place in the presence of a carbodiimide.

A process of making a compound of Formula Ii or salt thereof, which is a subset of Formula I, is provided.

Formula Ii

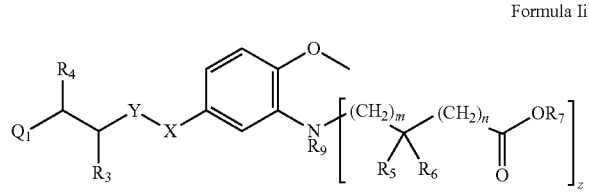

The process comprises a reaction step comprising:
reacting a compound of Formula Ih:

Formula Ih

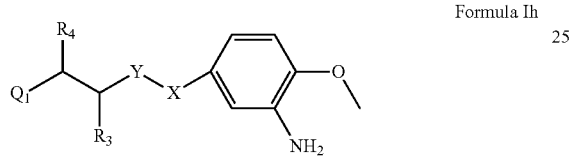

to produce a compound of Formula Ii in a reaction mixture, and optionally isolating the compound Formula Ii from the reaction mixture, wherein X, Y, $Q_1$, $R_3$, $R_4$, $R_5$, $R_6$, $R_7$, $R_9$, m, n, and z are as defined above.

In an embodiment, the aforesaid reaction takes place in the presence of a base and a compound L-$CH_2$—(C=O)—O—($C_1$-$C_6$-alkyl), wherein L is a halogen.

IV. TREATMENT OF CELLULAR PROLIFERATIVE DISORDERS USING COMPOUNDS OF THE INVENTION

According to another embodiment of the invention, a method of treating an individual suffering from a cellular proliferative disorder, particularly cancer, is provided, comprising administering to said individual an effective amount of at least one compound according to Formula I, or a pharmaceutically acceptable salt thereof, either alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to Formula I, or a pharmaceutically acceptable salt thereof, either alone, or in combination with a pharmaceutically acceptable carrier.

The compounds according to the invention may be administered to individuals (mammals, including animals and humans) afflicted with a cellular proliferative disorder such as cancer, malignant and benign tumors, blood vessel proliferative disorders, autoimmune disorders, and fibrotic disorders. In a particular embodiment of the invention, the individual treated is a human.

The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR)

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

In an aspect of the method, a method of treating an individual suffering from a cellular proliferative disorder, comprises administering to the individual an effective amount of at least one compound, or a pharmaceutically acceptable salt thereof, according to Formula I.

In a particular aspect of the method, the compound of Formula I is selected from the group consisting of 4-(2-((4-chlorobenzyl)sulfonyl)ethyl)benzoic acid, and pharmaceutically acceptable salts thereof; and 2-((2-methoxy-5-(((2,4,6-trimethoxyphenethyl)sulfonyl)methyl)phenyl)amino) acetic acid, and pharmaceutically acceptable salts thereof.

A preferable embodiment of a sodium salt of a compound of Formula I for the method of treatment is sodium 2-((2-methoxy-5-(((2,4,6-trimethoxyphenethyl)sulfonyl)methyl)phenyl)amino)acetate.

In a further aspect of the method, the cellular proliferative disorder is selected from the group consisting of: cancer, malignant and benign tumors, blood vessel proliferative disorders, autoimmune disorders, and fibrotic disorders.

In a further aspect of the method, the cellular proliferative disorder is a cancer selected from the group consisting of ovarian cancer; cervical cancer; breast cancer; prostate cancer; testicular cancer, lung cancer, renal cancer; colorectal cancer; skin cancer; brain cancer; and leukemia.

In a further aspect of the method, the leukemia is selected from the group consisting of acute myeloid leukemia, chronic myeloid leukemia, acute lymphoid leukemia, and chronic lymphoid leukemia.

A method of inducing apoptosis of cancer cells in an individual afflicted with cancer, comprises administering to the individual an effective amount of at least one compound, or a pharmaceutically acceptable salt thereof, according to Formula I.

In another aspect, the invention is directed to the use of a compound according to Formula I or a salt thereof for therapy. In another aspect, the invention is directed to the use of a compound according to Formula I or a salt thereof for use in medicine.

In another aspect, the invention is directed to the use of a compound according to Formula I or a pharmaceutically acceptable salt thereof for treating an individual suffering from a cellular proliferative disorder.

In another aspect, the invention is directed to the use of a compound according to Formula I or a pharmaceutically acceptable salt thereof for treating an individual suffering from a cellular proliferative disorder, wherein the cellular proliferative disorder is selected from the group consisting of cancer, malignant and benign tumors, blood vessel proliferative disorders, autoimmune disorders, and fibrotic disorders.

In another aspect, the invention is directed to the use of a compound according to Formula I or a pharmaceutically acceptable salt thereof for treating an individual suffering from a cellular proliferative disorder, wherein the cellular proliferative disorder is a cancer selected from the group consisting of: ovarian cancer; cervical cancer; breast cancer; prostate cancer; testicular cancer, lung cancer, renal cancer; colorectal cancer; skin cancer; brain cancer; and leukemia.

In another aspect, the invention is directed to the use of a compound according to Formula I or a pharmaceutically acceptable salt thereof for treating an individual suffering from a cellular proliferative disorder, wherein the cellular proliferative disorder is a leukemia is selected from the group consisting of: acute myeloid leukemia, chronic myeloid leukemia, acute lymphoid leukemia, and chronic lymphoid leukemia.

Another aspect of the invention is directed to a compound of Formula I or a pharmaceutically acceptable salt thereof for treatment of a cellular proliferative disorder.

Another aspect of the invention is directed to a compound of Formula I or a pharmaceutically acceptable salt thereof for treatment of a cellular proliferative disorder wherein the cellular proliferative disorder is selected from the group consisting of cancer, malignant and benign tumors, blood vessel proliferative disorders, autoimmune disorders, and fibrotic disorders.

Another aspect of the invention is directed to a compound of Formula I or a pharmaceutically acceptable salt thereof for treatment of a cellular proliferative disorder wherein the cellular proliferative disorder is a cancer selected from the group consisting of: ovarian cancer; cervical cancer; breast cancer; prostate cancer; testicular cancer, lung cancer, renal cancer; colorectal cancer; skin cancer; brain cancer; and leukemia.

Another aspect of the invention is directed to a compound of Formula I or a pharmaceutically acceptable salt thereof for treatment of a cellular proliferative disorder, wherein the cellular proliferative disorder is a leukemia is selected from the group consisting of: acute myeloid leukemia, chronic myeloid leukemia, acute lymphoid leukemia, and chronic lymphoid leukemia.

V. SALTS OF COMPOUNDS ACCORDING TO THE INVENTION

The compounds of the present invention may take the form of salts when appropriately substituted with groups or atoms capable of forming salts. Such groups and atoms are well known to those of ordinary skill in the art of organic chemistry. The term "salts" embraces addition salts of free acids or free bases which are compounds of the invention. The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, pivalic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, tromethamine, meglumine (N-methylglucamine) and procaine. Examples of pharmaceutically unacceptable base addition salts include lithium salts and cyanate salts.

All of these salts may be prepared by conventional means from the corresponding compound according to Formula I by reacting, for example, the appropriate acid or base with the compound according to Formula I. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VI. PHARMACEUTICAL COMPOSITIONS

A pharmaceutical composition comprises a pharmaceutically acceptable carrier and a compound, or a pharmaceutically acceptable salt thereof, according to any of Formula I.

The compounds of the invention may be administered in the form of a pharmaceutical composition, in combination with a pharmaceutically acceptable carrier. The active ingredient or agent in such formulations (i.e. a compound of Formula I) may comprise from 0.1 to 99.99 weight percent of the formulation. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the cellular proliferative disorder, the aggressiveness of the cellular proliferative disorder, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VII. ROUTES OF ADMINISTRATION OF COMPOUNDS AND COMPOSITIONS OF THE INVENTION

The compounds of Formula I, including pharmaceutically acceptable salts thereof, may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

VIII. ISOMERISM IN COMPOUNDS OF THE INVENTION

A. Optical Isomerism

It will be understood that when or if compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example below, the Cahn-Ingold-Prelog ranking is A>B>C>D. The lowest ranking atom, D is oriented away from the viewer.

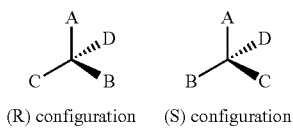

(R) configuration    (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound having the structure of Formula I, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

B. Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of Formula I.

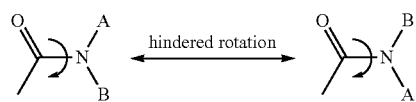

IX. EXAMPLES

The following non-limiting examples are provided to illustrate the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography, or HPLC may be used to determine the optimum reaction time. Products may be purified by conventional techniques that will vary, for example, according to the amount of side products produced and the physical properties of the compounds. On a laboratory scale, recrystallization from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al, *Experimental Organic Chemistry: Standard and Microscale*, by L. M. Harwood et al. ($2^{nd}$ Ed., Blackwell Scientific Publications, 1998), and Advanced Practical Organic Chemistry, by J. Leonard, et al. ($2^{nd}$ Edition, CRC Press 1994).

Scheme 1

General Procedures I-VI are used in preparing Compounds 1-7 in Scheme 1.

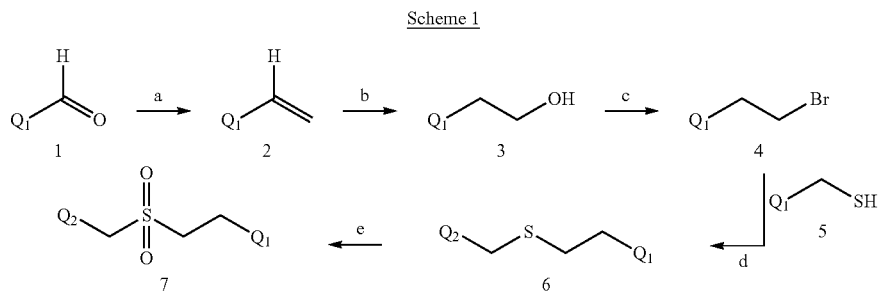

Non-limiting embodiments of reaction conditions for each step may include: a) $^+[Ph_3PCH_3]^-Br$, t-BuOK, THF, O° C.-r.t., 2.5 hours; b) i. 9-Borabicyclo(3.3.1)nonane, THF, O°-r.t., 18 hours; ii. $H_2O_2$, 3N NaOH, 3 hours; c) $CBr_4$, $PPh_3$, 2 hours; d) NaOH, MeOH, 2 hours; and e) $H_2O_2$, AcOH, 24 hours.

General Procedure I:

Preparation of Compound 2 of Scheme 1: Substituted Styrenes.

To the mixture of methyltriphenylphosphonium bromide (47.0 mmol) and potassium tert-butoxide (53.0 mmol), dry tetrahydrofuran ("THF") (36 mL) is added at room temperature under nitrogen. To the reaction mixture, an appropriate amount of substituted benzaldehyde 1 (45.0 mmol) is dissolved in dry THF (18 mL) and added dropwise for 90 min under cooling in an ice bath. Then the reaction is kept stirring for 60 min. The reaction mixture is poured into cold water, and the organic layer is separated. The aqueous mixture is extracted three times with diethyl ether. The combined organic layer is dried over anhydrous $MgSO_4$. After evaporation, the layer is poured into a large amount of n-hexane to precipitate triphenylphosphine oxide. After filtration, the filtrate is evaporated. The concentrated liquid is distilled under vacuum to give a colorless liquid of substituted styrene 2 (74-86%).

General Procedure II:

Preparation of Compound 3 of Scheme 1: Substituted 2-phenyethanols.

To an ice-cold solution of substituted styrene 2 (12.7 mmol) in THF (40 mL) is added 9-Borabicyclo(3.3.1) nonane ("9-BBN") (0.5 M in THF, 25 mmol). The reaction is conducted at ambient temperature for 18 h and quenched by addition of MeOH (40 mL). After 30 min of stirring, 3 N NaOH (40 mL, 120 mmol) and 35% $H_2O_2$ (75 mmol) are added slowly. The resulting mixture is stirred at room temperature for 3 hours and poured into $H_2O$. The product is extracted with ether twice. The combined organic layers are washed with brine, dried over $MgSO_4$, and concentrated to afford a residual oil, which is purified by chromatography on silica gel with hexane/EtOAc (from 5:1 to 1:2) to afford substituted 2-phenyethanols 3 (85-90%) as colorless solids.

General Procedure III

Preparation of Compound 4 of Scheme 1: Substituted (2-bromoethyl)benzenes.

To an ice-cold solution of 2-phenyethanols 3 (11.1 mmol) and $PPh_3$ (13.3 mmol) in $CH_2Cl_2$ (20 mL) is added $CBr_4$ (12.2 mmol). The mixture is stirred at room temperature for 2 hours and concentrated to afford a residual oil, which is purified by chromatography on silica gel with hexane/ EtOAc (10:1) to afford substituted (2-bromoethyl)benzenes 4 (80-94%).

General Procedure IV

Preparation of Compound 5 of Scheme 1: Substituted Phenylmethanethiols.

A solution of substituted benzylbromide (41 mmol) and thiourea (55 mmol) in 50 mL water is heated under reflux for 2 hours. The reaction mixture is cooled and stirred at room-temperature for 2 hours, and the solid is filtered, dried, and the resulting dried intermediate, isothiouronium salt, is used in next step without further purification. The yield of this reaction is 90%.

The above isothiouronium salt (10 g) is decomposed by boiling three times with ammonium hydroxide and hexane (100 mL, 15:85) followed by three times with ammonium hydroxide, ethyl acetate, and hexane (100 mL, 15:5:80). Concentration of the combined extracts provides crude substituted phenylmethanethiol 5, which is purified by silica gel flash column chromatography (hexane/ethylacetate, 4:1). The yield of this reaction is 25%.

General Procedure V

Preparation of Compound 6 of Scheme 1: Substituted benzyl (substituted phenethyl)sulfanes.

To a cooled solution of sodium hydroxide (100 mmol) in absolute methanol (50 mL), arylmethanethiol 5 (100 mmol) is added slowly and the reaction mixture is stirred for 5 min. An appropriate substituted (2-bromoethyl)benzene 4 (100 mmol) is added in portions to the contents of the flask, and the mixture is stirred for 2 h. After completion of the reaction (monitored by thin-layer chromatography ("TLC"), the contents of the flask are poured into crushed ice with stirring, filtered the compound formed, washed with ice-cold water and dried to get the compounds 6 of scheme 1 as white solids (82-95%).

General Procedure VI

Preparation of Compound 7 of Scheme 1: (2-(substituted benzylsulfonyl)ethyl) Substituted Benzenes.

To the substituted benzyl(substituted phenethyl)sulfanes 6 (50 mmol) in glacial acetic acid (100 mL) is added 30% hydrogen peroxide (60 mL) in portions at frequent intervals. Then the reaction mixture is kept at room temperature for 24 hours. The solid, if any formed, is separated by filtration, and the filtrate is poured onto crushed ice. The separated compound is filtered, washed with water, dried, and added to the first crop, if any. The total product on recrystallization from methanol affords pure (2-(substituted benzylsulfonyl)ethyl) substituted benzenes 7, (72-76%) as white solid.

Example 1

4-Chlorobenzyl-4-fluorophenethylsulfane

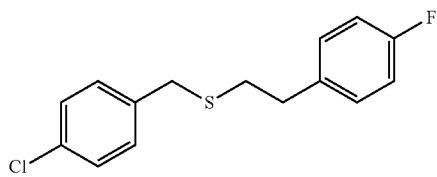 [SMILES: Fc1ccc(CCSCc2ccc(Cl)cc2)cc1]

The title compound was prepared according to Scheme 1. A solution of 0.01 mole sodium hydroxide in methanol 30 mL was taken in a 100 mL round-bottomed flask and cooled 10° C. To the cooled solution, 0.01 mole of 4-chlorobenzyl thiol was added slowly to the contents of the flask. A vigorous reaction occurred immediately. On completion of the addition and when the reaction was no longer exothermic, 1-(2-chloroethyl)-4-fluorobenzene (0.01 mole) was added portion wise, and the reaction mixture was stirred at room temperature for 3 h. The reaction was checked by TLC (thin layer chromatography) for completion. After completion, the reaction mixture was poured into crushed ice. The compound formed was filtered, washed with ice-cold water, and dried. The procedure according to General Procedure V produced the title compound with a yield of 90% and melting point 36-38° C.

Example 2

1-Chloro-4-(((4-fluorophenethyl)sulfonyl)methyl) benzene

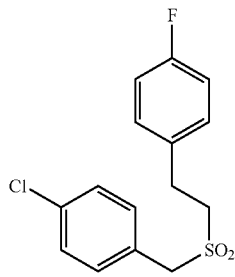 [SMILES: O=S(=O)(CCc1ccc(F)cc1)Cc1ccc(Cl)cc1]

The title compound was prepared according to Scheme 1. An ice-cold solution of 4-chlorobenzyl-4-fluorophenethyl-sulfane (4.0 g) in glacial acetic acid (25 mL) was added to a 100 mL round-bottomed flask. 30% hydrogen peroxide (8.0 mL) was added to the mixture at frequent intervals. Then, the reaction mixture was kept at room temperature for 24 h. The mixture was poured onto crushed ice. The solid formed was filtered, washed with ice-cold water, and dried. The procedure according to Reaction VI produced the title compound with a yield of 80% and a melting point of 142-144° C.

$^1$H NMR (CDCl$_3$, 300 MHz): δ 3.55-3.60 (m, 2H, CH$_2$), 3.75-3.82 (m, 2H, CH$_2$), 4.30 (s, 2H, CH$_2$), 6.92-7.10 (m, 6H, Ar—H), 7.15 (d, J=8.1 Hz, 1H, Ar—H).). HRMS: m/z calcd [M+H] 313.69. found 313.40.

Scheme 2

General Procedures VII-XI are Used to Prepare Compounds 1-5 of Scheme 2.

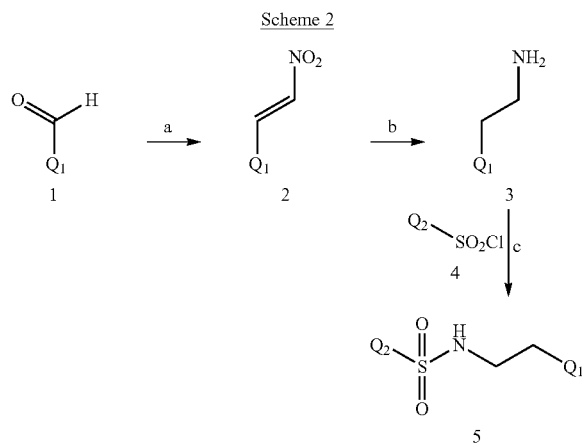

Scheme 2

Non-limiting embodiments of reaction conditions for each step may include: a) CH$_3$NO$_2$, NH$_4$OAC, AcOH, EtOH, reflux; b) LiAlH$_4$, Et$_2$O, THF; and c) anhydrous acetone/pyridine, overnight or CH$_2$Cl$_2$/Et$_3$N, rt.

General Procedure VII
Preparation of Compound 1 of Scheme 2: Substituted Benzaldehyde.

A 500 mL multi-necked flask is equipped with a reflux condenser, stirrer, a gas inlet, and thermometer. 0.425 mol of substituted benzene, 0.625 mol of zinc cyanide, and 200 mL of 1,1,2,2-tetrachloroethane, is placed in the flask and the mixture is stirred while a rapid stream of dry hydrogen chloride is passed through it until the zinc cyanide is decomposed. The flask is immersed in a bath of crushed ice, the inlet tube is removed and 197 g of finely ground, anhydrous aluminum chloride is added over a period of 10 minutes. The mixture is stirred very vigorously and removed from the ice bath after addition, and the passage of hydrogen chloride gas is resumed for 3.5 h, while heating the reaction mass to about 70° C. The temperature at 67-72° C. is maintained until the reaction is complete. After completion of the reaction, the reaction mixture is cooled and poured into a mixture of crushed ice and 50 mL of concentrated hydrochloric acid. The reaction mixture is allowed to stand overnight and then refluxed for 3 h. The reaction mixture is allowed to cool and separate into an organic layer and extract aqueous layer with tetrachloroethane. The organic layer is washed with 10% sodium carbonate solution and evaporated to get crude substituted benzaldehyde, which on purification results in pure substituted benzaldehyde 1. The yield is about 79%.

General Procedure VIII
Preparation of Compound 2 of Scheme 2: Substituted (E)-(2-nitrovinyl)benzenes.

A solution of (0.50 mol) of substituted benzaldehyde 1, (1.55 mol) of nitromethane, and (0.50 mol) of ammonium acetate in 400 mL glacial acetic acid is refluxed for 2 h and then poured into an ice-water mixture. This gives a solid, which is collected by filtration and recrystallized from ethanol to afforded pure substituted (E)-(2-nitrovinyl) benzenes 2, (80-82%).

General Procedure IX
Preparation of Compound 3 of Scheme 2: Substituted 2-phenylethanamines.

A solution of (0.421 mol) of substituted (E)-(2-nitrovinyl) benzenes 2 in 500 mL of THF is added slowly to a slurry of (0.782 mol) of LiAlH$_4$ in 400 mL of Et$_2$O under nitrogen atmosphere. After the addition is complete, the mixture is refluxed for 1.5 h and then 140 mL of 1N NaOH is added and the mixture is filtered. The solid is extracted with 200 mL of boiling THF. The THF extract and the filtrate are combined and concentrated under vacuum. The residue is dissolved in Et$_2$O, which is dried over K$_2$CO$_3$, and then concentrated to give crude substituted 2-phenylethanamines 3, which on purification gives 55% of the desired product.

General Procedure X
Preparation of Compound 4 of Scheme 2: Substituted Benzenesulfonyl Chloride.

A mixture of substituted benzene (1.09 mol) in chloroform (500 mL) is magnetically stirred at 0° C. while chlorosulphonic acid (3.44 mol) is added for 15 minutes under cooling and exclusion of moisture. The stirring is continued for 45 minutes at room temperature and the mixture is poured on to crushed ice. The product is extracted with chloroform, dried over anhydrous sodium sulphate, and freed from solvent in vacuo at 30° C. The residue is dissolved in warm pentane, and the solution is filtered and concentrated to ⅔ and upon standing. The substituted benzenesulfonyl chloride 4 is crystallized, filtered and washed with −30° C. chilled pentane, then dry under phosphorus pentoxide to provide an 86% yield.

General Procedure XI
Preparation of Compound 5 of Scheme 2: N-Substituted Phenethyl Substituted Benzenesulfonamides.

0.05 mol of substituted 2-phenylethanamine 3 is dissolve in a mixture of 40 mL of anhydrous acetone and 6 mL of dry pyridine. To the mixture, 0.05 mol of substituted benzenesulfonyl chloride 4 add is added. The reaction mixture is set aside overnight and the solid formed filtered to provide crude N-substituted phenethyl substituted benzenesulfonamides 5. Pure substituted phenethyl substituted benzenesulfonamides 5 are obtained upon on recrystallization result with a 55% yield.

Scheme 3

General Procedures XII-XIV are used to prepare compounds 1-3 of scheme 3:

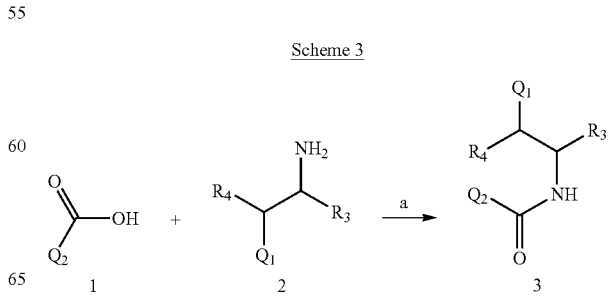

Scheme 3

Non-limiting embodiments of reaction conditions for each step may include: a) EDCI, DMAP, DMF, rt, 20 h.

General Procedure XII

Preparation of Compound 1 of Scheme 3: Substituted Benzoic Acids.

312.5 mL of water, 18.75 g of pure potassium permanganate, and 0.1 mol of substituted toluene are placed in a three necked flask. The mixture is stirred and refluxed gently until practically all the permanganate color has disappeared. At this point, 10 g of more potassium permanganate is added and the mixture is refluxed again until the permanganate color disappears, and the refluxing is stopped. Another 10 g potassium permanganate is added and the mixture is again refluxed until the permanganate color disappears. The unreacted substituted toluene is distilled away. The hot contents of the flask from the manganese dioxide are filtered with suction and washed twice with water. The filtrate is concentrated and 18.75 mL concentrated hydrochloric acid is added with stirring. The solid formed is filtered and washed with cold water and dry at 100° C. The yield is 68% substituted benzoic acids 1.

General Procedure XIII

Preparation of Compound 2 of Scheme 3: Substituted 2-phenylethanamines.

A solution of (0.50 mol) of substituted benzaldehyde, (1.55 mol) of nitromethane, and (0.50 mol) of ammonium acetate in 400 mL glacial acetic acid is refluxed for 2 h and then poured into an ice-water mixture. This gives a solid, which is collected by filtration and recrystallized from ethanol to afford pure substituted (E)-(2-nitrovinyl) benzenes 2 (80-82%).

A solution of (0.421 mol) of substituted (E)-(2-nitrovinyl) benzenes in 500 mL of THF is added slowly to a slurry of (0.782 mol) of LiAlH$_4$ in 400 mL of Et$_2$O under nitrogen atmosphere. After the addition is complete, the mixture is refluxed for 1.5 h and then 140 mL of lN NaOH is added. The mixture is filtered, and the solid is extracted with 200 mL of boiling THF. The THF extract and the filtrate are combined and concentrated under vacuum. The residue is dissolved in Et$_2$O, which is dried over K$_2$CO$_3$, and then concentrated to give crude 2, which on purification gives 55% of the desired product.

General Procedure XIV

Preparation of Compound 3 of Scheme 3: N-Substituted Phenethyl Substituted Benzamides.

Substituted benzoic acid 1 (1.0 mmol) and EDCI (1.0 mmol) (1-ethyl-3-(3'-dimethylaminopropyl)carbodiimide hydrochloride) are mixed in 10 mL of N,N-dimethylformamide (DMF). This mixture is stirred at room temperature for 1 h and then 4-dimethylaminopyridine (DMAP) (2.0 mmol) and substituted 2-phenylethanamine 2 (1.0 mmol) are added. The mixture is stirred at rt for 20 h. The reaction mixture is acidified with 10% HCl and extracted with ethyl acetate or chloroform. The organic phase is washed with 10% HCl, saturated sodium bicarbonate solution, and brine. The organic phase is dried over MgSO$_4$ and evaporated in vacuo. The crude compound is purified by column chromatography (Silica gel, Hexane/ethyl acetate or Methanol/chloroform) to obtain the pure product 3.

Scheme 4

General Procedures XV-XVIII are used to prepare Compounds 1-5 of Scheme 4.

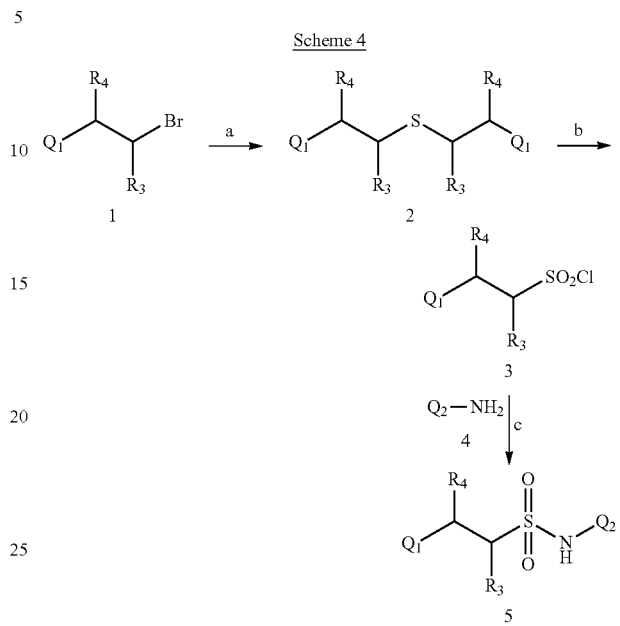

Non-limiting embodiments of reaction conditions for each step may include: a) Na$_2$S, EtOH, and 2 hours; b) iodosobenzene and hydrogen chloride-treated silica gel; and c) pyridine, anhydrous acetone.

General Procedure XV

Preparation of Compound 1 of Scheme 4: (2-bromoethyl) substituted benzenes.

Compound 1 of Scheme 4 can be prepared by following General Procedures I-III above.

General Procedure XVI

Preparation of Compound 2 of Scheme 4: Substituted Diphenethylsulfanes.

Sodium sulphide (0.5 mole) is placed in 500 mL ethanol. The mixture is heated on a water bath until the sulphide dissolves. 0.5 mole of finely powdered sulfur is added and the heating is continued until all the sulfur dissolves. A solution of 0.66 mole of substituted 2-bromoethylbenzenes prepared and added to 175 mL ethanol. To this mixture, the sodium disulphide solution is slowly added at such a rate that the reaction is under control. The mixture is heated on a water bath gently and then water is boiled vigorously for 2 hours. The reaction mixture is cooled, filtered, washed with ethanol, and dried to produce a substituted diphenethylsulfanes 2 with a yield: 68%.

General Procedure XVII

Preparation of Compound 3 of Scheme 4: Substituted 2-phenylethanesulfonyl chlorides.

The substituted diphenethylsulfanes 2 are pulverized with iodosobenzene and hydrogen chloride-treated silica gel (HCl-silica gel) to yield substituted-2-phenylethane sulfonyl chlorides 3 by simultaneously oxidation and chlorination.

General Procedure XVIII

Preparation of Compound 5 of Scheme 4: Substituted N,2-diphenylethane sulfonamides.

Substituted anilines 4 (0.05 mol) are dissolved in a mixture of 40 mL of anhydrous acetone and 6 mL of dry pyridine. 0.05 mol of substituted 2-phenylethanesulfonyl chlorides 3 is added. The reaction mixture is set aside overnight and the solid that forms is filtered to obtain crude 5, which on recrystallization result pure substituted N-2-diphenylethane sulfonamides for a yield of 55%.

Scheme 5

General Procedure XIX is used to prepare Compounds 1 and 2 of Scheme 5.

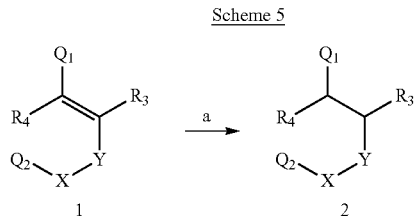

Non-limiting embodiments of reaction conditions for each step may include: 10% PD-C, H$_2$, EtOAc/MeOH, 24-48 hours.

General Procedure XIX

Reduction of unsaturated Compound 1 of Scheme 5 with 10% Pd—C/H$_2$ is carried out as follows. A solution of Compound 1 (1.5 mmol) in a mixture of MeOH/EtOAc (40 mL) is treated with wet 10% palladium on carbon (50 mg) then exposed to hydrogen atmosphere by using hydrogenation apparatus. After completion of the reaction (monitored by TLC), the reaction mixture is filtered through Celite, washed the Celite pad thoroughly with a mixture of methanol and chloroform (50%) and the filtrate evaporated under reduced pressure. The filtered solid is washed with ether and dried under vacuum to obtain pure Compound 2 of scheme 5.

Sulfones of Compound 1 [Y=—S(=O)$_2$—; X=—CH(—R$_2$)— or X=—S(=O)$_2$—; Y=—CH(—R$_2$)—] of Scheme 5 can be prepared as disclosed in U.S. Pat. Nos. 6,201,154; 6,359,013; 7,598,232; 6,762,207; 6,541,475; 6,486,210; and 7,161,031, which are incorporated herein by reference in their entirety, except that wherein there is conflict the definitions herein govern. Sulfones [Y=—S(=O)$_2$—; X=—CH(—R$_2$)— or X=—S(=O)$_2$—; Y=—CH(—R$_2$)—], Sulfoxides [Y=—S(=O)—; X=—CH(—R$_2$)— or X=—S(=O)—; Y=—CH(—R$_2$)—], Sulfides [Y=—S—; X=—CH(—R$_2$)— or X=—S—; Y=—CH(—R$_2$)—], and Sulfonamides [Y=—S(=O)$_2$—; X=—N(—R$_1$)— or X=—S(=O)$_2$—; Y=—N(—R$_1$)—] of Compound 1 of Scheme 5 can be prepared as disclosed in U.S. Patent Appl. Publs. 2009/0124828 and 2008/058290, which are incorporated herein by reference in their entirety, except that wherein there is conflict the definitions herein govern. Sulfoxides [Y=—S(=O)—; X=—CH(—R$_2$)— or X=—S(=O)—; Y=—CH(—R$_2$)—] of Compound 1 of Scheme 5 can be prepared as disclosed in U.S. Patent Appl. Publs. 2006/0280746, which are incorporated herein by reference in their entirety, except that wherein there is conflict the definitions herein govern. Amides of Compound 1 [Y=—N(—R$_1$)—; X=—C(=O)$_2$— or X=—N(—R$_1$)—; Y=—C(=O)$_2$-] of Scheme 5 can be prepared as disclosed in U.S. Patent Appl. Publs. 2006/0167317, which are incorporated herein by reference in their entirety, except that wherein there is conflict the definitions herein govern. Sulfonamides of Compound 1 [Y=—S(=O)$_2$—; X=—N(—R$_1$)— or X=—S(=O)$_2$—; Y=—N(—R$_1$)—] of Scheme 5 can be prepared as in U.S. Patent Appl. Publs. 2002/0165412, which are incorporated herein by reference in their entirety, except that wherein there is conflict the definitions herein govern.

Example 3

2-Methoxy-5-(((2,4,6-trimethoxyphenethyl)sulfonyl)methyl)aniline

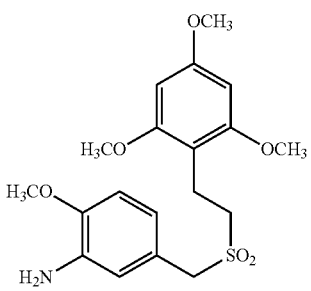 [SMILES: COc1cc(OC)c(CCS(=O)(=O)Cc2ccc(OC)c(N)c2)c(OC)c1]

The title compound was prepared according to Scheme 5. A solution of (E)-2-methoxy-5-(((2,4,6-trimethoxystyrylsulfonyl)methyl)aniline (1.5 mmol) in a mixture of MeOH (60 mL) was treated with wet 5% palladium on carbon (50 mg) then exposed to a hydrogen atmosphere by using hydrogenation apparatus. After completion of the reaction (monitored by TLC), the reaction mixture was filtered through Celite, the Celite pad was washed thoroughly with methanol, and the filtrate evaporated under reduced pressure and dried under vacuum to obtain the title compound according to General Procedure XIX with a yield of 95% and had a melting point: 128-130° C.

$^1$H NMR (CDCl$_3$, 300 MHz): δ 2.98-3.04 (m, 2H, CH$_2$), 3.08-3.15 (m, 2H, CH$_2$), 3.80 (s, 2H, NH$_2$), 3.81 (s, 6H, 2×OCH$_3$), 3.82 (s, 3H, OCH$_3$), 3.86 (s, 3H, OCH$_3$), 4.13 (s, 2H, CH$_2$), 6.13 (s, 2H, Ar—H), 6.76 (s, 3H, Ar—H). HRMS: m/z calcd [M+H] 396.14. found 396.12.

Example 4

2-((2-Methoxy-5-(((2,4,6-trimethoxyphenethyl)sulfonyl)methyl)amino)acetic acid

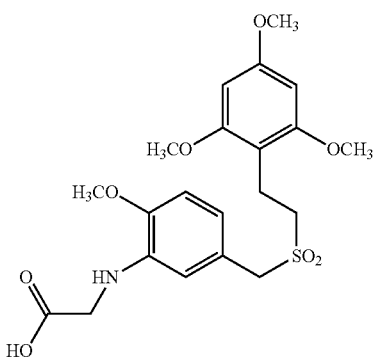 [SMILES: COc1cc(OC)c(CCS(=O)(=O)Cc2ccc(OC)c(NCC(=O)O)c2)c(OC)c1]

The title compound was prepared according to Scheme 5. A solution of (E)-2-((2-methoxy-5-(((2,4,6-trimethoxystyryl)sulfonyl)methyl)phenyl)amino)acetic acid (1.5 mmol) in a mixture of MeOH/EtOAc (40 mL) was treated with wet 10% palladium on carbon (50 mg) then exposed to hydrogen atmosphere by using hydrogenation apparatus. After completion of the reaction (monitored by TLC), the reaction mixture was filtered through Celite, washed the Celite pad thoroughly with a mixture of methanol and chloroform (50%) and the filtrate evaporated under reduced pressure. Filtered the solid, washed with ether and dried under vacuum to obtain the title compound according to General Procedure XIX with a yield of (96-98%).

Example 5

2-Methoxy-5-(((2,4,6-trimethoxyphenethyl)sulfonyl)methyl)phenol

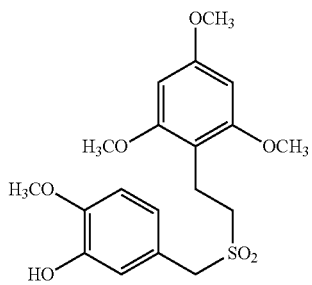 [SMILES: COc1cc(OC)c(CCS(=O)(=O)Cc2ccc(OC)c(O)c2)c(OC)c1]

The title compound was prepared according to Scheme 5. A solution of (E)-2-methoxy-5-((2,4,6-trimethoxystyrylsulfonyl)methyl)phenol (1.5 mmol) in a mixture of MeOH (60 mL) was treated with wet 5% palladium on carbon (50 mg) then exposed to hydrogen atmosphere by using hydrogenation apparatus. After completion of the reaction (monitored by TLC), the reaction mixture was filtered through Celite, the Celite pad was washed thoroughly with methanol, and the filtrate evaporated under reduced pressure and dried under vacuum to obtain the title compound according to General Procedure XIX with a 95% yield and a melting point of 136-138° C.

$^1$H NMR (CDCl3, 300 MHz): δ 2.97-3.04 (m, 2H, CH$_2$), 3.09-3.15 (m, 2H, CH$_2$), 3.82 (s, 3H, OCH$_3$), 3.84 (s, 6H, 2×OCH$_3$), 3.91 (s, 3H, OCH$_3$), 4.17 (s, 2H, CH$_2$), 5.63 (s, 1H, OH), 6.13 (s, 2H, Ar—H), 6.86 (d, J=8.1 Hz, 1H, Ar—H), 6.93-7.00 (m, 2H, Ar—H). HRMS: m/z calcd [M+H] 397.47. found 397.20.

Example 6

4-(2-((4-Chlorobenzyl)sulfonyl)ethyl)benzoic acid

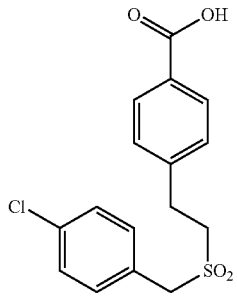 [SMILES: O=C(O)c1ccc(CCS(=O)(=O)Cc2ccc(Cl)cc2)cc1]

The title compound was prepared according to Scheme 5. A solution of (E)-4-(2-((4-chlorobenzyl)sulfonyl)vinyl)benzoic acid (500 mg, 1.48 mmol) in MeOH/EtOAc (1:1, 40 mL) was hydrogenated at 1 atm over 10% Pd—C for 48 h and then filtered through Celite. The Celite pad thoroughly washed with a mixture of methanol/chloroform (1:5). The combined solvent was removed under reduced pressure. The crude product was treated with methanol, filtered, washed with methanol, and dried to obtain the analytically pure title compound according to General Procedure XIX in an amount of yield of 480 mg and a melting point of 265-267° C.

$^1$H NMR: 3.12-3.10 (m, 2H, Ar—CH$_2$—CH$_2$—SO$_2$), 3.43-3.41 (m, 2H, Ar—CH$_2$—CH$_2$—SO$_2$), 4.58 (s, 2H, Ar—CH$_2$), 7.43 (d, 2H, Ar—H, J=6.0 Hz), 7.47 (d, 2H, Ar—H, J=6.0 Hz), 7.52 (d, 2H, Ar—H, J=6.0 Hz), 7.91 (d, 2H, Ar—H, J=6.0 Hz). HRMS: (M+Na): 360.99.

Example 7

N-(3-Amino-4-methoxyphenyl)-3-(2,4,6-trimethoxyphenyl)propanamide

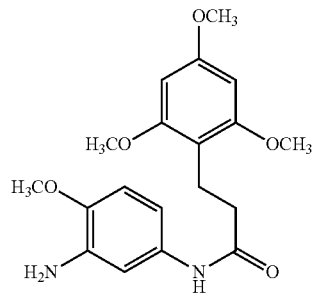 [SMILES: COc1cc(OC)c(CCC(=O)Nc2ccc(OC)c(N)c2)c(OC)c1]

The title compound was prepared according to Scheme 5. A solution of (E)-N-(3-amino-4-methoxyphenyl)-3-(2,4,6-trimethoxyphenyl)acrylamide (1.5 mmol) in a mixture of MeOH (60 mL) was treated with wet 5% palladium on carbon (50 mg), then exposed to a hydrogen atmosphere by using a hydrogenation apparatus. After completion of the reaction (monitored by TLC), the reaction mixture was filtered through Celite, the Celite pad was washed thoroughly with a methanol, and the filtrate was evaporated under reduced pressure and dried under vacuum to obtain the pure title compound according to General Procedure XIX with a yield of 96-98% and a melting point: 154-156° C.

$^1$H NMR (CDCl$_3$, 300 MHz): δ 2.55-2.60 (m, 2H, CH$_2$), 2.95-3.00 (m, 2H, CH$_2$), 3.77 (s, 3H, OCH$_3$), 3.81 (s, 6H, 2×OCH$_3$), 3.83 (s, 3H, OCH$_3$), 6.15 (s, 2H, Ar—H), 6.60-6.74 (m, 2H, Ar—H), 7.09 (d, J=8.1 Hz, 1H, Ar—H).

Scheme 6

General Procedures XX-XXIII are used to prepare Compounds 1-4 in Scheme 6.

Scheme 6

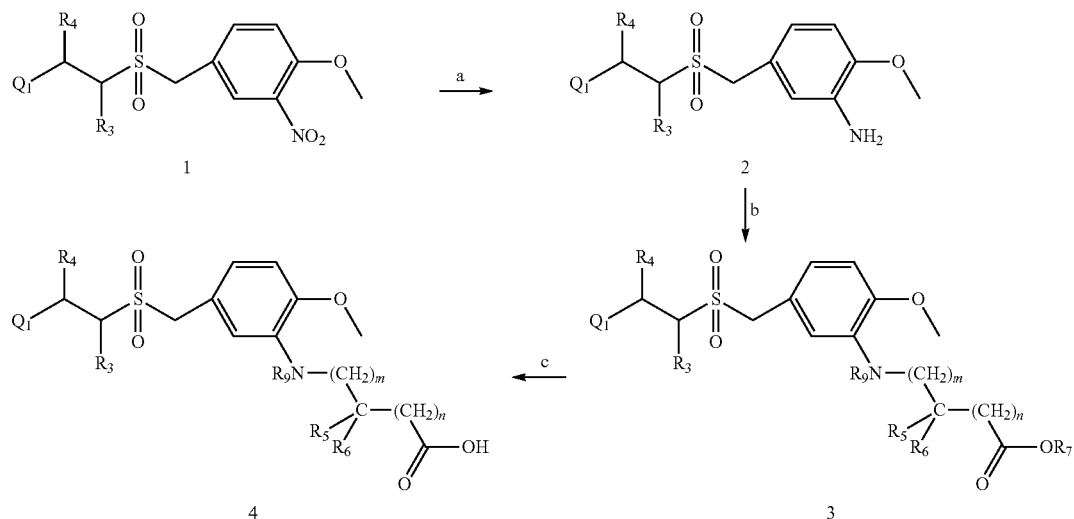

Non-limiting embodiments of reaction conditions for each step may include: a) Fe, MeOH:AcOH (2:1), reflux, 3 hours; b) i) (R=H) $BrCR_4R_5CO_2CH_3$, NaOAc, EtOH, reflux, 48 hours; or ii) $(Z=(CH_2CO_2CH_3)$ $ICH_2CO_2CH_3$, NaOAc, EtOH, reflux, 48 hours; and c) 20% aq. NaOH, EtOH, 2.5 hours.

General Procedure XX
Preparation of Compound 1 of Scheme 6: substituted 1-methoxy-2-nitro-4-((phenethylsulfonyl)methyl)benzenes.

Compound 1 of Scheme 6 can be prepared by following the procedure described for the Compound 7 in the Scheme 1.

General Procedure XXI
Preparation of Compound 2 of Scheme 6: 2-methoxy-5-((phenethylsulfonyl)methyl)anilines.

To a solution of Compound 1 of scheme 6 (2.4 mmol) in methanol/glacial acetic acid mixture (2:1, 120 ml), iron powder (12.0 mmol) is added and refluxed for 3 h. After completion of the reaction, the reaction mixture is cooled to 25° C. and 80 mL of cold water is added. The contents are neutralized with 4N ammonia solution and then 100 ml of dichloromethane ("DCM") is added and stirred for 30 min. The contents are separated in an organic layer, washed with water, sat. sodium bicarbonate solution and finally with brine. The dried organic layer is concentrated to two thirds and crystallized with either cyclohexane or petroleum ether. The solid is filtered and dried to obtain pure compounds 2 of scheme 6 (90%).

General Procedure XXII
Preparation of Compound 3 of Scheme 6: Substituted methyl 2-((2-methoxy-5-((phenethylsulfonyl)methyl)phenyl)amino)acetates.

Sodium acetate (40.0 mmol) is dissolved in ethanol (20 mL). Methyl bromoacetate (40.0 mmol) (or methyl idoacetate) is added to the above solution and refluxed for 10 min. Compound 2 of scheme 6 (10.0 mmol) is added and then refluxed for 48 h. After completion of the reaction monitored by TLC, the reaction mixture is concentrated under vacuum and poured into ice-water. The solid formed is filtered, washed with water, and dried under vacuum. The crude product on treatment with ethanol resulted in analytical pure products 3 of scheme 6 (70%).

General Procedure XXIII
Preparation of Compound 4 of Scheme 6: substituted 2-((2-methoxy-5-((phenethylsulfonyl)methyl)phenyl)amino)acetic acids.

To a solution of Compound 3 of scheme 6 (10.0 mmol) in ethanol (20 mL), 20% aqueous sodium hydroxide solution (20 mL) is added. The reaction mixture is refluxed for 2.5 h. After completion of the reaction (monitored by TLC), the solvent is removed under vacuum and the remaining water layer acidified by acetic acid to pH 4. The solid that formed is filtered and dried to get the crude amino acids 4 of scheme 6 which on crystallization from acetone (2×5 mL) resulted in analytically pure Compound 4 of scheme 6 as white crystals.

Example 8

Methyl 2-((2-methoxy-5-((2,4,6-trimethoxyphenethyl)sulfonyl)methyl)phenyl)amino)acetate

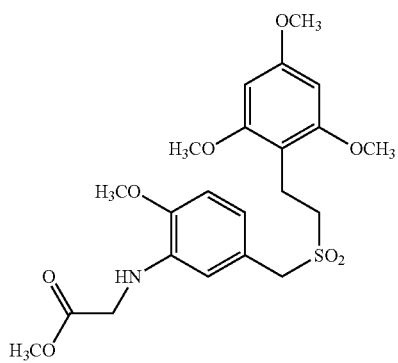 [SMILES: COC(=O)CNc1cc(CS(=O)(=O)CCc2c(OC)cc(OC)cc2OC)ccc1OC]

The title compound was prepared according to Scheme 6. Sodium acetate (3.28 g, 39 mmol) was dissolved in methanol (20 mL). Methyl 2-bromoacetate (6.11 g, 40 mmol) was added to the above solution and refluxed for 10 min. To the cooled reaction mixture, 2-methoxy-5-(((2,4,6-trimethoxyphenethyl)sulfonyl)methyl)aniline (3.95 g, 10 mmol) was added and then the reaction was reflux for 4-6 h. The reaction mixture was concentrated under vacuum and poured into ice water. The formed precipitate was filtered, washed with water, and dried under vacuum. The crude product was recrystallized from ethanol to produce the pure product of the title compound according to General Procedure XXII with a yield of 70% as a white solid with amp of 156-158° C.

$^1$H NMR (CDCl$_3$, 300 MHz): δ 2.98-3.04 (m, 2H, CH$_2$), 3.08-3.15 (m, 2H, CH$_2$), 3.79 (s, 3H, OCH$_3$), 3.81 (s, 6H, 2×OCH$_3$), 3.82 (s, 3H, OCH$_3$), 3.88 (s, 3H, OCH$_3$), 3.95 (d, J=4.2 Hz, 2H, CH$_2$), 4.17 (s, 2H, CH$_2$), 4.88 (t, J=5.4 Hz, 1H, NH), 6.13 (s, 2H, Ar—H), 6.53 (d, J=1.2 Hz, 1H, Ar—H), 6.74-6.78 (m, 2H, Ar—H). HRMS: m/z calcd [M+H] 468.14. found 468.1446.

Example 9

Dimethyl 2,2'-((2-methoxy-5-(((2,4,6-trimethoxyphenethyl)sulfonyl)methyl)phenyl)azanediyl)diacetate

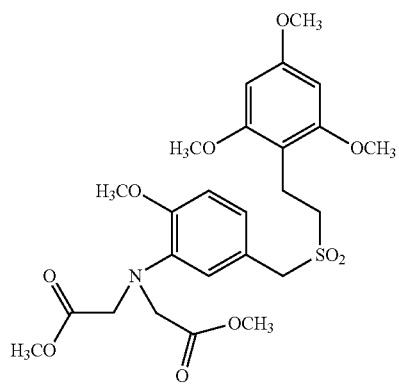 [SMILES: COC(=O)CN(CC(=O)OC)c1cc(CS(=O)(=O)CCc2c(OC)cc(OC)cc2OC)ccc1OC]

The title compound was prepared according to Scheme 6. Potassium carbonate (80 mmol) was dissolved in acetone (40 mL). Methyl-2-iodoacetate (80 mmol) was added to the above solution and refluxed for 10 min. To the cooled reaction mixture, 2-methoxy-5-((2,4,6-trimethoxyphenethylsulfonyl)methyl)aniline (10 mmol) was added and then refluxed for 60 h. The reaction mixture was concentrated under vacuum and poured into ice water. The formed precipitate was filtered, washed with water and dried under vacuum. The crude product according to General Procedure XXII was purified by column chromatography to produce pure product: yield, 70%; white solid, mp 86-88° C.

$^1$H NMR (CDCl$_3$, 300 MHz): δ 2.95-3.01 (m, 2H, CH$_2$), 3.06-3.13 (m, 2H, CH$_2$), 3.72 (s, 6H, 2×OCH$_3$), 3.81 (s, 6H, 2×OCH$_3$), 3.82 (s, 3H, OCH$_3$), 3.83 (s, 3H, OCH$_3$), 4.15 (s, 6H, CH$_2$), 6.12 (s, 2H, Ar—H), 6.82 (d, J=8.1 Hz, 1H, Ar—H), 6.91-6.97 (m, 2H, Ar—H).). HRMS: m/z calcd [M+H] 539.68. found 539.58.

Example 10

Alternative Synthesis of 2-((2-Methoxy-5-(((2,4,6-trimethoxyphenethyl)sulfonyl)methyl)phenyl)amino) acetic acid

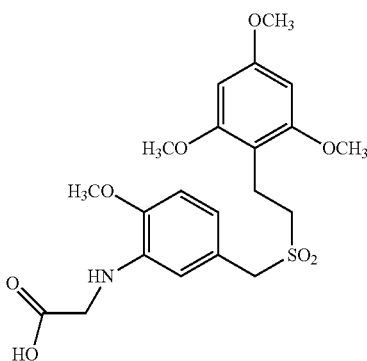 [SMILES: COc1cc(OC)c(CCS(=O)(=O)Cc2ccc(OC)c(NCC(=O)O)c2)c(OC)c1]

The title compound was prepared according to Scheme 6. To a solution of amine ester (46.5 g, 100 mmol) in ethanol (200 mL), 20% aqueous sodium hydroxide solution (200 mL) was added. The reaction mixture was refluxed for 2.5 h. After completion of the reaction (TLC, monitoring, chloroform/methanol, 9:1 on silica gel plate), the solvent was removed under vacuum and the remainder was acidified by acetic acid to pH 4. The solid that formed was filtered and dried to get the crude amino acid, which on crystallization from acetone (2×25 mL) resulted in analytically pure crystals of the title compound, according to General Procedure XXIII. The yield of this reaction was 55%. Melting point: 146-150° C.

$^1$H NMR (CDCl$_3$, 300 MHz): δ 2.96-3.01 (m, 2H, CH$_2$), 3.09-3.15 (m, 2H, CH$_2$), 3.82 (s, 9H, 3×OCH$_3$), 3.93 (s, 3H, OCH$_3$), 4.00 (s, 2H, CH$_2$), 4.17 (s, 2H, CH$_2$), 6.14 (s, 2H, Ar—H), 6.55 (s, 1H, Ar—H), 6.78 (s, 2H, Ar—H).). HRMS: m/z calcd [M+H] 454.52. found 454.20.

Example 11

2-((2-Methoxy-5-(((2,4,6-trimethoxyphenethyl)sulfonyl)methyl)phenyl)amino)propanoic acid

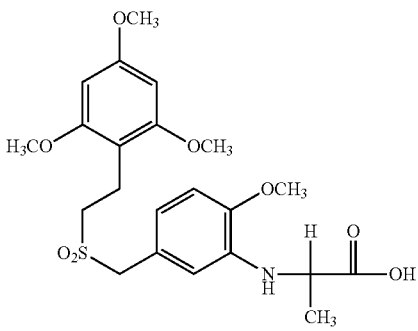 [SMILES: COc1cc(OC)c(CCS(=O)(=O)Cc2ccc(OC)c(NC(C)C(=O)O)c2)c(OC)c1]

The title compound is prepared according to Scheme 6. Sodium acetate (32.8 g, 400 mmol) is dissolved in ethanol (200 mL). 2-bromopropionate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid forms is filtered, washed with water, and dried under vacuum. The crude product on purification from ethanol results in analytical pure product, according to General Procedure XXII.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure white crystals of the title compound, according to General Procedure XXIII.

Example 12

2-((2-Methoxy-5-(((2,4,6-trimethoxyphenethyl)sulfonyl)methyl)phenyl)amino)-2-methylpropanoic acid

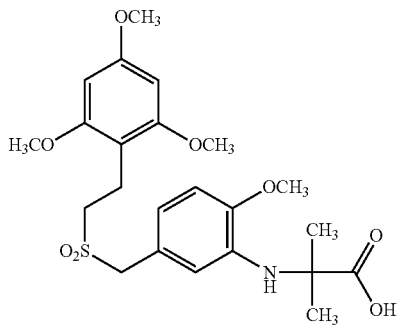 [SMILES: COc1cc(OC)c(CCS(=O)(=O)Cc2ccc(OC)c(NC(C)(C)C(=O)O)c2)c(OC)c1]

The title compound is prepared according to Scheme 6. Sodium acetate (32.8 g, 400 mmol) is dissolved in ethanol (200 mL). Methyl 2-bromo-2-methylpropionate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid formed is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure amino acid as white crystals of the title compound, according to General Procedures XXII and XXIII.

Example 13

2-((2-Methoxy-5-(((2,4,6-trimethoxyphenethyl)sulfonyl)methyl)phenyl)amino)-2-phenylacetic acid

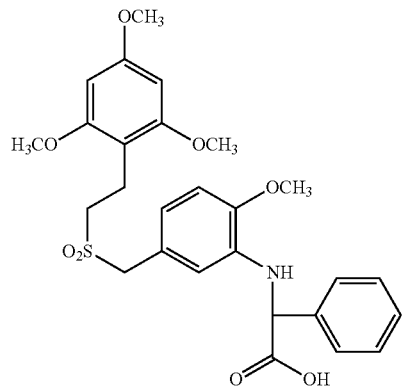 [SMILES: COc1cc(OC)c(CCS(=O)(=O)Cc2ccc(OC)c(NC(C(=O)O)c3ccccc3)c2)c(OC)c1]

The title compound is prepared according to Scheme 6. Sodium acetate (32.8 g, 400 mmol) is dissolved in ethanol (200 mL). Methyl α-bromophenylacetate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid formed is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure amino acid as white crystals of the title compound, according to General Procedures XXII and XXIII.

Example 14

2-(4-Fluorophenyl)-2-((2-methoxy-5-(((2,4,6-trimethoxyphenethyl)sulfonyl)methyl)phenyl)amino)acetic acid

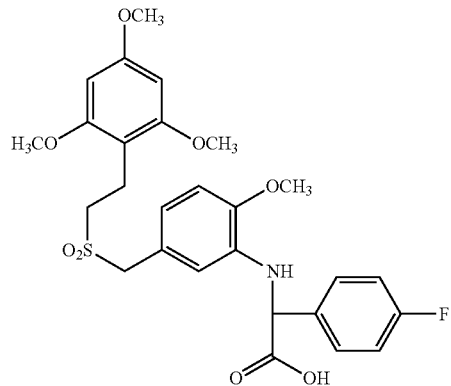 [SMILES: COc1cc(OC)c(CCS(=O)(=O)Cc2ccc(OC)c(NC(C(=O)O)c3ccc(F)cc3)c2)c(OC)c1]

The title compound is prepared according to Scheme 6. Sodium acetate (32.8 g, 400 mmol) is dissolved in ethanol (200 mL). 2-bromo-2-(4-fluorophenyl)acetate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid formed is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure amino acid as white crystals of the title compound, according to General Procedures XXII and XXIII Example 15

2-(4-Chlorophenyl)-2-((2-methoxy-5-(((2,4,6-trimethoxyphenethyl)sulfonyl)methyl)phenyl)amino) acetic acid

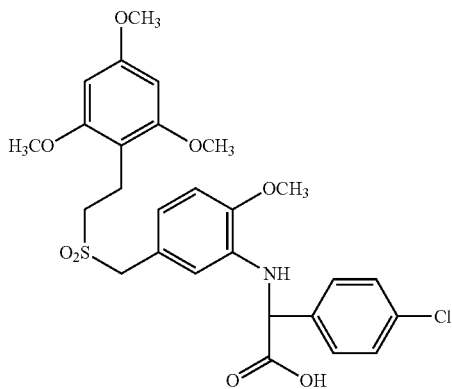 [SMILES: COc1cc(OC)c(CCS(=O)(=O)Cc2ccc(OC)c(NC(C(=O)O)c3ccc(Cl)cc3)c2)c(OC)c1]

The title compound is prepared according to Scheme 6. Sodium acetate (32.8 g, 400 mmol) is dissolved in ethanol (200 mL). 2-bromo-2-(4-chlorophenyl)acetate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid formed is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure amino acid as white crystals of the title compound, according to General Procedures XXII and XXIII.

Example 16

2-((2-Methoxy-5-(((2,4,6-trimethoxyphenethyl)sulfonyl)methyl)phenyl)amino)-3-phenylpropanoic acid

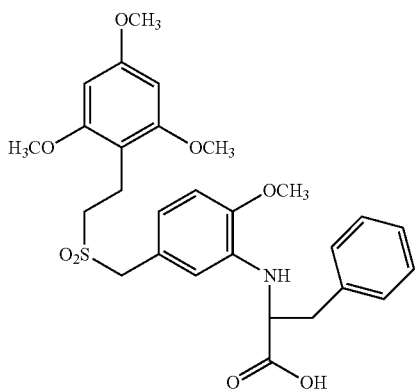 [SMILES: COc1cc(OC)c(CCS(=O)(=O)Cc2ccc(OC)c(NC(Cc3ccccc3)C(=O)O)c2)c(OC)c1]

The title compound is prepared according to Scheme 6. Sodium acetate (32.8 g, 400 mmol) is dissolved in ethanol (200 mL). Methyl 2-bromo-3-phenylpropanoate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid form is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure amino acid as white crystals of the title compound, according to General Procedures XXII and XXIII.

Example 17

2-Cyclopropyl-2-((2-methoxy-5-(((2,4,6-trimethoxyphenethyl)sulfonyl)methyl)phenyl)amino)acetic acid

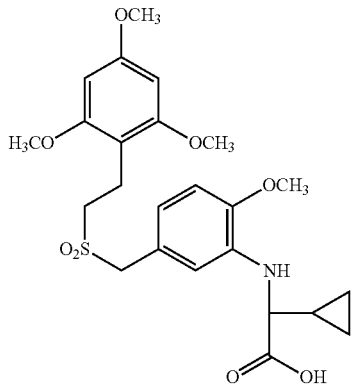 [SMILES: COc1cc(OC)c(CCS(=O)(=O)Cc2ccc(OC)c(NC(C(=O)O)C3CC3)c2)c(OC)c1]

The title compound is prepared according to Scheme 6. Sodium acetate (32.8 g, 400 mmol) is dissolved in ethanol (200 mL). Methyl 2-bromo-2-cyclopropylacetate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid form is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) is added. The reaction mixture is refluxed for 2.5 h. After completion of the reaction (TLC, monitoring, chloroform/methanol, 9:1 on silica gel plate), the solvent is removed under vacuum and the remainder is acidified by acetic acid to pH 4. The solid that forms is filtered and dried to get the crude amino acid which on crystallization from acetone (2-25 mL) results in analytically pure amino acid as white crystals of the title compound, according to General Procedures XXII and XXIII.

Example 18

2-((2-Methoxy-5-(((2,4,6-trimethoxyphenethyl)sulfonyl)methyl)phenyl)amino)-2-(1H-pyrrol-3-yl)acetic acid

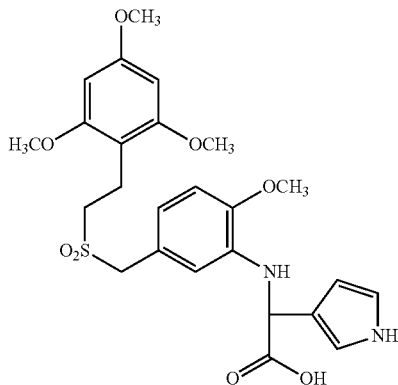 [SMILES: COc1cc(OC)c(CCS(=O)(=O)Cc2ccc(OC)c(NC(C(=O)O)c3cc[nH]c3)c2)c(OC)c1]

The title compound is prepared according to Scheme 6. Sodium acetate (32.8 g, 400 mmol) is dissolved in ethanol (200 mL). Methyl 2-bromo-2-(1H-pyrrol-3-yl)acetate (400 mmol) is added to the above solution and refluxed for 10 min. To the cooled reaction mixture compound 2-methoxy-5-(((2,4,6-trimethoxyphenethyl) sulfonyl)methyl)aniline (39.35 g, 100 mmol) is added and then refluxed for 48 h. After completion of the reaction monitored by TLC (chloroform/methanol, 9:1 on silica gel plate), the reaction mixture is concentrated under vacuum and poured into ice-water. The solid forms is filtered, washed with water, and dried under vacuum. The crude product on purification from ethanol results in analytical pure product.

To a solution of above amine ester (46.5 g, 100 mmol) in ethanol (200 mL), 20% aqueous sodium hydroxide solution (200 mL) was added. The reaction mixture is refluxed for 2.5 h. After completion of the reaction (TLC, monitoring, chloroform/methanol, 9:1 on silica gel plate), the solvent is removed under vacuum and the remainder was acidified by acetic acid to pH 4. The solid that forms was filtered and dried to get the crude amino acid which on crystallization from acetone (2-25 mL) results in analytically pure amino acid as white crystals of the Title compound, according to General Procedures XXII and XXIII.

Example 19

N-(3-Amino-4-methoxyphenyl)-2-(2,4,6-trimethoxyphenyl)ethanesulfonamide

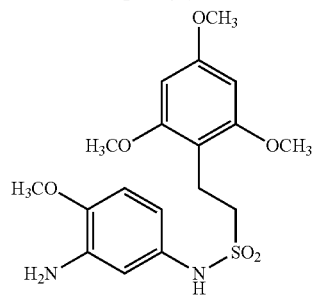 [SMILES: COc1cc(OC)c(CCS(=O)(=O)Nc2ccc(OC)c(N)c2)c(OC)c1]

The title compound was prepared according to Scheme 5. A solution of 2-(2,4,6-Trimethoxyphenyl)ethenesulfonic acid (3-amino-4-methoxyphenyl)amide (1.5 mmol) in a mixture of MeOH (60 mL) was treated with wet 5% palladium on carbon (50 mg) then exposed to hydrogen atmosphere by using hydrogenation apparatus. After completion of the reaction (monitored by TLC), the reaction mixture was filtered through Celite, washed the Celite pad thoroughly with methanol and the filtrate evaporated under reduced pressure and dried under vacuum to get pure N-(3-amino-4-methoxyphenyl)-2-(2,4,6-trimethoxyphenyl)-ethanesulfonamide (95%), according to General Procedure XIX.

Example 20

1,3,5-Trimethoxy-2-(2-((4-methoxybenzyl)sulfonyl)ethyl)benzene

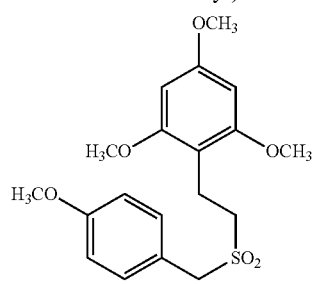

The title compound was prepared according to Scheme 5. A solution of (E)-2,4,6-trimethoxystyryl-4-methoxybenzyl-sulfone (1.5 mmol) in a mixture of MeOH (60 mL) was treated with wet 5% palladium on carbon (50 mg) then exposed to hydrogen atmosphere by using hydrogenation apparatus. After completion of the reaction (monitored by TLC), the reaction mixture was filtered through Celite, washed the Celite pad thoroughly with methanol and the filtrate evaporated under reduced pressure and dried under vacuum to get pure 1,3,5-trimethoxy-2-(2-((4-methoxybenzyl)sulfonyl)ethyl)benzene (95%), according to General Procedure XIX.

Example 21

2 ((2-methoxy-5-(((2,4,6-trimethoxyphenethyl)sulfonyl)methyl)phenyl)amino)acetate

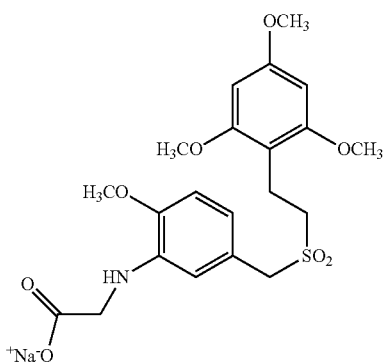

The title compound was prepared according to Scheme 6. Sodium acetate (3.28 g, 39 mmol) was dissolved in methanol (20 mL). Methyl 2-bromoacetate (6.11 g, 40 mmol) was added to the above solution and refluxed for 10 min. To the cooled reaction mixture compound 2-methoxy-5-(((2,4,6-trimethoxyphenethyl) sulfonyl)methyl)aniline (3.99 g, 10 mmol) was added, and then the mixture was refluxed for 4-6 h. The reaction mixture was concentrated under vacuum and poured into ice-water. The formed precipitate was filtered, washed with water, and dried under vacuum. The crude product on recrystallization from ethanol resulted in pure product.

To a solution of sodium hydroxide (3.95 g, 99 mmol) in water (11.5 mL) at 20° C. was added ethanol (40 mL), the above purified product (99 mmol) and dichloromethane (200 mL). The resulting mixture was stirred at room temperature for 3-4 h. After completion of the reaction monitored by TLC (chloroform/methanol, 9:1 on silica gel plate), charcoal was added and the mixture was stirred for 30 min. The reaction mixture was filtered through Celite and washed with ethanol (2×20 mL). The combined filtrate was distilled at 50° C. until most of the solvent was removed. Methyl ethyl ketone (70 mL) was added to the residue, and distillation of the methyl ethyl ketone was at 50° C. To the residue, water (10 mL) was added. The resulting mixture was heated to 70° C. and maintained for 30 min. The reaction mixture was cooled to room temperature and stirred for 2 h at room temperature. The solid formed was filtered, washed with methyl ethyl ketone (2×20 mL), and dried to get the purified title compound, according to General Procedures XXII and XXIII.

The compounds of Table 1 were prepared according to Examples 22-38 as follows:

TABLE 1

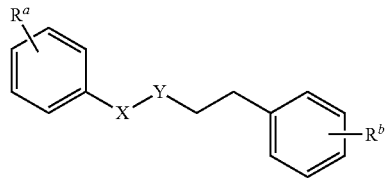

| Ex. | Compound | $R^a$ | $R^b$ | X | Y |
|---|---|---|---|---|---|
| 22 | N-(4-methoxyphenethyl)-4-methylbenzenesulfonamide | 4-$CH_3$ | 4-$OCH_3$ | $SO_2$ | NH |
| 23 | 4-methoxy-N-(4-methoxyphenethyl)-3-nitrobenzenesulfonamide | 3-$NO_2$, 4-$OCH_3$ | 4-$OCH_3$ | $SO_2$ | NH |
| 24 | 3-amino-4-methoxy-N-(4-methoxyphenethyl)benzenesulfonamide | 3-$NH_2$, 4-$OCH_3$ | 4-$OCH_3$ | $SO_2$ | NH |
| 25 | 4-methoxy-3-nitro-N-(2,4,6-trimethoxyphenethyl)benzenesulfonamide | 3-$NO_2$, 4-$OCH_3$ | 2,4,6-$(CH_3O)_3$ | $SO_2$ | NH |
| 26 | 3-amino-4-methoxy-N-(2,4,6-trimethoxyphenethyl)benzenesulfonamide | 3-$NH_2$, 4-$OCH_3$ | 2,4,6-$(CH_3O)_3$ | $SO_2$ | NH |
| 27 | 4-methoxy-N-(4-methoxyphenethyl)benzenesulfonamide | 4-$OCH_3$ | 4-$OCH_3$ | $SO_2$ | NH |
| 28 | 4-methoxy-N-(2,4,6-trimethoxyphenethyl)benzenesulfonamide | 4-$OCH_3$ | 2,4,6-$(CH_3O)_3$ | $SO_2$ | NH |
| 29 | 4-methyl-N-(2,4,6-trimethoxyphenethyl)benzenesulfonamide | 4-$CH_3$ | 2,4,6-$(CH_3O)_3$ | $SO_2$ | NH |
| 30 | 4-methoxy-N-(2,4,6-trimethoxyphenethyl)benzamide | 4-$OCH_3$ | 2,4,6-$(CH_3O)_3$ | CO | NH |
| 31 | 4-methoxy-N-(4-methoxyphenethyl)benzamide | 4-$OCH_3$ | 4-$OCH_3$ | CO | NH |
| 32 | 4-methoxy-N-(4-methoxyphenethyl)-3-nitrobenzamide | 3-$NO_2$, 4-$OCH_3$ | 4-$OCH_3$ | CO | NH |
| 33 | 3-amino-4-methoxy-N-(4-methoxyphenethyl)benzamide | 3-$NH_2$, 4-$OCH_3$ | 4-$OCH_3$ | CO | NH |
| 34 | 4-methoxy-3-nitro-N-(2,4,6-trimethoxyphenethyl)benzamide | 3-$NO_2$, 4-$OCH_3$ | 2,4,6-$(CH_3O)_3$ | CO | NH |
| 35 | 3-amino-4-methoxy-N-(2,4,6-trimethoxyphenethyl)benzamide | 3-$NH_2$, 4-$OCH_3$ | 2,4,6-$(CH_3O)_3$ | CO | NH |
| 36 | 2-(4-methoxyphenyl)-N-(2,4,6-trimethoxyphenyl)ethanesulfonamide | 2,4,6-$(CH_3O)_3$ | 4-$OCH_3$ | NH | $SO_2$ |
| 37 | 4-(((3,4-dimethoxyphenethyl)thio)methyl)-2-methoxyphenol | 3-$OCH_3$, 4-OH | 3,4-$(CH_3O)_2$ | $CH_2$ | S |
| 38 | 4-(((3,4-dimethoxyphenethyl)sulfonyl)methyl)-2-methoxyphenol | 3-$OCH_3$, 4-OH | 3,4-$(CH_3O)_2$ | $CH_2$ | $SO_2$ |

Example 22: N-(4-Methoxyphenethyl)-4-methylbenzenesulfonamide

The title compound was prepared from 2-(4-methoxyphenyl)ethanamine and p-toluenesulfonyl chloride according to Scheme 2 and General procedures VII-XI. $^1$H NMR (CDCl$_3$, 300 MHz): δ 2.33 (s, 3H, CH$_3$), 2.60 (t, J=7.2 Hz, 2H, CH$_2$), 3.03-3.10 (m, 2H, CH$_2$), 3.68 (s, 3H, OCH$_3$), 4.71 (s, 1H, NH), 6.81 (d, J=8.4 Hz, 2H, Ar—H), 6.90 (d, J=8.4 Hz, 2H, Ar—H), 7.19 (d, J=8.1 Hz, 2H, Ar—H), 7.61 (d, J=8.4 Hz, 2H, Ar—H). HRMS: m/z calcd [M+H] 306.11. found 306.10.

Example 23: 4-Methoxy-N-(4-methoxyphenethyl)-3-nitrobenzenesulfonamide

The title compound was prepared from 2-(4-methoxyphenyl)ethanamine and 4-methoxy-3-nitrophenylsulfonyl chloride according to Scheme 2 and General procedures VII-XI. $^1$H NMR (CDCl$_3$, 300 MHz): δ 2.75 (t, J=6.6 Hz, 2H, CH$_2$), 3.24-3.27 (m, 2H, CH$_2$), 3.80 (s, 3H, OCH$_3$), 4.06 (s, 3H, OCH$_3$), 4.45 (t, J=6.3 Hz, 1H, NH), 6.70 (d, J=8.4 Hz, 2H, Ar—H), 7.02 (d, J=8.4 Hz, 2H, Ar—H), 7.15 (d, J=8.7 Hz, 1H, Ar—H), 7.94 (dd, J=2.4, 9.0 Hz, 1H, Ar—H), 8.25 (d, J=2.4 Hz, 1H, Ar—H). HRMS: m/z calcd [M+H] 367.09. found 367.10.

Example 24: 3-Amino-4-methoxy-N-(4-methoxyphenethyl)benzenesulfonamide

The title compound was prepared from the Example 23 compound according to Scheme 5 and General Procedure XIX. $^1$H NMR (CDCl$_3$, 300 MHz): δ 2.63 (t, J=6.9 Hz, 2H, CH$_2$), 3.07-3.10 (m, 2H, CH$_2$), 3.72 (s, 3H, OCH$_3$), 3.84 (s, 3H, OCH$_3$), 4.13 (t, J=6.3 Hz, 1H, NH), 6.74 (dd, J=2.1, 8.4 Hz, 3H, Ar—H), 6.93 (d, J=8.7 Hz, 2H, Ar—H), 6.99 (d, J=2.4 Hz, 1H, Ar—H), 7.13 (dd, J=2.1, 8.4 Hz, 1H, Ar—H). HRMS: m/z calcd [M+H] 337.11. found 337.20.

Example 25: 4-Methoxy-3-nitro-N-(2,4,6-trimethoxyphenethyl)benzenesulfonamide The title compound was prepared from 2-(2,4,6-trimethoxyphenyl)ethanamine and 4-methoxy-3-nitrophenylsulfonyl chloride according to Scheme 2 and General Procedures VII-XI. $^1$H NMR (CDCl$_3$, 300 MHz): δ 2.71 (t, J=6.3 Hz, 2H, CH$_2$), 3.19-3.25 (m, 2H, CH$_2$), 3.75 (s, 6H, 2×OCH$_3$), 3.80 (s, 3H, OCH$_3$), 4.03 (s, 3H, OCH$_3$), 4.90 (t, J=4.5 Hz, 1H, NH), 5.98 (s, 2H, Ar—H), 6.97 (d, J=8.7 Hz, 1H, Ar—H), 6.75 (dd, J=2.4, 9.0 Hz, 1H, Ar—H), 8.09 (d, J=2.4 Hz, 1H, Ar—H). HRMS: m/z calcd [M+H] 427.11. found 427.20.

Example 26: 3-Amino-4-methoxy-N-(2,4,6-trimethoxyphenethyl)benzenesulfonamide The title compound was prepared from the Example 25 compound according to Scheme 5 and General Procedure XIX. $^1$H NMR (CDCl$_3$, 300 MHz): δ 2.73 (t, J=6.3 Hz, 2H, CH$_2$), 3.10-3.14 (m, 2H, CH$_2$), 3.76 (s, 6H, 2×OCH$_3$), 3.82 (s, 3H, OCH$_3$), 3.93 (s, 3H, OCH$_3$), 4.63 (t, J=4.8 Hz, 1H, NH), 6.07 (s, 2H, Ar—H), 6.72 (d, J=8.4 Hz, 1H, Ar—H), 6.98 (s, 1H, Ar—H), 7.13 (dd, J=2.1, 8.4 Hz, 1H, Ar—H). HRMS: m/z calcd [M+H] 397.14. found 397.10.

Example 27: 4-Methoxy-N-(4-methoxyphenethyl)benzenesulfonamide

The title compound was prepared from 2-(4-methoxyphenyl)ethanamine and 4-methoxyphenylsulfonyl chloride according to Scheme 2 and General Procedures VII-XI. $^1$H NMR (CDCl$_3$, 300 MHz): δ 2.72 (t, J=6.3 Hz, 2H, CH$_2$), 3.18 (dd, J=6.9, 13.2 Hz, 2H, CH$_2$), 3.80 (s, 3H, OCH$_3$), 3.89 (s, 3H, OCH$_3$), 4.38 (t, J=6.3 Hz, 1H, NH), 6.82 (d, J=8.4 Hz, 2H, Ar—H), 6.97 (d, J=9.0 Hz, 2H, Ar—H), 7.01 (d, J=8.7 Hz, 2H, Ar—H), 7.75 (d, J=8.7 Hz, 2H, Ar—H). HRMS: m/z calcd [M+H] 332.10. found 332.10.

Example 28: 4-Methoxy-N-(2,4,6-trimethoxyphenethyl)benzenesulfonamide

The title compound was prepared from 2-(2,4,6-trimethoxyphenyl)ethanamine and 4-methoxyphenylsulfonyl chloride according to Scheme 2 and General Procedures VII-XI. $^1$H NMR (CDCl$_3$, 300 MHz): δ 2.63 (t, J=6.3 Hz, 2H, CH$_2$), 3.02-3.04 (m, 2H, CH$_2$), 3.65 (s, 6H, 2×OCH$_3$), 3.73 (s, 3H, OCH$_3$), 3.79 (s, 3H, OCH$_3$), 4.58 (t, J=4.8 Hz, 1H, NH), 5.95 (s, 2H, Ar—H), 6.76 (d, J=9.0 Hz, 2H, Ar—H), 7.52 (d, J=9.0 Hz, 2H, Ar—H). HRMS: m/z calcd [M+H] 382.12. found 382.10.

Example 29: 4-Methyl-N-(2,4,6-trimethoxyphenethyl)benzenesulfonamide

The title compound was prepared from 2-(2,4,6-trimethoxyphenyl)ethanamine and p-toluenesulfonyl chloride according to Scheme 2 and General Procedures VII-XI. $^1$H NMR (CDCl$_3$, 300 MHz): δ 2.32 (s, 3H, CH$_3$), 2.62 (t, J=6.3 Hz, 2H, CH$_2$), 3.00-3.04 (m, 2H, CH$_2$), 3.65 (s, 6H, 2×OCH$_3$), 3.73 (s, 3H, OCH$_3$), 4.59 (t, J=4.5 Hz, 1H, NH), 5.96 (s, 2H, Ar—H), 7.10 (d, J=8.1 Hz, 2H, Ar—H), 7.49 (d, J=8.1 Hz, 2H, Ar—H). HRMS: m/z calcd [M+H] 366.13. found 366.10.

Example 30: 4-Methoxy-N-(2,4,6-trimethoxyphenethyl)benzamide

The title compound was prepared from 2-(2,4,6-trimethoxyphenyl)ethanamine and 4-methoxybenzoic acid according to Scheme 3 and General Procedures XII-XIV. $^1$H NMR (CDCl$_3$, 300 MHz): δ 2.94 (t, J=6.3 Hz, 2H, CH$_2$), 3.55-3.59 (m, 2H, CH$_2$), 3.83 (s, 3H, OCH$_3$), 3.84 (s, 6H, 2×OCH$_3$), 3.85 (s, 3H, OCH$_3$), 6.17 (s, 2H, Ar—H), 6.60 (br s, 1H, NH), 6.90 (d, J=9.0 Hz, 2H, Ar—H), 7.66 (d, J=8.7 Hz, 2H, Ar—H). HRMS: m/z calcd [M+H] 346.10. found 346.20.

Example 31: 4-Methoxy-N-(4-methoxyphenethyl)benzamide

The title compound was prepared from 2-(4-methoxyphenyl)ethanamine and 4-methoxybenzoic acid according to Scheme 3 and General Procedures XII-XIV. $^1$H NMR (CDCl$_3$, 300 MHz): δ 2.79 (t, J=6.6 Hz, 2H, CH$_2$), 3.55-3.63 (m, 2H, CH$_2$), 3.73 (s, 3H, OCH$_3$), 3.77 (s, 3H, OCH$_3$), 5.97 (br s, 1H, NH), 6.75-6.87 (m, 4H, Ar—H), 7.08 (d, J=8.7 Hz, 2H, Ar—H), 7.59 (d, J=9.0 Hz, 2H, Ar—H). HRMS: m/z calcd [M+H] 386.14. found 286.10.

Example 32: 4-Methoxy-N-(4-methoxyphenethyl)-3-nitrobenzamide

The title compound was prepared from 2-(4-methoxyphenyl)ethanamine and 4-methoxy-3-nitrobenzoic acid according to Scheme 3 and General Procedures XII-XIV. $^1$H NMR (CDCl$_3$, 300 MHz): δ 2.90 (t, J=6.6 Hz, 2H, CH$_2$), 3.65-3.74 (m, 2H, CH$_2$), 3.82 (s, 3H, OCH$_3$), 4.03 (s, 3H, OCH$_3$), 6.11

(br s, 1H, NH), 6.90 (d, J=8.7 Hz, 2H, Ar—H), 7.16 (d, J=1.8 Hz, 1H, Ar—H), 7.18 (d, J=9.0 Hz, 2H, Ar—H), 7.99 (dd, J=2.1, 8.7 Hz, 1H, Ar—H), 8.17 (d, J=2.4 Hz, 1H, Ar—H). HRMS: m/z calcd [M+H] 331.12. found 331.10.

Example 33:
3-Amino-4-Methoxy-N-(4-methoxyphenethyl)benzamide

The title compound was prepared from the Example 32 compound according to Scheme 5 and General Procedure XIX. $^1$H NMR (CDCl$_3$, 300 MHz): δ 2.87 (t, J=6.9 Hz, 2H, CH$_2$), 3.64-3.70 (m, 2H, CH$_2$), 3.82 (s, 3H, OCH$_3$), 3.90 (s, 3H, OCH$_3$), 6.00 (br s, 1H, NH), 6.77 (d, J=8.4 Hz, 1H, Ar—H), 6.88 (d, J=8.7 Hz, 2H, Ar—H), 7.03 (dd, J=2.1, 8.4 Hz, 1H, Ar—H), 7.14 (d, J=2.1 Hz, 1H, Ar—H), 7.17 (d, J=8.4 Hz, 2H, Ar—H). HRMS: m/z calcd [M+H] 301.15. found 301.20.

Example 34: 4-Methoxy-3-nitro-N-(2,4,6-trimethoxyphenethyl)benzamide

The title compound was prepared from 2-(2,4,6-trimethoxyphenyl)ethanamine and 4-methoxy-3-nitrobenzoic acid according to Scheme 3 and General Procedures XII-XIV. NMR (CDCl$_3$, 300 MHz): δ 2.96 (t, J=6.3 Hz, 2H, CH$_2$), 3.55-3.60 (m, 2H, CH$_2$), 3.83 (s, 3H, OCH$_3$), 3.88 (s, 6H, 2×OCH$_3$), 4.03 (s, 3H, OCH$_3$), 6.20 (s, 2H, Ar—H), 6.82 (br s, 1H, NH), 7.15 (d, J=9.3 Hz, 1H, Ar—H), 8.08 (d, J=2.4 Hz, 1H, Ar—H), 8.11 (d, J=1.8 Hz, 1H, Ar—H). HRMS: m/z calcd [M+H] 391.14. found 391.20.

Example 35: 3-Amino-4-methoxy-N-(2,4,6-trimethoxyphenethyl)benzamide

The title compound was prepared from the Example 34 compound according to Scheme 5 and General Procedure XIX. $^1$H NMR (CDCl$_3$, 300 MHz): δ 2.92 (t, J=6.3 Hz, 2H, CH$_2$), 3.52-3.57 (m, 2H, CH$_2$), 3.83 (s, 3H, OCH$_3$), 3.84 (s, 6H, 2×OCH$_3$), 3.90 (s, 3H, OCH$_3$), 6.17 (s, 2H, Ar—H), 6.55 (br s, 1H, NH), 6.76 (d, J=8.4 Hz, 1H, Ar—H), 7.02 (dd, J=2.1, 8.4 Hz, 1H, Ar—H), 7.15 (d, J=2.1 Hz, 1H, Ar—H). HRMS: m/z calcd [M+H] 361.17. found 361.20.

Example 36: 2-(4-Methoxyphenyl)-N-(2,4,6-trimethoxyphenyl)ethanesulfonamide

The title compound was prepared from 2,4,6-trimethoxyaniline and 2-(4-methoxyphenyl)ethanesulfonyl chloride according to Scheme 2 and General Procedures VII-XI. $^1$H NMR (CDCl$_3$, 300 MHz): δ 3.09-3.15 (m, 2H, CH$_2$), 3.38-3.44 (m, 2H, CH$_2$), 3.72 (s, 3H, OCH$_3$), 3.73 (s, 3H, OCH$_3$), 3.76 (s, 6H, 2×OCH$_3$), 5.66 (s, 1H, NH), 6.08 (s, 2H, Ar—H), 6.79 (d, J=8.7 Hz, 2H, Ar—H), 7.08 (d, J=8.7 Hz, 2H, Ar—H). HRMS: m/z calcd [M+H] 382.12. found 382.10.

Example 37: 4-(((3,4-dimethoxyphenethyl)thio)methyl)-2-methoxyphenol

The title compound was prepared from 4-(2-bromoethyl)-1,2-dimethoxybenzene and 4-(mercaptomethyl)-2-methoxyphenol according to Scheme 1 and General Procedure V. $^1$H NMR (CDCl$_3$, 300 MHz): δ 2.62-2.68 (m, 2H, —CH$_2$), 2.77-2.95 (m, 2H, —CH$_2$), 3.68 (s, 2H, Ar—CH$_2$), 3.87 (s, 6H, 2×OCH$_3$), 3.90 (s, 3H, OCH$_3$), 5.57 (br s, 1H, OH), 6.66-6.88 (m, 6H, Ar—H). HRMS: m/z calcd [M+H] 335.13. found 335.10.

Example 38: 4-(((3,4-dimethoxyphenethyl)sulfonyl)methyl)-2-methoxyphenol

The title compound was prepared from the Example 37 compound according to Scheme 1 and General Procedure VI. $^1$H NMR (CDCl$_3$, 300 MHz): δ, 2.95-3.01 (m, 2H, —CH$_2$), 3.04-3.10 (m, 2H, —CH$_2$), 3.79 (s, 6H, 2×OCH$_3$), 3.80 (s, 3H, OCH$_3$), 4.09 (s, 2H, Ar—CH$_2$), 6.17 (br s, 1H, OH), 6.64-6.69 (m, 2H, Ar—H), 6.71-6.77 (m, 2H, Ar—H), 6.83 (d, J=8.1 Hz, 1H, Ar—H), 6.88 (d, J=1.8 Hz, 1H, Ar—H). HRMS: m/z calcd [M+H] 367.12. found 367.20.

Example 39: Cancer Cell Assays

The effect of the compounds of the invention on tumor cells was determined by the assay described by Latham et al., *Oncogene* 12:827-837 (1996). Tumor cells K562 (chronic myelogenous leukemia; leukemia cell line +ve for Bcr-Abl) or DU145 (prostate cancer) were plated in 12-well dishes at a cell density of 2.5×10$^4$ cells well. The plated cells were treated 24 hours later with a compound of the invention dissolved in DMSO at multiple concentrations ranging from 0.01 μM to 100 μM. The plates were examined 96 hours later under an inverted microscope, Olympus CK-2 using a 10× objective, and compound activity was noted by physical observation. When necessary, the total number of viable cells was determined by trypsinizing the wells and counting the number of viable cells, as determined by trypan blue exclusion, using a hemacytometer. The results of these assays are provided below in Table 2.

TABLE 2

| Example # | IC$_{50}$ (μM) K562 | IC$_{50}$ (μM) DU145 |
| --- | --- | --- |
| 2 | 1.5 | 1.5 |
| 3 | 0.0025 | 0.003 |
| 4 | 0.5 | 0.25 |
| 5 | 0.003 | 0.0075 |
| 6 | 10 | 10 |
| 7 | 0.15 | 5 |
| 8 | 0.15 | 0.15 |
| 9 | 2 | 2 |
| 19 | 0.003 | 0.005 |
| 20 | 0.05 | 0.15 |
| 21 | 0.04 | 0.15 |
| 22 | 60 | 60 |
| 23 | 35 | 35 |
| 25 | 35 | 35 |
| 26 | 0.75 | 5 |
| 27 | 75 | 75 |
| 28 | >10 | >10 |
| 29 | >10 | >10 |
| 30 | 5 | 15 |
| 31 | 100 | 75 |
| 32 | 75 | 75 |
| 33 | 75 | 75 |
| 34 | 75 | 75 |
| 35 | 0.5 | 5 |
| 36 | 2.5 | 15 |
| 37 | 5 | 15 |
| 38 | >10 | >10 |

All references cited herein are incorporated by reference. The present invention may be embodied in other specific forms without departing from the spirit or essential attributes thereof and, accordingly, reference should be made to the appended claims, rather than to the foregoing specification, as indicating the scope of the invention.

What is claimed is:

1. A compound of Formula I or a salt thereof;

$$Q_2\text{-}X\text{-}Y\text{---}CHR_3\text{---}CHR_4\text{-}Q_1 \qquad (I)$$

wherein:
$Q_1$ is substituted phenyl, with up to 5 substituents selected from the group consisting of:
 fluoro; bromo; nitro; —$NR_{10}R_{11}$; aroylamino; carboxy; cyano; carboxamido; trifluoromethyl; —O—$R_{10}$; and [—N(—$R_1$)—$(CH_2)_m$—C(—$R_5$)(—$R_6$)—$(CH_2)_n$—$COOR_7]_z$;
 wherein at least the 4-position of $Q_1$ is substituted;
$Q_2$ is substituted phenyl, with up to 5 substituents selected from the group consisting of:
 fluoro; chloro; nitro; —$NR_{10}R_{11}$; aroylamino; cyano; carboxy; carboxamido; trifluoromethyl; —O—$SO_2$—OH; —O—P(=O)(O$R_8)_2$; —O—$R_{10}$; [—N(—$R_9$)—$(CH_2)_m$—C(—$R_5$)(—$R_6$)—$(CH_2)_n$—$COOR_7]_z$; and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —N(—$R_1$)—, —O— or —S—;
 wherein at least one of $Q_1$ and $Q_2$ is substituted with a substituent other than unsubstituted phenyl;
X is —CH($R_2$)—;
Y is —S(=O)$_2$—;
$R_1$ and $R_2$ are each independently selected from the group consisting of H and a $C_1$-$C_{10}$ saturated or unsaturated, straight or branched, cyclic or acyclic, chiral or achiral hydrocarbyl group, wherein optionally at least one carbon atom of the hydrocarbyl group is replaced by —O— or —S—;
$R_3$ and $R_4$ are H;
$R_5$ and $R_6$ are each independently selected from the group consisting of H; halo; and $C_1$-$C_{10}$ saturated or unsaturated, straight or branched, cyclic or acyclic, chiral or achiral hydrocarbyl group, optionally substituted with one or more of halogen, $C_1$-$C_4$ alkyl, $C_1$-$C_4$ alkoxy, hydroxy, carboxy, carboxamido, amino, ($C_1$-$C_6$) alkyl, ($C_1$-$C_{10}$) dialkyl amino, or acylamino; or
$R_5$ and $R_6$ may combine to form a saturated or unsaturated carbocyclic ring with from 3 to 6 carbon atoms, wherein one or more carbon atoms is optionally replaced with —N(—$R_1$)—, —O—, or —S—;
$R_7$ is selected from the group consisting of H; and a $C_1$-$C_{10}$ saturated or unsaturated, straight or branched, cyclic or acyclic, chiral or achiral hydrocarbyl group; and an inorganic cation or an organic cation to form a salt;
$R_8$ is selected from the group consisting of H and ($C_1$-$C_7$) hydrocarbyl;
$R_9$ is selected from the group consisting of H and —$(CH_2)_m$—C(—$R_5$)(—$R_6$)—$(CH_2)_n$—$COOR_7$;
$R_{10}$ is selected from the group consisting of H, branched or unbranched ($C_1$-$C_6$)alkyl, and ($C_2$-$C_8$)acyl;
$R_{11}$ is selected from the group consisting of H, branched or unbranched ($C_1$-$C_6$)alkyl, and ($C_2$-$C_5$)acyl;
m and n are each independently 0-2; and
z is 1-2.

2. A compound according to claim 1, or a salt thereof, wherein $Q_1$ has at least one substituent that is carboxy, —O—$R_{10}$ or fluoro.

3. A compound according to claim 1, or a salt thereof, wherein $Q_2$ has at least one substituent selected from the group consisting of chloro; —O—$R_{10}$; —$NR_{10}R_{11}$; and [—N(—$R_9$)—$(CH_2)_m$—C(—$R_5$)(—$R_6$)—$(CH_2)_n$—$COOR_7]_z$.

4. A compound according to claim 2, or a salt thereof, wherein $Q_2$ has at least one substituent selected from the group consisting of chloro; —O—$R_{10}$; —$NR_{10}R_{11}$; and [—N(—$R_9$)—$(CH_2)_m$—C(—$R_5$)(—$R_6$)—$(CH_2)_n$—$COOR_7]_z$.

5. A compound according to claim 4, or a salt thereof, wherein $Q_2$ has a substituent at the 4-position thereof.

6. A compound according to claim 5, or a salt thereof, wherein $Q_1$ is substituted at the 2-, 4- and 6-positions with ($C_1$-$C_3$)alkoxy, and $Q_2$ is substituted in at least the 4-position with —O—$R_{10}$ or —$NR_{10}R_{11}$.

7. A compound according to claim 6, or a salt thereof, wherein $Q_2$ is substituted at the 4-position with —O—$R_{10}$ or —$NR_{10}R_{11}$ and substituted at the 3-position with —$NR_{10}R_{11}$, —O—$R_{10}$ or —N(—$R_9$)—$(CH_2)_m$—C(—$R_5$)(—$R_6$)—$(CH_2)_n$—$COOR_7]_z$.

8. A compound according to claim 1 selected from the group consisting of:
 1-chloro-4-(((4-fluorophenethyl)sulfonyl)methyl)benzene;
 2-methoxy-5-(((2,4,6-trimethoxyphenethyl)sulfonyl)methyl)aniline;
 2-methoxy-5-(((2,4,6-trimethoxyphenethyl)sulfonyl)methyl)phenol;
 4-(2-((4-chlorobenzyl)sulfonyl)ethyl)benzoic acid;
 methyl 2-((2-methoxy-5-(((2,4,6-trimethoxyphenethyl)sulfonyl)methyl)phenyl)amino)acetate;
 dimethyl 2,2'-((2-methoxy-5-(((2,4,6-trimethoxyphenethyl)sulfonyl)methyl)phenyl)azanediyl)diacetate;
 2-((2-methoxy-5-(((2,4,6-trimethoxyphenethyl)sulfonyl)methyl)phenyl)amino)acetic acid;
 2-((2-methoxy-5-(((2,4,6-trimethoxyphenethyl)sulfonyl)methyl)phenyl)amino)propanoic acid;
 2-((2-methoxy-5-(((2,4,6-trimethoxyphenethyl)sulfonyl)methyl)phenyl)amino)-2-methylpropanoic acid;
 2-((2-methoxy-5-(((2,4,6-trimethoxyphenethyl)sulfonyl)methyl)phenyl)amino)-2-phenylacetic acid;
 2-(4-fluorophenyl)-2-((2-methoxy-5-((2,4,6-trimethoxyphenethyl)sulfonyl)methyl)phenyl)amino)acetic acid;
 2-(4-chlorophenyl)-2-((2-methoxy-5-(((2,4,6-trimethoxyphenethyl)sulfonyl)methyl)phenyl)amino)acetic acid;
 2-((2-methoxy-5-(((2,4,6-trimethoxyphenethyl)sulfonyl)methyl)phenyl)amino)-3-phenylpropanoic acid;
 2-cyclopropyl-2-(((2-methoxy-5-(((2,4,6-trimethoxyphenethyl)sulfonyl)methyl)phenyl)amino)acetic acid;
 2-((2-methoxy-5-(((2,4,6-trimethoxyphenethyl)sulfonyl)methyl)phenyl)amino)-2-(1H-pyrrol-3-yl)acetic acid;
 1,3,5-trimethoxy-2-(2-((4-methoxybenzyl)sulfonyl)ethyl)benzene;
 and salts thereof.

9. A compound according to claim 8, wherein the compound is selected from the group consisting of:
 2-((2-methoxy-5-(((2,4,6-trimethoxyphenethyl)sulfonyl)methyl)phenyl)amino)acetic acid;
 2-methoxy-5-(((2,4,6-trimethoxyphenethyl)sulfonyl)methyl)aniline;
 2-methoxy-5-(((2,4,6-trimethoxyphenethyl)sulfonyl)methyl)phenol;
 methyl 2-((2-methoxy-5-(((2,4,6-trimethoxyphenethyl)sulfonyl)methyl)phenyl)amino)acetate;
 1,3,5-trimethoxy-2-(2-((4-methoxybenzyl)sulfonyl)ethyl)benzene;
 and salts thereof.

10. The compound according to claim 9 which is sodium 2-((2-methoxy-5-(((2,4,6-trimethoxyphenethyl)sulfonyl)methyl)phenyl)amino)acetate.

11. A compound according to claim 9 which is 2-((2-methoxy-5-(((2,4,6-trimethoxyphenethyl)sulfonyl)methyl)phenyl)amino) acetic acid, or pharmaceutically acceptable salt thereof.

12. A pharmaceutical composition comprising a pharmaceutically acceptable carrier and a compound, or a pharmaceutically acceptable salt thereof, according to claim 1.

13. A pharmaceutical composition comprising a pharmaceutically acceptable carrier and a compound, or a pharmaceutically acceptable salt thereof, according to claim 8.

14. The pharmaceutical composition according to claim 12, wherein the compound is 2-((2-methoxy-5-(((2,4,6-trimethoxyphenethyl)sulfonyl)methyl)phenyl)amino)acetic acid, or pharmaceutically acceptable salt thereof.

15. A process of making a compound of Formula I or a salt thereof according to claim 1, having a Formula Ib:

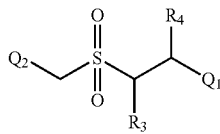

Formula Ib said process comprising:
oxidizing a compound of Formula Ia:

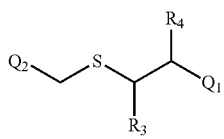

Formula Ia to produce a compound of Formula Ib or a salt thereof in a reaction mixture, and optionally isolating compound Formula Ib or a salt thereof from the reaction mixture, wherein $Q_1$, $Q_2$, $R_3$, and $R_4$ are as defined in claim 1.

16. The process of claim 15, wherein the reaction takes place in the presence of an acid and a peroxide.

17. A process of making a compound of Formula I or a salt thereof according to claim 1, having a Formula If:

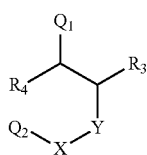

Formula If said process comprising:
reacting a compound of Formula Ie:

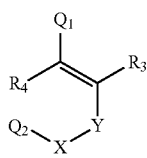

Formula Ie to produce a compound of Formula If or a salt thereof in a reaction mixture, and optionally isolating the compound of Formula If or a salt thereof from the reaction mixture, wherein X, Y, $Q_1$, $Q_2$, $R_3$, and $R_4$ are as defined in claim 1.

18. The process of claim 17, wherein the reaction takes place in the presence of at least one of a platinum, rhodium, Raney nickel, or palladium catalyst.

19. A process of making a compound of Formula I or a salt thereof according to claim 1, having the Formula Ii:

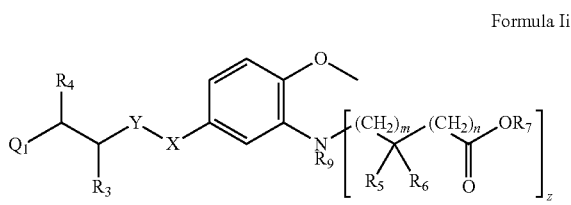

Formula Ii said process comprising:
reacting a compound of Formula Ih:

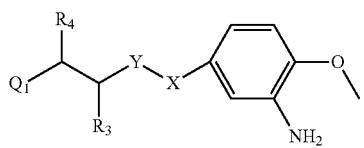

Formula Ih to produce a compound of Formula Ii or a salt thereof in a reaction mixture, and optionally isolating the compound Formula Ii or a salt thereof from the reaction mixture, wherein X, Y, Q, $R_3$, $R_4$, $R_5$, $R_6$, $R_7$, $R_9$, m, n, and z are as defined in claim 1.

20. The process of claim 19, wherein the reaction takes place in the presence of a base and a compound L-$CH_2$—(C=O)—O—($C_1$-$C_6$-alkyl), wherein L is a halogen.

21. A method of treating an individual suffering from a cellular proliferative disorder, comprising administering to the individual an effective amount of at least one compound, or a pharmaceutically acceptable salt thereof, according to claim 1; wherein the cellular proliferative disorder is a cancer selected from the group consisting of ovarian cancer; cervical cancer; breast cancer; prostate cancer; testicular cancer, lung cancer, renal cancer; colorectal cancer; skin cancer; brain cancer; and leukemia.

22. A method according to claim 21, wherein the compound is selected from the group consisting of:
4-(((3,4-dimethoxyphenethyl)sulfonyemethyl)-2-methoxyphenol;
and pharmaceutically acceptable salts thereof.

23. The method according to claim 21, wherein the compound is 2-((2-methoxy-5-(((2,4,6-trimethoxyphenethyl)sulfonyl)methyl)phenyl)amino)acetic acid, or pharmaceutically acceptable salt thereof.

* * * * *